US012702699B2

(12) United States Patent
Cheng et al.

(10) Patent No.: US 12,702,699 B2
(45) Date of Patent: Aug. 11, 2026

(54) SUPEROXIDE DISMUTASE-LOADED POROUS POLYMERSOMES AS HIGHLY EFFICIENT ANTIOXIDANT NANOPARTICLES

(71) Applicant: The Trustees of the University of Pennsylvania, Philadelphia, PA (US)

(72) Inventors: Zhiliang Cheng, Newtown, PA (US); Andrew Tsourkas, Bryn Mawr, PA (US); Ling Qin, Moorestown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 781 days.

(21) Appl. No.: 18/054,586

(22) Filed: Nov. 11, 2022

(65) Prior Publication Data

US 2023/0144866 A1 May 11, 2023

Related U.S. Application Data

(60) Provisional application No. 63/278,121, filed on Nov. 11, 2021.

(51) Int. Cl.
*A61K 38/44* (2006.01)
*A61K 9/1273* (2025.01)
*A61P 9/02* (2006.01)
*A61P 19/02* (2006.01)
*A61P 39/06* (2006.01)

(52) U.S. Cl.
CPC .......... *A61K 38/446* (2013.01); *A61K 9/1273* (2013.01); *A61P 9/02* (2018.01); *A61P 19/02* (2018.01); *A61P 39/06* (2018.01)

(58) Field of Classification Search
None
See application file for complete search history.

(56) References Cited

U.S. PATENT DOCUMENTS

2009/0214419 A1* 8/2009 Therien .............. A61K 41/0057 514/23

OTHER PUBLICATIONS

Kartha et al (Adv. Healthcare Mater., 2017, 6, 1-6) (Year: 2017).*
Kartha et al (Adv. Healthcare Mater., 2017, 6, 1-6), Supporting Information (Year: 2017).*
Loeser et al., Osteoarthritis: A disease ofthe joint as an organ, Arthritis Rheum 64(6) (2012) 1697-1707.
Loukogeorgakis et al., Remote ischemic preconditioning provides early and late protection against endothelial ischemia-reperfusion injury in humans: role ofthe autonomic nervous system. JAm Coll Cardiol. 2005;46(3):450-456.
Luisa Corvo et al., Superoxide dismutase entrapped in long-circulating liposomes: formulation design and therapeutic activity in rat adjuvant arthritis, Biochim biophys acta, 2002, 1564(1), 227-236.
Lund-Olesen et al., Orgotein: anew anti-inflammatory metalloprotein drug: preliminary evaluation of clinical efficacy and safety in degenerative joint disease, Curr Ther Res Clin Exp 16(7) (1974) 706-17.
MacFarlane et al., Costenbader, Racial Variation in Total Knee Replacement in a Diverse Nationwide Clinical Trial, Jcr-J Clin Rheumatol 24(1) (2018) 1-5.
Mao et al., Electron spin resonance study on the permeability ofsuperoxide radicals in lipid bilayers and biological membranes, FEBS Lett 305(3) (1992) 233-236.
Mathiessen, Synovitis in osteoarthritis: current understanding with therapeutic implications, Arthritis Res Ther 19(1) (2017) 18.
McCord et al., Superoxide dismutase an enzymic function for erythrocuprein (hemocuprein). JBiol Chem. 1969;244(22): 6049-6055.
Monboisse et al., "Oxidative damage to collagen", Free Radicals and Aging, EXS 62, 1992, pp. 323-327.
Nagaoka et al., A New Therapeutic Modality for Acute Myocardial Infarction: Nanoparticle-Mediated Delivery of Pitavastatin Induces Cardioprotection from Ischemia-Reperfusion Injury via Activation ofPI3K/Akt Pathway and Anti-Inflammation in a Rat Model. PLoS One. 2015;10(7):e0132451.
Neogi, The epidemiology and impact of pain in osteoarthritis, Osteoarthr Cartilage 21(9) (2013) 1145-1153.
Ni et al., Ceria Nanoparticles Meet Hepatic Ischemia-Reperfusion Injury: The Perfect Imperfection. Adv Mater. 2019;31(40):el902956.
Nimse et al., Free radicals, natural antioxidants, and their reaction mechanisms, Rsc Adv 5(35) (2015) 27986-28006.
Odagiri et al., Local control of mitochondrial membrane potential, permeability transition pore and reactive oxygen species by calcium and calmodulin in rat ventricular myocytes. JMol Cell Cardiol. 2009;46(6), 989-997.
Omar, "Interstitial equilibration ofsuperoxide dismutase correlates with its protective effect in the isolated rabbit heart", Journal of Molecular and Cellular Cardiology, 1991, vol. 23, No. 2, pp. 149-159.

(Continued)

*Primary Examiner* — Celeste A Roney
(74) *Attorney, Agent, or Firm* — BakerHostetler

(57) ABSTRACT

Therapeutic compositions, comprising: an anti-reactive oxygen species agent and a pervious polymersome, the pervious polymersome encapsulating the anti-reactive oxygen species agent, and the pervious polymersome having therein channels defined by a channel diblock copolymer, the channels being arranged so as to retain at least some of the anti-reactive oxygen species agent within the pervious polymersome while allowing reactive oxygen species to pass into the pervious polymersome.
Method of treating a patient, comprising: administering an effective amount of a therapeutic composition, the therapeutic composition comprising an anti-reactive oxygen species agent disposed within a pervious polymersome, the pervious polymersome encapsulating the anti-reactive oxygen species agent, and the pervious polymersome having therein channels defined by a channel diblock copolymer, the channels being arranged so as to retain at least some of the anti-reactive oxygen species agent within the pervious polymersome while allowing reactive oxygen species to pass into the pervious polymersome.

27 Claims, 35 Drawing Sheets

(56) References Cited

OTHER PUBLICATIONS

Onaca et al., "SOD Antioxidant Nanoreactors: Influence ofBlock Copolymer Composition on the Nanoreactor Efficiency", Macromol Biosci, 2010, vol. 10, No. 5, pp. 531-538.
Pacher et al., Measurement of cardiac function using pressure-volume conductance catheter technique in mice and rats. Nat Protoc. 2008;3(9): 1422-1434.
Perez et al., Development or disease: duality ofthe mitochondrial permeability transition pore. Dev Biol. 2017;426(I), 1-7.
Piper, "Energy deficiency, calcium overload or oxidative stress: possible causes ofirreversible ischemic myocardial injury", Klin Wochenschr., 1989, vol. 67, No. 9, pp. 465-476.
Rahman, Studies on free radicals, antioxidants, and co-factors, Clin Interv Aging 2(2) (2007) 219-236.
Rajkovic et al., Reactive Oxygen Species—Responsive Nanoparticles for the Treatment of Ischemic Stroke. Adv Ther (Weinh). 2019;2(7): 1900038.
Reddy et al., Superoxide dismutase-loaded PLGA nanoparticles protect cultured human neurons under oxidative stress. Appl Biochem Biotechnol. 2008;151(2-3):565-577.
Regan et al., Extracellular superoxide dismutase and oxidant damage in osteoarthritis, Arthritis Rheum 52(11) (2005) 3479-3491.
Regan et al., Joint fluid antioxidants are decreased in osteoarthritic joints compared to joints with macroscopically intact cartilage and subacute injury, Osteoarthr Cartilage 16(4) (2008) 515-521.
Rideau et al., Liposomes and polymersomes: a comparative review towards cell mimicking, Chern Soc Rev 47(23)(2018)8572-8610.
Rosenblum et al., Progress and challenges towards targeted delivery of cancer therapeutics. Nat Commun. 2018;12;9(1):1410.
Roth et al., Global, Regional, and National Burden ofCardiovascular Diseases for 10 Causes, 1990 to 2015. J Am Coll Cardiol. 2017;70(I):1-25.
Ruiz-Romero et al., Mitochondrial dysregulation of osteoarthritic human articular chondrocytes analyzed by proteomics: a decrease in mitochondrial superoxide dismutase points to a redox imbalance, Mol Cell Proteomics 8(1) (2009) 172-189.
Sah et al., Recent Trends in Preparation of Poly(lactide-coglycolide) Nanoparticles by Mixing Polymeric Organic Solution with Antisolvent, J Nanomater 2015 (2015) 794601.
Salo et al., Superoxide dismutase undergoes proteolysis and fragmentation following oxidative modification and inactivation. JBiol Chem. 1990;265(20): 11919-11927.
Salvador et al., Hydroperoxyl, superoxide and pH gradients in the mitochondrial matrix: A theoretical assessment. Free Radic BiolMed. 2001;31(10):1208-1215.
Scherer et al., "Oxidative stress impairs the function of sarcoplasmic reticulum by oxidation of sulfhydryl groups in the Ca2+-ATPase", Arch Biochem Biophys., 1986, vol. 246, No. 2, pp. 589-601.
Scott et al., "Superoxide dismutase downregulation in osteoarthritis progression and end-stage disease", Ann Rheum Dis, 2010, vol. 69, No. 8, pp. 1502-1510.
Seshadri et al., The delivery ofsuperoxide dismutase encapsulated in polyketal microparticles to rat myocardium and protection from myocardial ischemia-reperfusion injury. Biomaterials. 2010;31(6): 1372-1379.
Sinusas, "Osteoarthritis: diagnosis and treatment", Am Fam Physician, 2012, vol. 85, No. 1, pp. 49-56.
Su et al., Systemic Review ofBiodegradable Nanomaterials in Nanomedicine. Nanomaterials (Basel). 2020;10(4):656.
Takimoto et al., Role of oxidative stress in cardiac hypertrophy and remodeling. Hypertension. 2007;49:241-248.
Tanaka et al., Evidence against the "early protection-delayed death" hypothesis ofsuperoxide dismutase therapy in experimental myocardial infarction. Polyethylene glycol-superoxide dismutase plus catalase does not limit myocardial infarct size in dogs. Circ Res. 1990;67(3):636-644.
Tsikas, "Assessment oflipid peroxidation by measuring malondialdehyde (MDA) and relatives in biological samples: Analytical and biological challenges", Anal Biochem., 2017, vol. 524, pp. 13-30.
Uraizee et al., Failure of superoxide dismutase to limit size ofmyocardial infarction after 40 minutes ofischemia and 4 days ofreperfusion in dogs. Circulation. 1987;75(6): 1237-1248.
Wang et al., Overexpression ofhuman copper, zinc-superoxide dismutase (SODI) prevents postischemic injury. Proc NatlAcad Sci USA. 1998;95(8):4556-4560.
Wang et al., The importance ofsynovial inflammation in osteoarthritis: current evidence from imaging assessments and clinical trials, Osteoarthr Cartilage 26(2) (2018) 165-174.
Wei et al., Phospholipase A(2) inhibitor-loaded micellar nanoparticles attenuate inflammation and mitigate osteoarthritis progression, Sci Adv 7(15) (2021)eabe6374.
Wei et al., Targeting cartilage EGFR pathway for osteoarthritis treatment, Sci Transl Med 13(576) (2021) eabb3946.
Wenham et al., The role ofsynovitis in osteoarthritis, Ther Adv Musculoskelet Dis 2(6) (2010) 349-359.
Yang et al., Cellular and molecular mechanisms of endothelial ischemia/reperfusion injury: Perspectives and implications for postischemic myocardial protection. Am J Transl Res. 2016;8(2):765-777.
Yellon et al., Myocardial reperfusion injury. NEnglJ Med. 2007;357(II): 1121-1135.
Youan, Microencapsulation ofsuperoxide dismutase into biodegradable microparticles by spray-drying. DrugDeliv. 2004;II(3):209-214.
Yun et al., Nanoparticles for targeted delivery of antioxidant enzymes to the brain after cerebral ischemia and reperfusion injury, J Cerebr Blood F Met 33(4) (2013) 583-592.
Zhou et al., "Rescue the retina after the ischemic injury by polymer-mediated intracellular superoxide dismutase delivery", Biomaterials., 2021, vol. 268:120600, pp. 1-40.
Altshuler et al., "Superoxide Dismutase-Loaded Nanoparticles Attenuate Myocardial Ischemia-Reperfusion Injury and Protect against Chronic Adverse Ventricular Remodeling", Adv. Ther-Germany, 2021, 4, 2100036.
Arslan et al., "Mesenchymal stem cell-derived exosomes increase ATP levels, decrease oxidative stress and activate PI3K/Akt pathway to enhance myocardial viability and prevent adverse remodeling after myocardial ischemia/reperfusion injury", Stem Cell Res., 2013, 10(3), 301-312.
Bae et al., "Hydrogen Peroxide-Responsive Nanoparticle Reduces Myocardial Ischemia/Reperfusion Injury", J. Am Heart Assoc., 2016, 5(II): e003697.
Bajpayee et al., "Avidin as a model for charge driven transport into cartilage and drug delivery for treating early stage post-traumatic osteoarthritis", Biomaterials, 2014, 35(1), 538-549.
Bartok et al., "Fibroblast-like synoviocytes: key effector cells in rheumatoid arthritis", Immunol Rev., 2010, 233(1) 233-255.
Batandier et al., "Opening of the mitochondrial permeability transition pore induces reactive oxygen species production at the level of the respiratory chain complex 1", J. Biol Chem, 2004, 279(17), 17197-17204.
Blanco et al., "Chondrocyte Apoptosis Induced by Nitric-Oxide", Am J Pathol., 1995, 146(1), 75-85.
Boltikbas et al., "Organ-Restricted Vascular Delivery of Nanoparticles for Lung Cancer Therapy", Adv. Ther. Weinh. 2020, 3(7): 2000017.
Braunersreuther et al., "Reactive Oxygen Species in Myocardial Reperfusion Injury: From Physiopathology to Therapeutic Approaches", Curr Pharm Biotechnol., 2011, 13(I), 97-1 14.
Brown et al., "Intra-articular targeting of nanomaterials for the treatment of osteoarthritis", Acta Biomater, 2019, 93, 239-257.
Brown et al., "Nanoparticle Properties for Delivery to Cartilage: The Implications of Disease State, Synovial Fluid, and Off-Target Uptake", Mol Pharm., 16(2) (2019) 469-479.
Burkhardt et al., "Oxygen Radicals as Effectors of Cartilage Destruction—Direct Degradative Effect on Matrix Components and Indirect Action Via Activation of Latent Collagenase from Polymorphonuclear Leukocytes", Arthritis Rheum., 1986, 29(3), 379-387.
Cadenas et al., "ROS and redox signaling in myocardial is chemiare perfusion injury and cardio protection", Free Radic Biol Med., 2018, 117, 76-89.

(56) References Cited

OTHER PUBLICATIONS

Carames et al., "The relationship of autophagy defects to cartilage damage during joint aging in a mouse model", Arthritis Rheumatol, 2015, 67(6), 1568-1576.
Chang et al., "Intracellular Implantation of Enzymes in Hollow Silica Nanospheres for Protein Therapy: Cascade System of Superoxide Dismutase and Catalase", Small, 2014, 10(22), 4785-4795.
Chi et al., "Effect of superoxide dismutase on myocardial infarct size in the canine heart after 6 hours of regional ischemia and reperfusion: a demonstration of myocardial salvage", Circ Res., 1989, 64(4), 665-675.
De Lange-Brokaar, "Synovial inflammation, immune cells and their cytokines in osteoarthritis; a review", Osteoarthr Cartilage, 2012, 20(12), 1484-1499.
Discher et al., "Polymer vesicles", Science, 2002, 297(5583), 967-973.
Donato et al., "Protecting the heart from ischemia/reperfusion injury: an update on remote ischemic preconditioning and postconditioning", Curr. Opin. Cardiol., 2017, 32(6), 784-790.
Dong et al., "Impact of ischemic preconditioning on ischemia-reperfusion injury of the rat sciatic nerve", IntJ Clin Exp Med., 2015, 8(9), 16245-16251.
Eugenia et al., "Liposomal superoxide dismutases and their use in the treatment of experimental arthritis", Method Enzymol, 2005, 391, 395-413.
Flaherty et al., "Recombinant human superoxide dismutase (h-SOD) fails to improve recovery of ventricular function in patients undergoing coronary angioplasty for acute myocardial infarction", Circulation, 1994, 89(5), 1982-1991.
Flohe, Superoxide dismutase for therapeutic use: clinical experience, dead ends and hopes, Mol Cell Biochem 84(2) (1988) 123-31.
Futami et al., Isolation and characterization of multipotential mesenchymal cells from the mouse synovium., Plos One, 2012, 7(9), e45517.
Gao et al., Targeted elimination ofintracellular reactive oxygen species using nanoparticle-like chitosan-superoxide dismutase conjugate for treatment ofmonoiodoacetate-induced osteoarthritis, Int J Pharmaceut 590 (2020) 119947.
Geiger et al., Cartilage-penetrating nanocarriers improve delivery and efficacy of growth factor treatment of osteoarthritis, Sci Transl Med 10(469) (2018) eaat8800.
Ghitman et al., Review ofhybrid PLGA nanoparticles: Future ofsmart drug delivery and theranostics medicine, Mater Design 193 (2020)108805.
Gorlach et al., Calcium and ROS: A mutual interplay. Redox Biol. 2015;6:260-271.a
Grill et al., Direct Measurement ofMyocardial Free Radical Generation in an In Vivo Model: effects of Postischemic Reperfusion and Treatment With Human Recombinant Superoxide Dismutase. JAm Coll Cardiol. 1992;20:1604-11.
Han et al., Selective nanoparticle-mediated targeting ofrenal tubular Toll-like receptor 9 attenuates ischemic acute kidney injury. Kidney Int. 2020;98(I):76-87.
He et al., Role of miR-1 and miR-133a in myocardial ischemic postconditioning. JBiomed Sci. 2011;18(1):22.
Hood et al., "Nanocarriers for vascular delivery of antioxidants", Nanomedicine, 2011, 6(7), 1257-1272.
Hossen et al., Smart nanocarrier-based drug delivery systems for cancer therapy and toxicity studies: A review. JAdv Res. 2019;15:1-18.
Huang et al., Bispecific Antibody Therapy for Effective Cardiac Repair through Redirection ofEndogenous Stem Cells. Adv Ther (Weinh). 2019;2(10): 1900009.
Jacobson et al., Mitochondrial oxidative stress and cell death in astrocytes—requirement for stored Ca2+ and sustained opening ofthe permeability transition pore. JCell Sci. 2002; 115(6), 1175-1188.
Jia et al., Enomoto-Iwamoto, L. Qin, EGFR signaling is critical for maintaining the superficial layer of articular cartilage and preventing osteoarthritis initiation, Proc Natl Acad Sci U S A 113(50) (2016) 14360-14365.
Jia et al., Qin, Loading-Induced Reduction in Sclerostin as a Mechanism of Subchondral Bone Plate Sclerosis in Mouse Knee Joints During Late-Stage Osteoarthritis, Arthritis Rheumatol 70(2) (2018) 230-241.
Kabu et al., Drug delivery, cellbased therapies, and tissue engineering approaches for spinal cord injury. JControl Release. 2015;219:141-154.
Karsdal et al., Disease-modifying treatments for osteoarthritis (DMOADs) ofthe knee and hip: lessons learned from failures and opportunities for the future, Osteoarthr Cartilage 24(12) (2016) 2013-2021.
Kartha et al., Superoxide Dismutase-Loaded Porous polymersomes as highly efficient antioxidants for treating neuropathic pain., adv. health mater., 2017, 6(17), 1-6.
Kavanaugh et al., Duvall, Particle-based technologies for osteoarthritis detection and therapy, Drug Deliv Transl Res 6(2) (2016) 132-47.
Khan et al., Global Epidemiology oflschemic Heart Disease: Results from the Global Burden of Disease Study. Cureus. 2020; 12(7): e9349.
Klamfeldt et al., Enhanced breakdown in vitro of bovine articular cartilage proteoglycans by conditional synovial medium. The effect ofsuperoxide dismutase and catalase, Scand J Rheumatol 16(1) (1987) 41-45.
Koike et al., Superoxide dismutase activity is significantly lower in end-stage osteoarthritic cartilage than non-osteoarthritic cartilage, Pios One 13(9) (2018) e0203944.
Kou et al., Biomaterialengineered intra-articular drug delivery systems for osteoarthritis therapy, Drug Deliv 26(1) (2019)870-885.
Lattouf et al., Picrosirius Red Staining: A Useful Tool to Appraise Collagen Networks in Normal and Pathological Tissues. JHistochem Cytochem. 2014;62(10):751-758.
Law et al., The underlying risk of death after myocardial infarction in the absence of treatment. Arch Intern Med. 2002;162(21):2405-2410.
Lepetsos et al., ROS/oxidative stress signaling in osteoarthritis, Biochim Biophys Acta 1862(4) (2016) 576-591.
Li et al., Injectable, highly flexible, and thermosensitive hydrogels capable of delivering superoxide dismutase. Biomacromolecules. 2009;10(12):3306-3316.
Liu et al., Recombinant PTD-Cu/Zn SOD attenuates hypoxia-reoxygenation injury in cardiomyocytes. Free Radic Res. 2013;47(5):386-93.

* cited by examiner

Age (W)
12 von Fray
DMM
SOD-NP
16 von Fray
18
20 von Fray
22
24 von Fray
Harvest

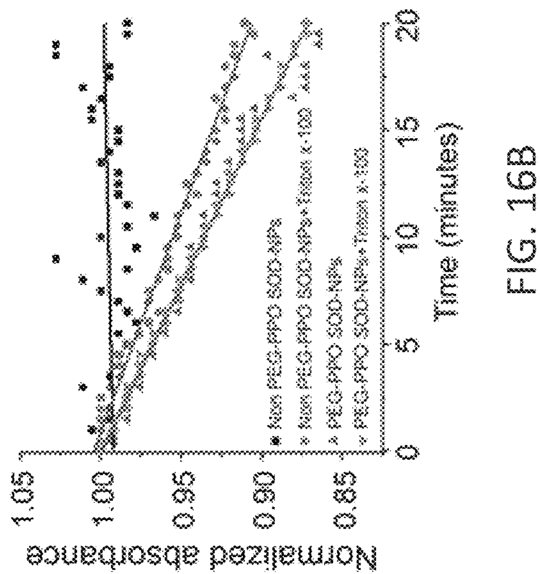
FIG. 16B
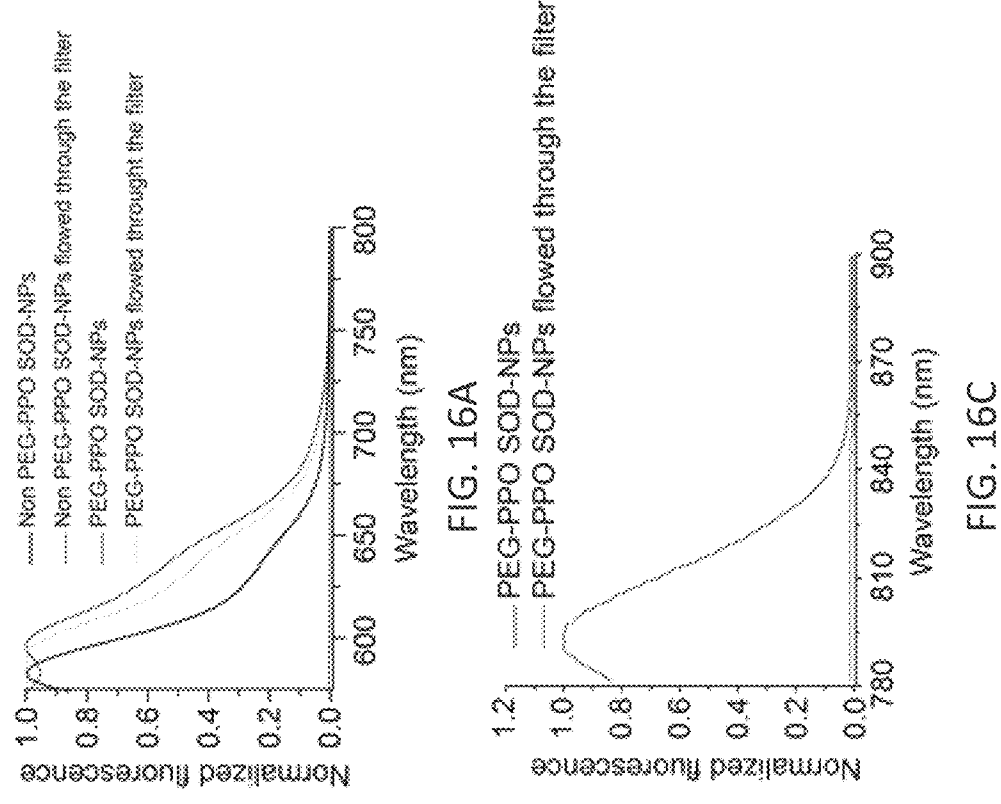
FIG. 16A
FIG. 16C

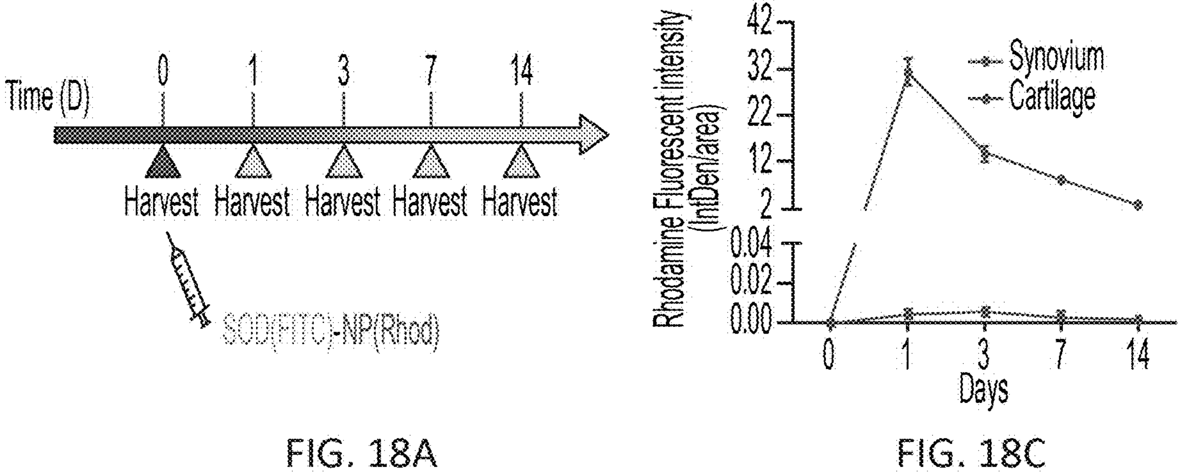
FIG. 18A
FIG. 18C
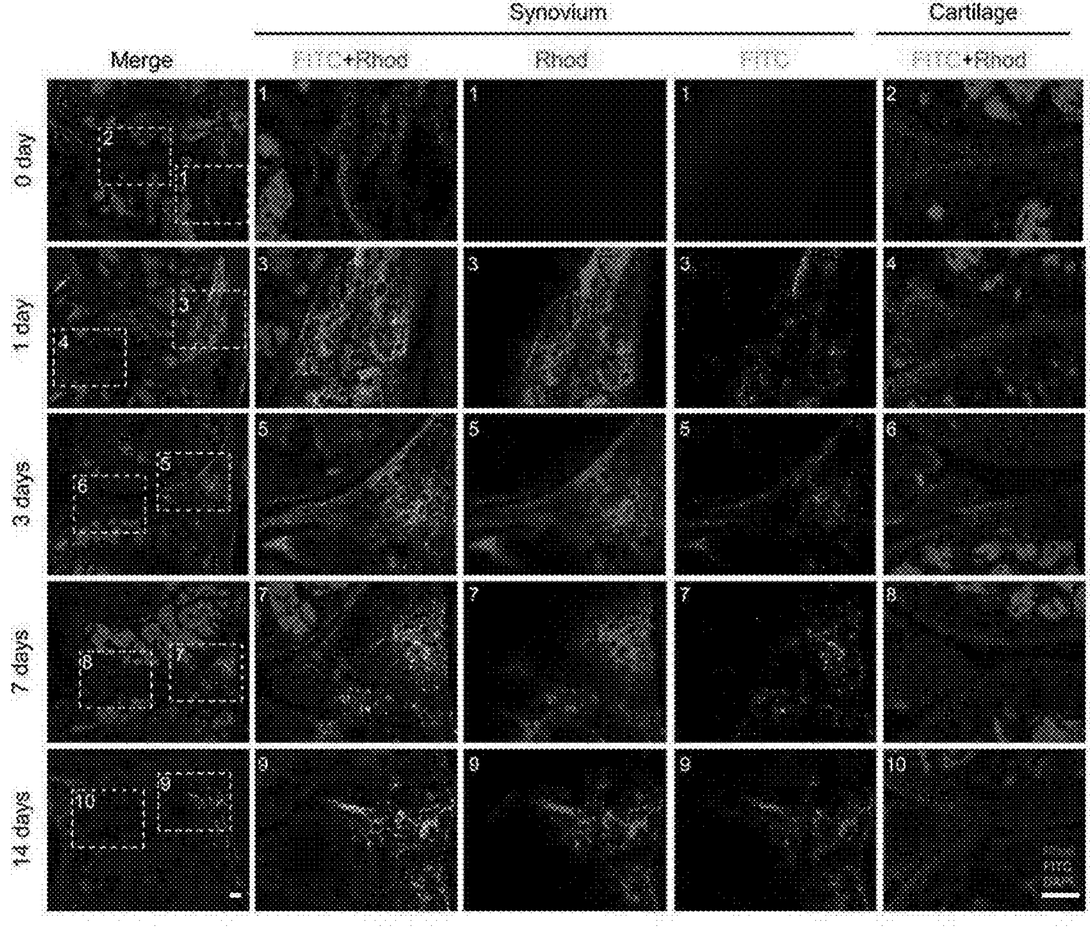
FIG. 18B

SUPEROXIDE DISMUTASE-LOADED POROUS POLYMERSOMES AS HIGHLY EFFICIENT ANTIOXIDANT NANOPARTICLES

CROSS-REFERENCE TO RELATED APPLICATIONS

This application claims benefit to U.S. Provisional Application No. 63/278,121, "Superoxide Dismutase-Loaded Porous Polymersomes As Highly Efficient Antioxidant Nanoparticles" (filed Nov. 11, 2021), the entirety of which is incorporated by reference herein for any and all purposes.

GOVERNMENT RIGHTS

This invention was made with government support under NS100892 awarded by the National Institutes of Health. The government has certain rights in the invention.

TECHNICAL FIELD

The present disclosure relates to the field of polymersomes and to the field of drug delivery.

BACKGROUND

Oxidative stress and the reactive oxygen species (ROS) have important roles in, inter alia, osteoarthritis (OA) development and in myocardial injury. However, the direct use of antioxidant enzymes, such as superoxide dismutase (SOD), is challenging due to a lack of effective drug delivery system. Accordingly, there is a need in the field for an effective drug delivery system for antioxidant enzymes.

SUMMARY

In meeting the described needs, the present disclosure provides a therapeutic composition, comprising: an anti-reactive oxygen species agent and a pervious polymersome, the pervious polymersome encapsulating the anti-reactive oxygen species agent, and the pervious polymersome having therein channels defined by a channel diblock copolymer, the channels being arranged so as to retain at least some of the anti-reactive oxygen species agent within the pervious polymersome while allowing reactive oxygen species to pass into the pervious polymersome.

Also provided are methods, comprising exogenous administration of a therapeutic composition according to the present disclosure (e.g., according to any one of Aspects 1-11) to the myocardium of a subject having an ischemic condition.

Further provided are methods, comprising exogenous administration of a therapeutic composition according to the present disclosure (e.g., according to any one of Aspects 1-11) to a joint of a subject having an osteoarthritic condition.

Additionally disclosed are methods, comprising exogenous administration of a therapeutic composition according to the present disclosure (e.g., according to any one of Aspects 1-11) to a subject having a septic condition, a respiratory condition (e.g., acute respiratory distress syndrome or ARDS), or a dermatologic condition.

Also provided are methods of treating a pathology of a patient in need of treatment thereof, comprising: administering an effective amount of a therapeutic composition, the therapeutic composition comprising an anti-reactive oxygen species agent disposed within a pervious polymersome, the pervious polymersome encapsulating the anti-reactive oxygen species agent, and the pervious polymersome having therein channels defined by a channel diblock copolymer, the channels being arranged so as to retain at least some of the anti-reactive oxygen species agent within the pervious polymersome while allowing reactive oxygen species to pass into the pervious polymersome.

Additionally disclosed are methods, comprising forming a therapeutic composition according to the present disclosure, e.g., according to any one of Aspects 1-11.

Also provided are kits, the kits comprising a therapeutic composition according to the present disclosure (e.g., any one of Aspects 1-11) and an injector configured to inject the therapeutic composition into a subject.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various aspects discussed in the present document. In the drawings:

FIG. 1A SOD remains encapsulated within a porous nanoparticle, composed of PEG-PBD and PEG-PPO, while free superoxide can diffuse through the pores. FIG. 1B: Diameter of NP-SOD as measured by DLS. FIG. 1C: SOD activity was tested before and after the treatment of porous and non-porous nanoparticles, with encapsulated SOD, with Triton X-100. Triton X-100 is used to disrupt the nanoparticle membranes and release the encapsulated SOD. Non-porous NP-SOD were composed entirely of PEG-PBD. FIG. 1D: Stability of NP-SOD in PBS for 1 week. FIG. 1E: Stability of NP-SOD in serum for 24 hours.

FIGS. 2A-2B: Presence of ROS free radicals at 3 hours post I/R was quantified by fluorescence intensity (Ex:485 nm) produced by cleavage of $H_2$DCFDA. FIGS. 2C-2D: H9C2 cells were seeded in multi-well chamber slides and subjected to either normoxic or I/R conditions before staining with JC-1. Samples were then mounted with DAPI and imaged on a Leica fluorescent microscope at 405/485/535 nm at 10, 40, and 100× magnifications. Image intensities of each excitation wavelength were quantified utilizing an automated ImageJ algorithm and set as a ratio of JC-1 aggregates (pink: 535 nm) to JC-1 monomers (green: 485 nm). Significance represented as follows: *p<0.05; p<0.01; *p<0.001; ****p<00.0001.

FIG. 3A-3B: Free SOD and NP-SOD were tagged with an IRDye 800CW dye and injected following 1 hour of myocardial ischemia. Hearts were explanted at 0.25, 24, and 72 hours post injection and imaged using the Spectrum In Vivo Imaging System (IVIS) imager (ex/em: 760/800 nm). Excitation of IRDye 800CW fluorescence was demarcated in regions of interest (ROIs) and magnification of signal was quantified using Perkin Elmer software and normalized to myocardial area. N=4 animals per group per timepoint.

FIGS. 4A-4B: Explanted hearts were flushed with PBS and cut into 2 mm sections along the short axis. Apical, mid, and basilar sections were incubated in 1% 2,3,5-Triphenyltetrazolium chloride (TTC) for 20 minutes at 37° C. before fixation in 4% PFA. Sections were imaged and the area of ischemic tissue across all apical and middle regions was quantified as a portion of the whole myocardium demonstrating the myocardial area at risk. FIG. 4C: LV myocardium was lysed and precipitated with Thiobarbituric Acid (TBA). MDA concentration was determined by colorimetric detection of TBA-MDA adduct formation as a measure of ROS induced lipid peroxidation. FIG. 4D: At 3-hours post I/R, echocardiography was performed across short and long axes. End-systolic and end-diastolic volumes were obtained in order to derive LV ejection fraction. Treatment groups assessed were as follows: Sham (n=4), PBS (n=6), free SOD (n=5), NP-SOD (n=7). Significance represented as follows: *p<0.05; p<0.01; *p<0.001; ****p<0.0001.

As shown in FIG. 6A, a hemodynamic analysis was performed using transthoracic echocardiography and intraventricular pressure-volume loop displacement. Clinical measures for preload-independent contractility (ESPVR) and other preload-dependent volumetric parameters were derived using Millar Pressure-Volume systems and LabChart analysis software. FIG. 6B provides representative PV loops during occlusion of the inferior vena cava (IVC) as are utilized in deriving ESPVR values. Y-axis represents LV pressure and X-axis represents volume. Treatment groups assessed were as follows: Sham (n=8), PBS (n=11), free SOD (n=9), NP-SOD (n=10). Significance represented as follows: *p<0.05; p<0.01; *p<0.001; ****p<0.0001.

FIG. 7A illustrates cytotoxicity of NP-SOD, free SOD and empty NP on H9C2 cells were compared to control (PBS)-treated cells via quantification of LDH release. No significant differences in LDH release were detected between groups at any time point. FIG. 7B illustrates H9C2 cell viability was assessed by MTT assay 24 hours after incubating cells in media containing NP-SOD, free SOD or empty NP for 4 hours. Viability was compared to that of cells incubated with PBS. No significant differences were detected between groups.

FIG. 9A illustrates a chematic diagram of SOD-loaded polymersomes with high membrane permeability for intra-articular joint injection. FIG. 9B illustrates an evaluation of SOD retention within PEG-PPO-doped polymersomes in PBS buffer (0.1 M, pH 7.4). The liquid that flowed through the filter was measured for fluorescence (red line). The fluorescence of unfiltered sample in the presence of Triton X-100 was also recorded (black line). The fluorescence intensity is normalized relative to the intensity of unfiltered sample at 790 nm. In FIG. 9C, the stability of SOD-NPs in bovine synovial fluid was accessed by monitoring the hydrodynamic diameter for up to 24 hours. In FIG. 9D, the cytotoxicity of SOD-NPs was determined by measuring the cell viability of primary chondrocytes after coincubation with SOD-NPs at various SOD concentrations.

FIG. 10A illustrates representative images of healthy and OA mouse knee joints over 28 days after intra-articular injection of IRDye 800CW-labeled SOD or SOD-NPs. FIG. 10B provides a quantitative analysis of time course radiant efficiency within knee joints after intra-articular injection of IRDye 800CW-labeled SOD or SOD-NPs. (n=6/group). FIG. 10C provides a quantitative analysis of area under the curve (AUC) based on fluorescence intensity profile in (B). (n=6/group). *P<0.001, **P<0.0001.

FIG. 11A provides HE staining of normal mouse knee joint showing the anatomy and location of synovium and cartilage. S: Synovium, C: Cartilage. FIG. 11B provides representative fluorescence images of SOD(FITC)-NP(Rhod) distribution in mouse knee joints at day 0 (before injection) and 1, 3, 7 and 14 days after intra-articular injection. White boxes with the numbers in the merged images denote the magnified view of the synovium and cartilage in the injured mouse knee joint. For synovium tissues, magnified regions labeled with FITC (green color), Rhod (red color) and the merged FITC, Rhod and DAPI (blue color) are provided, respectively. For cartilage tissues, only magnified regions from the merged FITC, Rhod and DAPI are provided. Scale bar: 200 μm. FIG. 11C provides semi-quantification of rhodamine fluorescence intensity in synovium or cartilage. (n=3/group). FIG. 11D provides immunofluorescence staining of Pdgfra in mouse synovium tissue at 14 days post SOD(FITC)-NP(Rhod) injection. SSL: synovial sublining layer. Scale bar: 100 μm.

FIG. 12A provides representative fluorescence images of mouse SFs treated with SOD(FITC)-NP(Rhod) for 24 h. Scale bar: 50 μm. FIG. 12B provides measurement of H2DCFDA levels in mouse SFs after being treated by TNFα plus PBS, empty NP, SOD, or SOD-NP for 24 h. (n=3/group). FIG. 12C provides representative immunohistochemistry images of 8-OHdG in human synovial tissues treated with PBS alone or IL-1β in combination with PBS, empty NP, SOD or SOD-NPs for 8 days. Scale bar: 100 μm. As shown in FIG. 12D, the mean ratio of integrated optical density (IOD) to area (IOD/area) was used to semi-quantify 8-OHdG amount. (n=5/group). FIG. 12E provides an immunohistochemistry staining of Mmp13. Scale bar, 100 μm. FIG. 12F provides a semi-quantitative evaluation of Mmp13 amount represented as IOD/area. (n=5/group). FIG. 12G provides immunohistochemistry staining of Adamts5. Scale bar: 100 μm. FIG. 12H provides a semi-quantitative evaluation of Adamts5 amount represented as IOD/area. (n=5/group). *P<0.05, P<0.01, *P<0.001, ****P<0.0001.

FIG. 13A provides a schematic diagram of study design. WT mice at 12 weeks of age received sham or DMM surgery and were treated by intra-articular injections of PBS, empty NP, SOD or SOD-NPs immediately and once every 2 weeks. Joints were harvested 12 weeks later for analyses. FIG. 13B provides safranin O/Fast Green staining of knee joints at 12 weeks after surgery. Low: low-magnification images; high: high-magnification images of black boxed areas above. Scale bars, 200 μm. As shown in FIG. 13C, the OA severity of knee joints was measured by Mankin score. (n=6/group). FIG. 13D provides the average uncalcified cartilage thickness (Uncal. Th.) of knee joints. (n=6/group). FIG. 13E provides a hematoxylin and eosin staining of synovium. Black boxed areas indicate the synovial tissues. Scale bar, 200 μm. In FIG. 13F, synovitis scores were quantified. (n=6/group). In FIG. 13G, representative 3D color maps derived from micro-CT images showing femoral subchondral bone plate (SBP) thickness. Color ranges from 0 (blue) to 240 μm (red). FIG. 13H provides a quantification of SBP thickness. (n=6/group). *P<0.05, P<0.01, *P<0.001, ****P<0.0001.

FIG. 15A: Schematic diagram of study design. WT mice at 12 weeks of age received sham or DMM surgery and were treated by intra-articular injections of PBS, empty NP, SOD or SOD-NPs from 4 weeks post-surgery with once every 2 weeks. Joints were harvested 12 weeks after surgery for analyses. FIG. 15B: Safranin O/Fast Green staining of knee joints. Low: low-magnification image; high: high-magnification image of the black boxed area above. Scale bars, 200 μm. FIG. 15C: Hematoxylin and eosin staining of synovium. Black boxed areas indicate synovial tissue. Scale bar, 200 μm. FIG. 15D: The OA severity of knee joints in FIG. 15B was measured by Mankin score. (n=6/group). FIG. 15E: Synovitis score of FIG. 15C was measured. (n=6/group). FIG. 15F: von Frey assay at 4, 8 and 12 weeks after DMM surgery. The data of day 0 was acquired before DMM surgery. PWT: paw withdrawal threshold. (n=6/group). *P<0.05, P<0.01, *P<0.001, ****P<0.0001.

FIGS. 16A-16C. Characterization of SOD-NPs. FIG. 16A: 10 mg/ml SRB (Mw: 559 Da) was encapsulated within the polymersomes of 100 mol % PEG-PBD or 75 mol % PEG-PBD and 25 mol % PEG-PPO. The unencapsulated SRB was removed by PD-10 column. After incubating in 0.1 M PBS (pH 7.4) for 24 hours, the polymersomes were centrifugated via centrifugal filter devices (Amicon Ultra-4, 100,000 MWCO, Millipore Corp.). The liquid that flowed through the filter and unfiltered stock sample were measured for fluorescence. The fluorescence intensity was normalized relative to the intensity of unfiltered sample at 583 nm. FIG. 16B. IRDye 800CW-SOD-loaded polymersomes (doped with 25 mol % PEG-PPO) were incubated in bovine synovial fluid for 24 hours. The polymersomes were then centrifugated via centrifugal filter devices (Amicon Ultra-4, 100,000 MWCO, Millipore Corp.). Then, the liquid that flowed through the filter and unfiltered stock sample were measured for fluorescence. The fluorescence intensity was normalized relative to the intensity of unfiltered sample at 795 nm. FIG. 16C. The SOD activity within PEG-PPO doped- and non PEG-PPO-doped polymersomes. SOD activity was normalized based on the SOD activity in the presence of Triton X-100.

FIG. 17A: Representative fluorescence images of SOD(FITC) distribution in mouse knee joints at day 0 (before injection) and 1, 3, 7 and 14 days after intra-articular injection. White boxes with the numbers in the merged images denote the magnified view of the synovium and cartilage in the injured mouse knee joint. Scale bar: 200 μm. FIG. 17B: Semi-quantification of FITC fluorescence intensity in synovium or cartilage. (n=3/group).

FIGS. 18A-18C. In vivo biodistribution of SOD-NPs in healthy mouse knee joint. FIG. 18A: Schematic diagram of study design. FIG. 18B: Representative fluorescence images of SOD(FITC)-NP(Rhod) distribution in mouse knee joints at day 0 (before injection) and 1, 3, 7 and 14 days after intra-articular injection. White boxes with the numbers in the merged images denote the magnified view of the synovium and cartilage in the injured mouse knee joint. For synovium tissues, magnified regions labeled with FITC (green color), Rhod (red color) and the merged FITC, Rhod and DAPI are provided, respectively. For cartilage tissues, only magnified regions from the merged images of FITC, Rhod and DAPI are provided. Scale bar: 200 μm. FIG. 18C: Semi-quantification of rhodamine fluorescence intensity in synovium or cartilage. (n=3/group).

FIG. 19A; Representative fluorescence images of SOD(FITC) distribution in mouse knee joints at day 0 (before injection) and 1, 3, 7 and 14 days after intra-articular injection. White boxes with the numbers in the merged images denote the magnified view of the synovium and cartilage in the injured mouse knee joint. Scale bar: 200 μm. FIG. 19B: Semi-quantification of FITC fluorescence intensity in synovium or cartilage. (n=3/group).

FIG. 21A: Biodistribution of IRDye 800CW-labeled SOD-NPs within healthy mouse knee joints at 24 h post single intra-articular injection. FIG. 21B: Semiquantitative analysis of fluorescent radiant efficiency in the different components of knee joints at 24 h post intra-articular injection (n=3/group). FIG. 21C: Biodistribution of IRDye 800CW-labeled SOD-NPs within major organs and blood sample at 1 day and 28 days post single injection of PBS or IRDye 800CW-labeled SOD-NPs.

FIG. 21D: Quantification of radiant efficiency within different organs and blood sample at indicated time points (n=3/group).

FIG. 23A: HE staining of knee joints at 12 weeks post sham or DMM surgery with indicated treatments. Scale bar: 200 μm. FIG. 23B: HE staining of indicated organs from Sham and SOD-NPs treated mice. Scale bar: 200 μm.

DETAILED DESCRIPTION OF ILLUSTRATIVE EMBODIMENTS

Figures 1A, 1B, 1C, 1D, 1E:
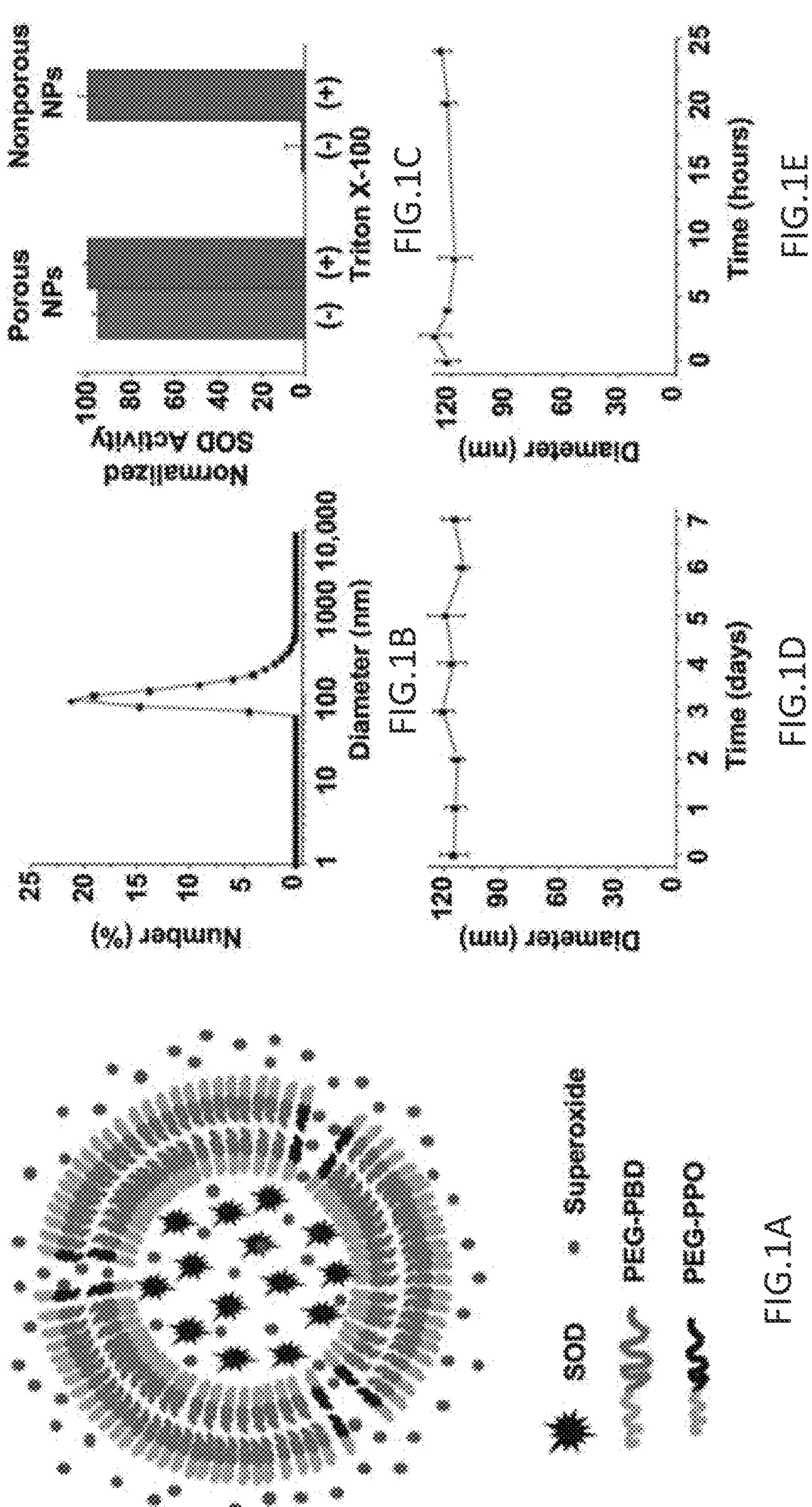
FIGS. 1A-1E. Porous nanoparticle construct retains SOD while maintaining activity.

The present disclosure may be understood more readily by reference to the following detailed description of desired embodiments and the examples included therein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms “a,” “an,” and “the” include plural referents unless the context clearly dictates otherwise.

As used in the specification and in the claims, the term “comprising” may include the embodiments “consisting of” and “consisting essentially of” The terms “comprise(s),” “include(s),” “having,” “has,” “can,” “contain(s),” and variants thereof, as used herein, are intended to be open-ended transitional phrases, terms, or words that require the presence of the named ingredients/steps and permit the presence of other ingredients/steps. However, such description should be construed as also describing compositions or processes as “consisting of” and “consisting essentially of” the enumerated ingredients/steps, which allows the presence of only the named ingredients/steps, along with any impurities that might result therefrom, and excludes other ingredients/steps.

As used herein, the terms “about” and “at or about” mean that the amount or value in question can be the value designated some other value approximately or about the same. It is generally understood, as used herein, that it is the nominal value indicated±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is “about” or “approximate” whether or not expressly stated to be such. It is understood that where “about” is used before a quantitative value, the parameter also includes the specific quantitative value itself, unless specifically stated otherwise.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently of the endpoints (e.g., “between 2 grams and 10 grams, and all the intermediate values includes 2 grams, 10 grams, and all intermediate values”). The endpoints of the ranges and any values disclosed herein are not limited to the precise range or value; they are sufficiently imprecise to include values approximating these ranges and/or values. All ranges are combinable.

As used herein, approximating language may be applied to modify any quantitative representation that may vary without resulting in a change in the basic function to which it is related. Accordingly, a value modified by a term or terms, such as “about” and “substantially,” may not be limited to the precise value specified, in some cases. In at least some instances, the approximating language may correspond to the precision of an instrument for measuring the value. The modifier “about” should also be considered as disclosing the range defined by the absolute values of the two endpoints. For example, the expression “from about 2 to about 4” also discloses the range “from 2 to 4.” The term “about” may refer to plus or minus 10% of the indicated number. For example, “about 10%” may indicate a range of 9% to 11%, and “about 1” may mean from 0.9-1.1. Other meanings of “about” may be apparent from the context, such as rounding off, so, for example “about 1” may also mean from 0.5 to 1.4. Further, the term “comprising” should be understood as having its open-ended meaning of “including,” but the term also includes the closed meaning of the term “consisting.” For example, a composition that comprises components A and B may be a composition that includes A, B, and other components, but may also be a composition made of A and B only. Any documents cited herein are incorporated by reference in their entireties for any and all purposes.

Exemplary Disclosure—Ischemia

Revascularization relieves myocardial ischemia but induces additional reperfusion injury by oxidative stress. Superoxide dismutase (SOD) is a potent antioxidant with preclinical promise in reducing reperfusion injury but is not well retained within the myocardium.

Hypothesis: Use of SOD-encapsulated nanoparticles (NP-SOD) will improve SOD retention and preserve cardiac function in a rat model of myocardial ischemia-reperfusion (I/R) injury.

Methods: Ischemia was maintained for 60 minutes via occlusion of the left anterior descending artery (LAD). Immediately prior to reperfusion, intramyocardial injections of NP-SOD, free SOD or phosphate buffered saline (PBS) were administered along the border of ischemic myocardium. Acute injury was assessed 3 hours post-reperfusion (n=8 per group), and chronic injury at 4 weeks (n=12).

Hemodynamics were measured by echocardiography and pressure-volume loops. Acute and chronic injury were examined histologically. Protein isolates at 3 hours measured mediators of cell-death. Intramyocardial enzyme retention analysis was performed by injecting NP or free fluorescent-tagged SOD and explanting hearts for imaging at 0, 24 and 72 hours (n=4 per group).

Results: Intramyocardial SOD retention was 25% greater in NP-SOD than free SOD at 24 hours ($p<0.01$) and 78% greater at 72 hours ($p<0.01$). NP-SOD exhibited improved ventricular function by ejection fraction at 4 weeks (64%) compared to free SOD (51%; $p<0.01$) and PBS (43%; $p<0.01$). Cardiac output, stroke volume and end-systolic elastance were greater in NP-SOD. Histology at 28 days demonstrated 54% less macroscopic fibrosis and 85% less microscopic collagen deposition in NP-SOD compared to PBS, and 33/79% compared to free SOD (all $p<0.05$). Quantifying RIPK3 protein levels in 'at risk' myocardium at 3 hours demonstrated 2.5-fold reduced upstream necrosome activation.

Conclusions: NP-SOD provides prolonged enzyme retention within the myocardium. Intramyocardial NPSOD administration prior to reperfusion attenuates acute myocardial injury and protects against chronic adverse ventricular remodeling. SOD acts by downregulating necrosis. These findings suggest potential for NP-SOD based therapy in mitigating myocardial I/R injury.

Early revascularization is critical to reduce morbidity after myocardial infarction, although reperfusion incites additional oxidative injury. Superoxide dismutase (SOD) is an antioxidant that scavenges reactive oxygen species (ROS) but has low endogenous expression and rapid myocardial washout when administered exogenously. This study utilizes a novel nanoparticle carrier to improve exogeneous SOD retention while preserving enzyme function. Its role is assessed in preserving cardiac function after myocardial ischemia-reperfusion (I/R) injury. Here, nanoparticle-encapsulated SOD (NP-SOD) exhibits similar enzyme activity as free SOD, measured by ferricytochrome-c assay. In an in vitro I/R model, free and NP-SOD reduce active ROS, preserve mitochondrial integrity and improve cell viability compared to controls. In a rat in vivo I/R injury model, NP-encapsulation of fluorescent-tagged SOD improves intramyocardial retention after direct injection. Intramyocardial NP-SOD administration in vivo improves left ventricular contractility at 3-hours post-reperfusion by echocardiography and 4-weeks by echocardiography and invasive pressure-volume catheter analysis. These findings suggest that NP-SOD mitigates ROS damage in cardiac I/R injury in vitro and maximizes retention in vivo. NP-SOD further attenuates acute injury and protects against myocyte loss and chronic adverse ventricular remodeling, demonstrating potential for translating NP-SOD as a therapy to mitigate myocardial I/R injury.

1. Introduction

Ischemic heart disease remains the leading cause of morbidity and mortality worldwide, with over seven million people experiencing a myocardial infarction (MI) annually.[1,2] Untreated, mortality associated with MI exceeds 30%.[3] Current treatment paradigms prioritize urgent revascularization through percutaneous coronary intervention (PCI), which are critical in limiting ischemic injury and preserving cardiac function. Reperfusion, however, generates additional cellular injury due to a buildup of reactive oxygen species (ROS) related to an abrupt change from a hypoxic to a hyperoxic milieu.[4]

ROS accumulate both intracellularly within the cardiomyocytes and the vascular endothelium, as well as extracellularly as the immune system undergoes oxidative burst.[4-6] Intracellularly, ROS disrupt $Ca^{2+}$ equilibrium, impair paracrine signaling, and result in cell death.[7] This occurs through depletion of the sarcoplasmic reticulum and increased $Ca^{2+}$ ion flux between depolarized mitochondria and the cytosol, opening the mitochondrial permeability transition pore (mPTP) and dissipating the chemiosmotic gradient required for ATP production.[1-12] Increased cytosolic $Ca^{2+}$ and depleted oxidative phosphorylation have also been linked to decrements in contractility and viability in cardiomyocytes secondary to ischemia-reperfusion (I/R) injury.[13,14]

Innate protective mechanisms exist to attenuate I/R injury. One important early ROS scavenging enzyme is superoxide dismutase (SOD), which functions inside the mitochondria and cytosol and catalyzes the conversion of free radical superoxide ($O_2^{\cdot -}$) into hydrogen peroxide ($H_2O_2$) in a pathway ultimately yielding oxygen and water. Given its potential to act early in mitigating oxidative damage, SOD is an attractive potential therapeutic target in reducing I/R injury. Recombinant SOD has been shown to reduce free radical accumulation in isolated rabbit myocardium[[15,16] and mitigate I/R injury in cardiomyocytes,[17] while in vivo I/R injury was attenuated in transgenic mice overexpressing SOD.[18]

Despite its potent antioxidant properties, use of exogeneous SOD has yielded inconsistent results.[15,19,20] This has been attributed to the enzyme's intrinsic properties, namely, a short half-life, rapid tissue washout, and limited membrane permeability.[21-23]

Coupling antioxidant enzymes to carrier vehicles has been increasingly used to enhance enzyme bioavailability. Nanoparticle carriers have been shown to protect enzymes against proteolysis in neuronal I/R injury and other models of oxidative stress,[24-29] similar to larger microparticles and polyethylene-glycol (PEG)-based delivery modalities.[30,31] This study utilized a novel NP-encapsulated SOD (NP-SOD) which, unlike many other carriers, allows for delivery of unmodified enzyme, protection from proteolysis, and access to ROS via a highly porous membrane. Previously shown to be beneficial in a model of neurologic injury,[24] this antioxidant-nanoparticle construct was adapted for use in cardiac I/R injury. The goal of this study was to evaluate the efficacy of NP-SOD in reducing myocardial I/R injury through enhanced enzyme stability and bioavailability.

2. Results

2.1. SOD-Loaded Porous Polymersomes Retain SOD while Maintaining Enzyme Activity NP-SOD was developed by containing SOD within polymersomes composed of 75 mol % Poly(ethylene glycol) (900)-polybutadiene (1800) copolymer (denoted PEG-PBD)/25 mol % poly(ethylene glycol) (450)-poly(propylene oxide) (1400) copolymer (denoted PEG-PPO), FIG. 1A. The SOD encapsulation efficiency within these NPs was 20.17%. Dynamic light scattering (DLS) showed that NP-SOD had a mean diameter of 116 nm (FIG. 1B). As shown in FIG. 1C, SOD displayed high catalytic activity following nanoparticle encapsulation, indicating that superoxide radicals can access the encapsulated SOD through the porous membrane of PEG-PBD/PEG-PPO polymersomes. The activity of SOD following disruption of the polymersome with Triton X-100 was similar to the activity of NP-SOD without Triton X-100 treatment. In contrast, when SOD was encapsulated in nonporous polymersomes made from 100 mol % PEG-PBD, SOD activity was only detected after disrupting the nonporous polymersomes with Triton X-100 treatment. These results indicate that SOD-encapsulated PEG-PBD/PEG-PPO polymersomes provide a permeable membrane that allows free superoxide radicals to pass into the aqueous interior and interact with the encapsulated antioxidant enzyme SOD. In addition, DLS measurements showed that there were no significant changes in the hydrodynamic diameter when NP-SOD were incubated in phosphate buffered saline (PBS) for 1 week (FIG. 1D) and in serum for 24 hours (FIG. 1E).

2.2. SOD Provides Protection Against Cellular Oxidative Stress In Vitro

Figure 2A:
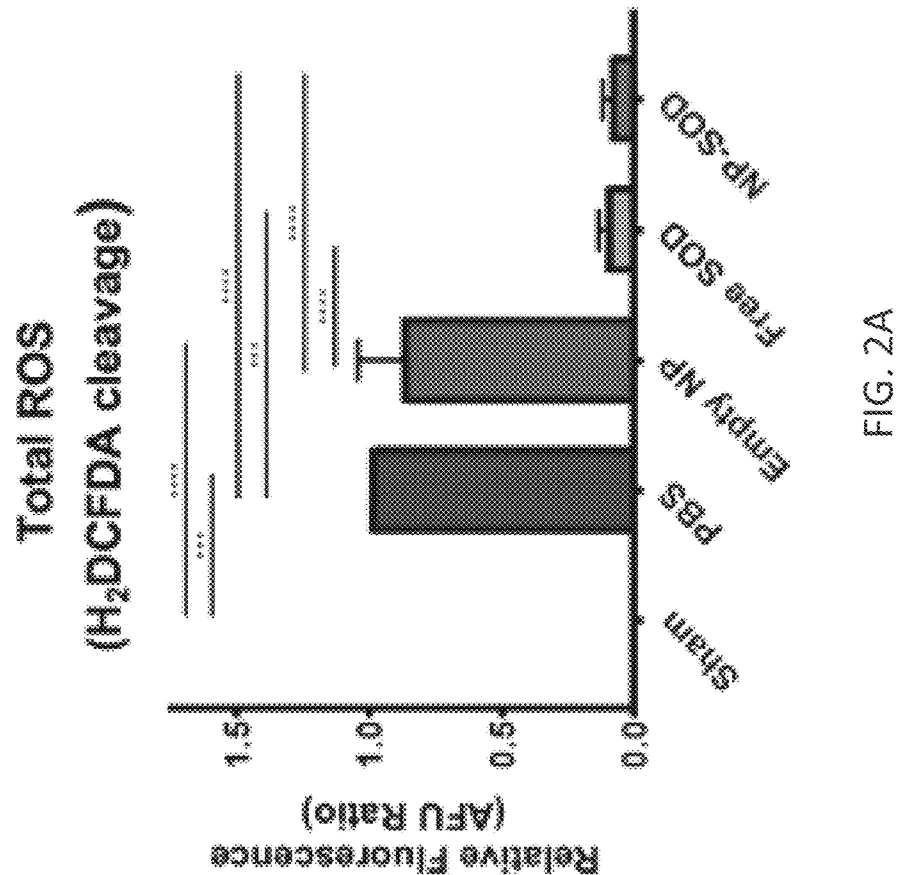
FIGS. 2A-2D. SOD minimizes oxidative injury in H9C2 cells following simulation of I/R injury. H9C2 cells were subjected to 1 hour of ischemia (0.5% $O_2$) prior to administration of treatment groups and were returned to normoxic conditions (21% $O_2$).
Figure 2B:
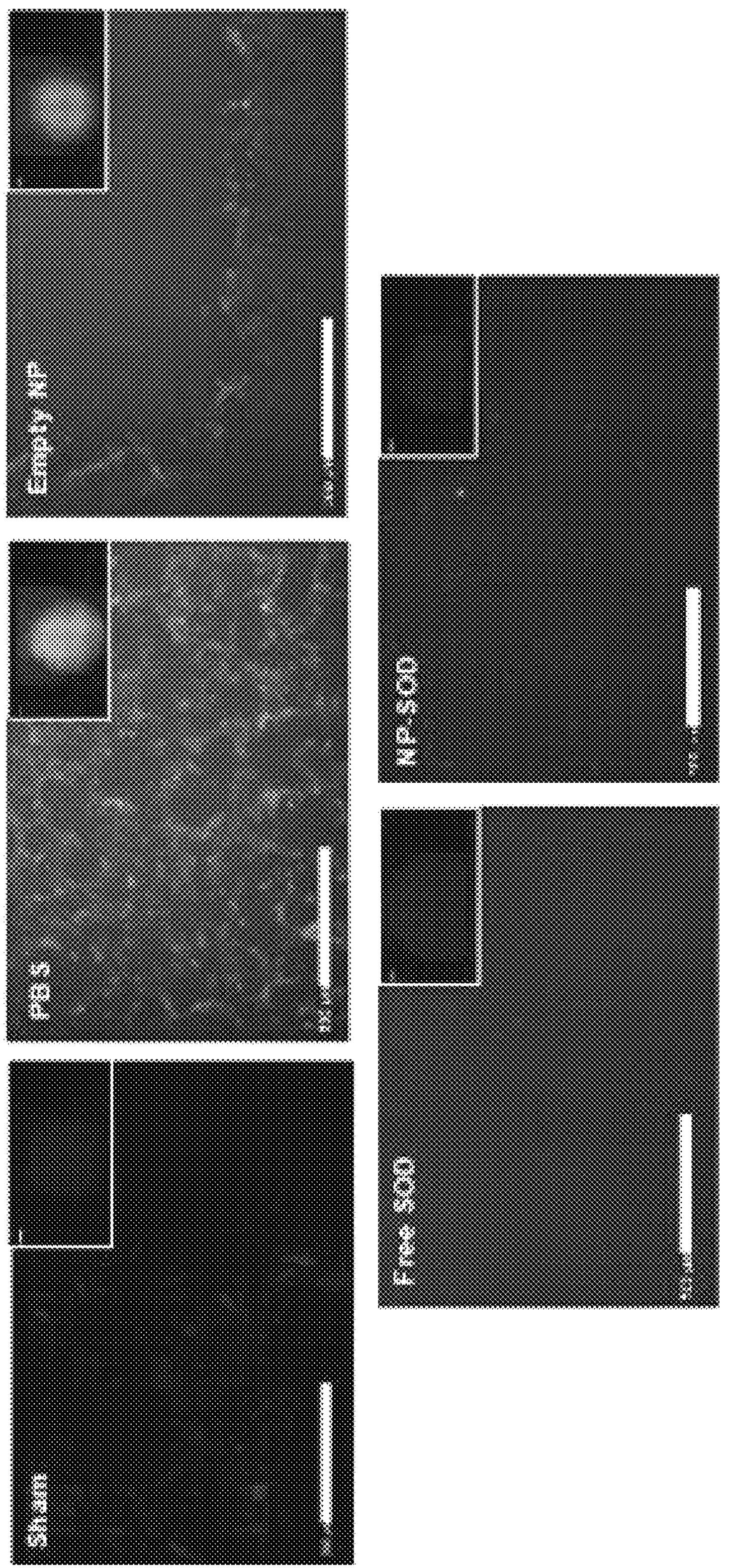
Figure 2C:
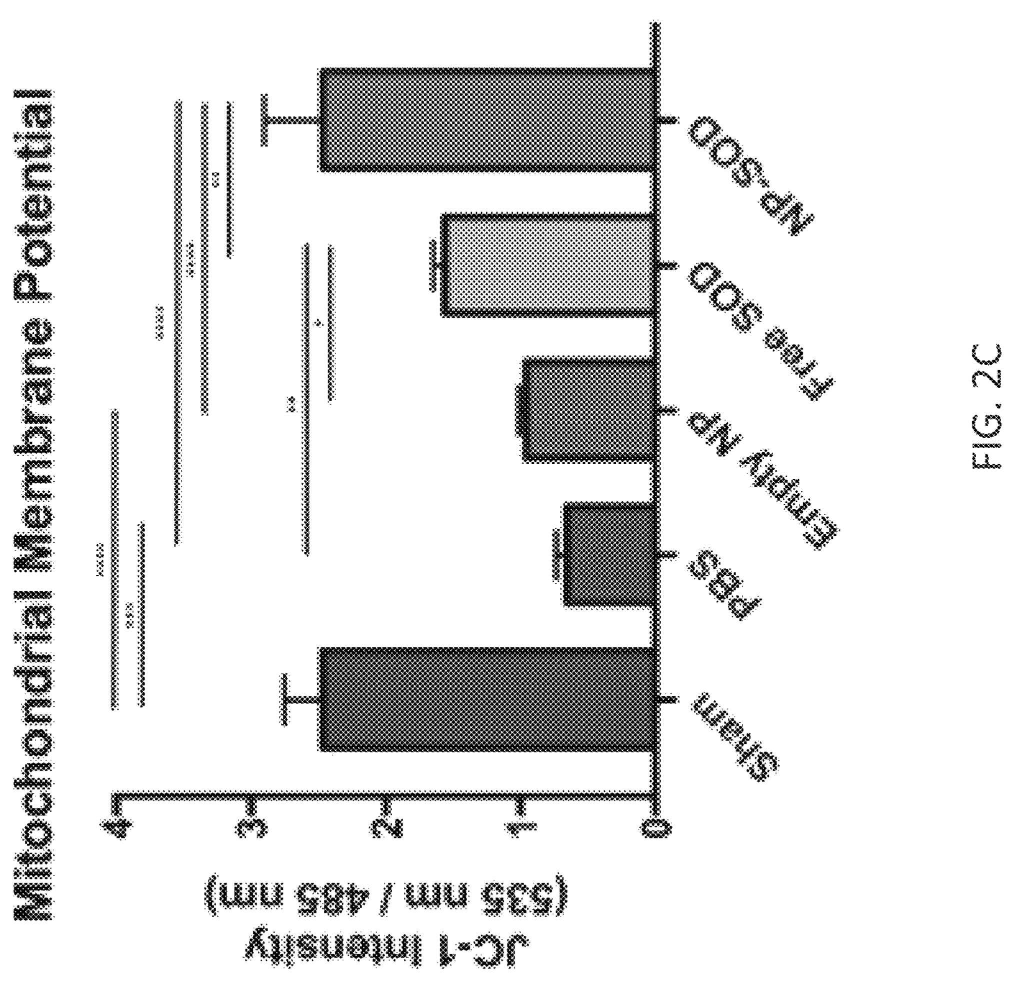
Figure 2D:
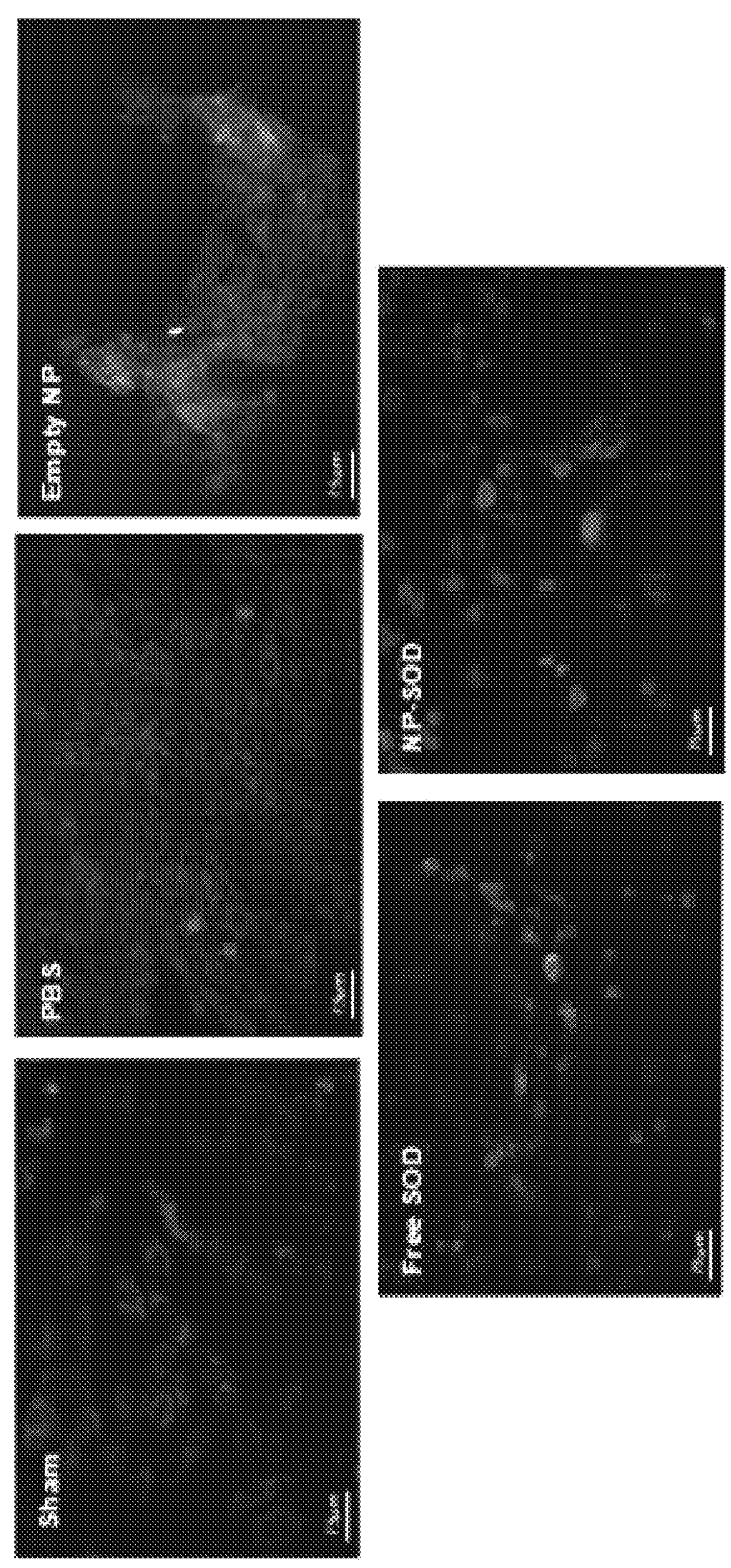
Figures 7A, 7B:
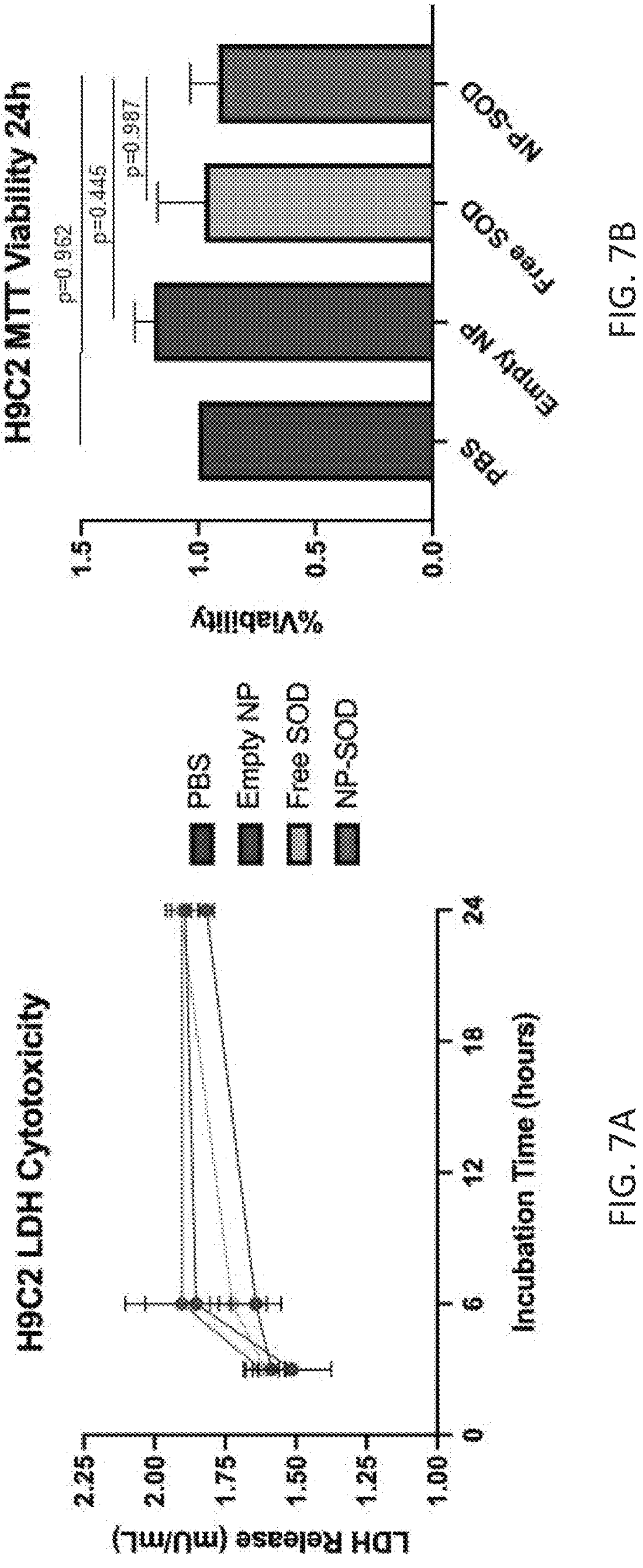
FIGS. 7A-7B. Administration of porous polymersome and antioxidant enzymes do not cause cardiomyoblast cytotoxicity or decreased viability.

The therapeutic effect of SOD in an in vitro model of I/R was assessed using the general oxidative stress fluorescence indicator dye $H_2DCFDA$. ROS cleavage of $H_2DCFDA$ was diminished and fluorescent intensity reduced in free and NP-SOD treated cells compared to those treated with empty NP or PBS, FIG. 2A/B. Cellular redox state was further assessed via mitochondrial membrane permeability. As mPTP opening is an early and lethal event in the cellular mechanisms behind ROS damage,[9,13] preservation of membrane polarization indicates a more favorable redox state. JC-1 aggregate/monomer intensity ratios in untreated, uninjured cells was 2.48; NP-SOD (2.47) preserved mitochondrial membrane potential compared to free SOD (1.56, p=0.003), empty NP (0.96, p<0.001) and PBS (0.66, p<0.001; FIG. 2C/D). Cytotoxicity of NP-SOD, free SOD and empty NP were additionally analyzed by measuring cardiomyoblast lactate dehydrogenase (LDH) release while cell viability was measured through 3-(4,5-dimethylthiazol-2-yl)-2,5-diphenyltetrazolium bromide (MTT) assay. At 24 hours, NP-SOD, free SOD and empty NP-treated cells demonstrated comparable, minimal cytotoxicity and cell viability to PBS-treated cells, FIG. 7.

Figure 3A:
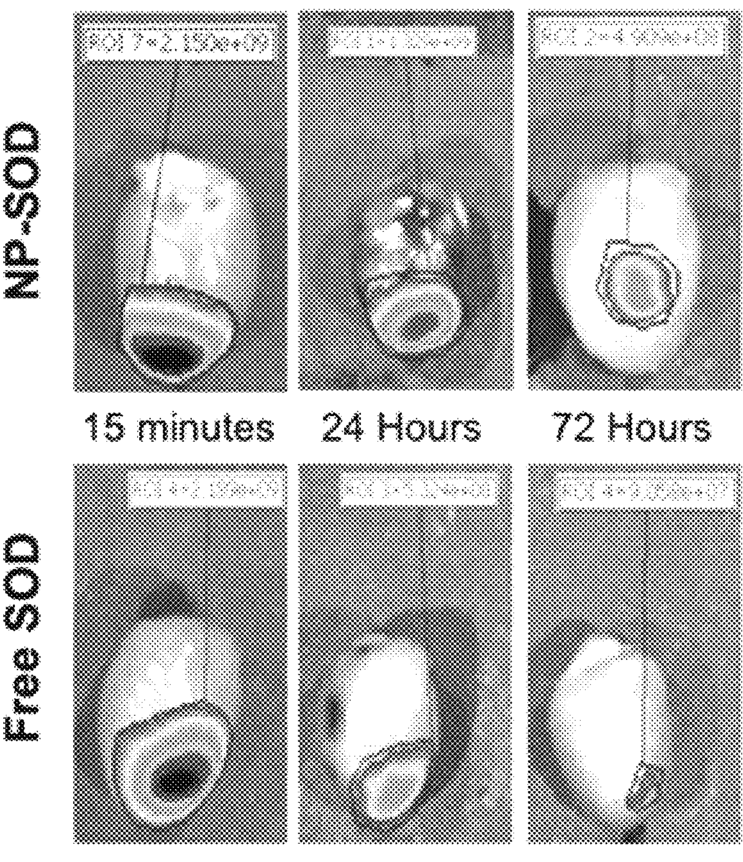
FIGS. 3A-3B. NP-SOD increases enzyme retention in the myocardium following I/R injury.
Figure 3B:
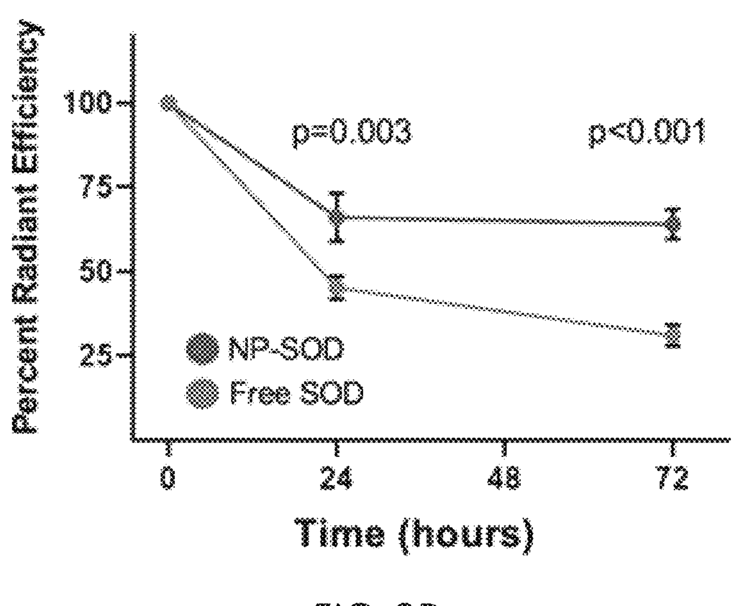

2.3. Nanoparticle Encapsulation Improves Intramyocardial SOD Retention In Vivo An important theorized distinction between antioxidant enzyme-nanoparticle therapy and antioxidant enzyme alone lies in the former's ability for enhanced retention within the myocardium. Using an in vivo rat I/R injury model, fluorescent-tagged SOD was more effectively retained within the myocardium at longer timepoints when NP-encapsulated rather than freely administered (FIG. 3). At 24 hours after reperfusion NP-SOD retention was 65.06% of baseline compared to 44.79% in freely administered SOD (p=0.003); at 72 hours, retention was 63.25% that of baseline in NP-SOD vs. 30.46% in free SOD (p<0.001).

2.4. NP-SOD Reduces I/R Injury In Vivo

Figures 4A, 4B, 4C, 4D:
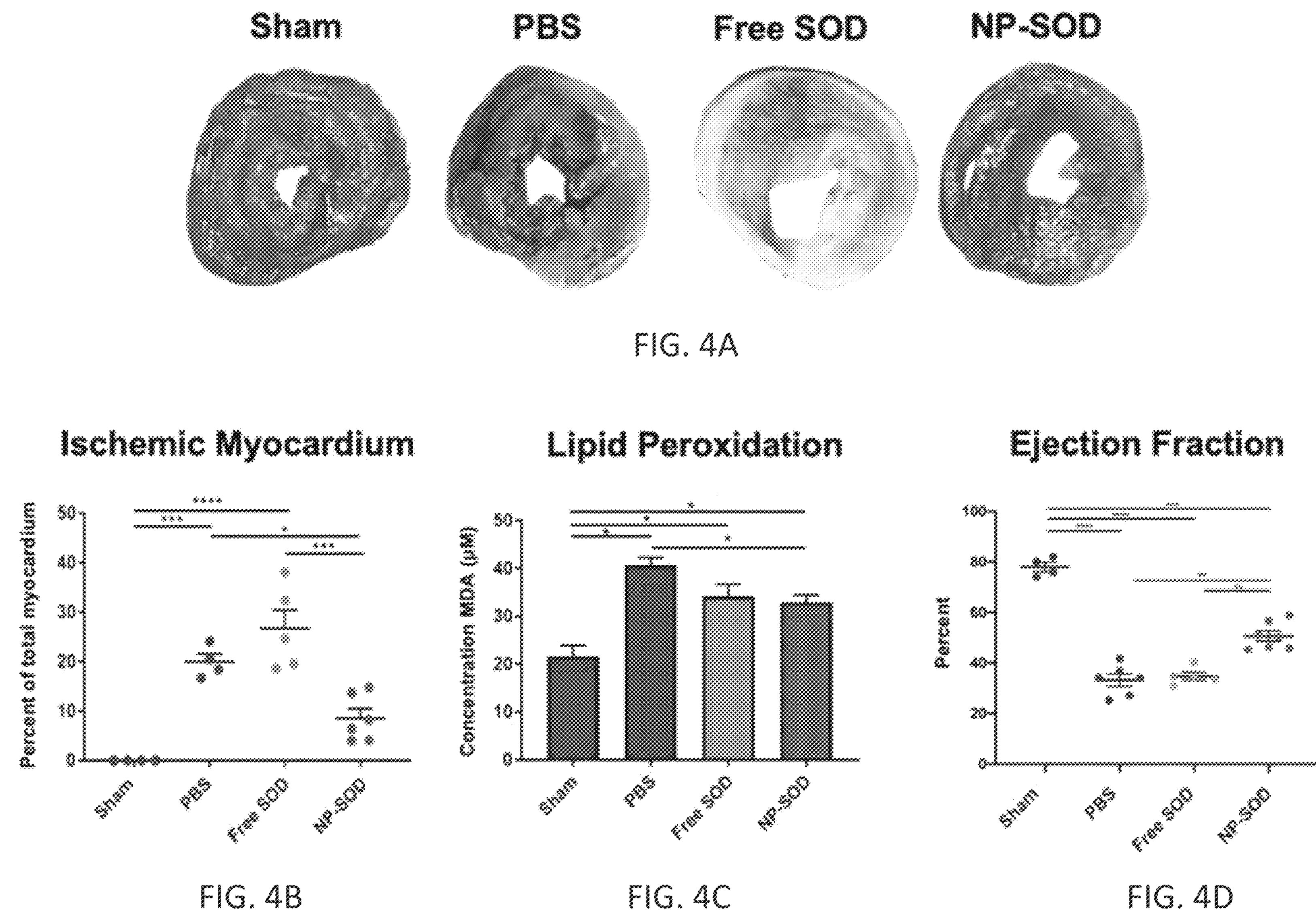
FIGS. 4A-4D. NP-SOD administration minimizes acute oxidative injury following I/R in vivo.

2.4.1. NP-SOD Protects Against Acute Oxidative Injury Following I/R in Rats Exogenous SOD administration was assessed in vivo during the acute phase of myocardial I/R injury. At 3 hours, 7 NP-SOD, 5 free SOD, 6 PBS and 4 sham animals were assessed. NP-SOD administration decreased post-reperfusion myocardial ischemia histologically (FIG. 4A). Mean area at risk (AAR) of mid-papillary cross sections in sham animals was 0%, while NP-SOD (AAR 12.1%) was lower than both PBS (33.0%, p=0.044) and free SOD (53.7%, p<0.001), FIG. 4B. To explain this protective effect, lipid peroxidation was measured via free malondialdehyde (MDA) concentration in border-zone tissue lysates. MDA concentration was reduced in NP-SOD treated rats compared to those receiving PBS, (32.95 vs. 40.74 μM, p=0.039), while lipid peroxidation in NP-SOD was comparable to free SOD (32.23 μM, p=0.961), FIG. 4C. Functional degree of acute myocardial injury was then measured by echocardiography. Comparing sham (n=4), NP-SOD (n=7), PBS (n=6) and free SOD (n=5), left ventricular (LV) function was preserved in the NP-SOD group (ejection fraction [EF]=50.6+/−2.0%) compared to PBS (33.2+/−2.5%, p<0.001) and free SOD (34.8+/−1.5%, p<0.001), FIG. 4D. There was no significant difference between PBS and free SOD-treated animals (p=0.949).

2.4.2. NP-SOD Attenuates Chronic Adverse Ventricular Remodeling

Figures 5A, 5B, 5C, 5D:
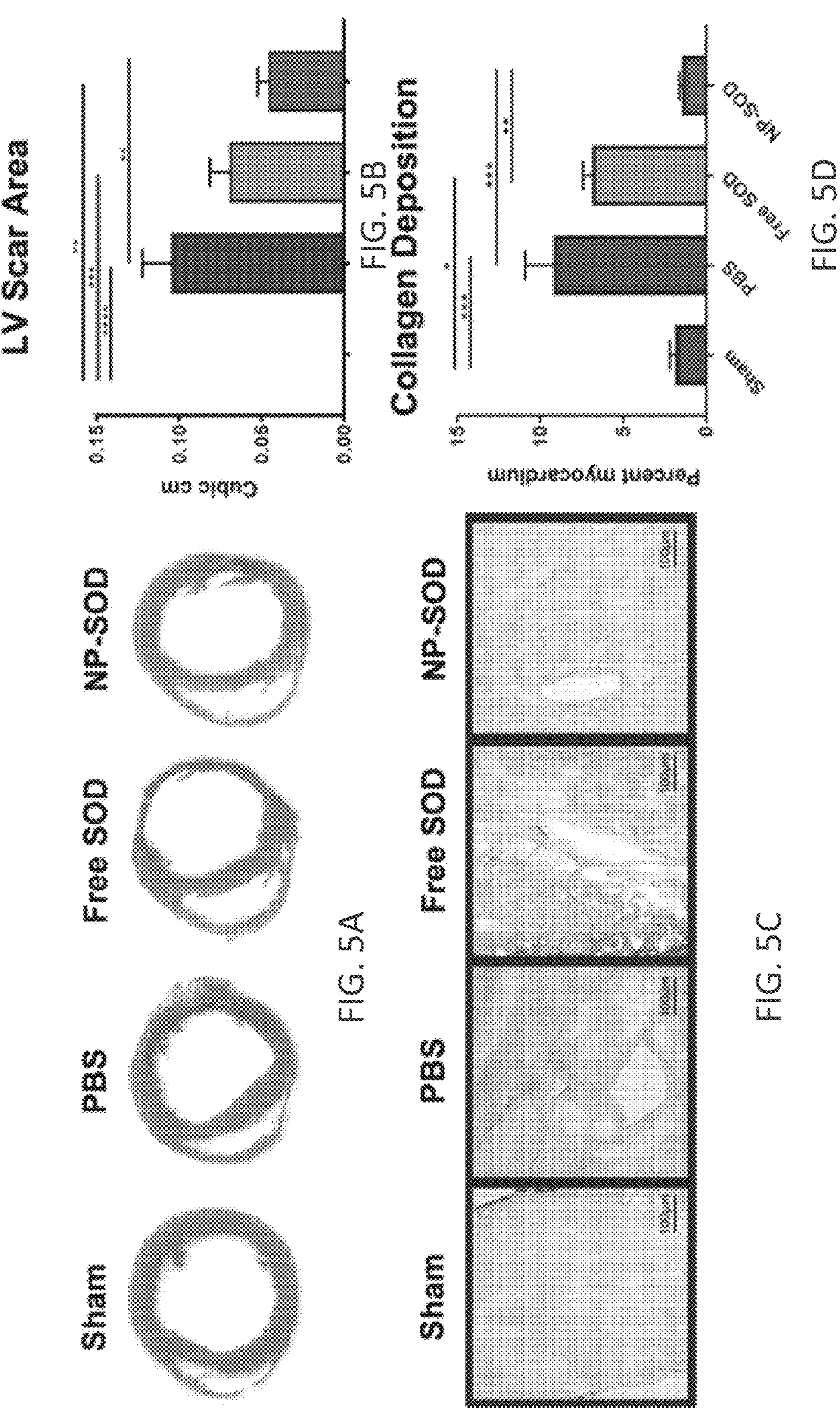
FIGS. 5A-5D. Chronic ventricular remodeling following I/R injury is attenuated by NP-SOD treatment. Hearts were explanted at 28-days post I/R, washed, sectioned and mounted at 10 μM in OCT. Sections including mid-papillary muscles in the LV were selected as representative regions affected by previous I/R injury. Masson's Trichrome and Picrosirius red stains were performed on sections before bright field imaging and automated ImageJ quantification of area containing blue fibrotic scar (FIG. 5A with quantitative analysis (FIG. 5B) and red type I collagen (FIG. 5C) with quantitative analysis (FIG. 5D) for the respective stains. Treatment groups assessed were as follows: Sham (n=9), PBS (n=12), free SOD (n=10), NP-SOD (n=13). Significance represented as follows: *p<0.05; p<0.01; *p<0.001; ****p<0.0001.
Figure 8:
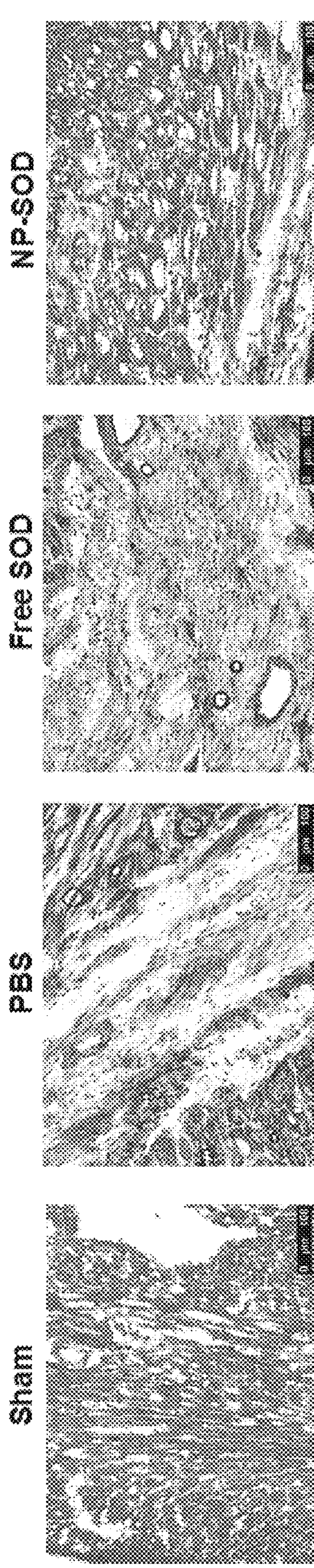
FIG. 8. Hearts treated with NP-SOD preserved cardiomyocyte density and morphology 4 weeks after I/R injury. H&E staining was performed on 10 μM cryosections of myocardium 4 weeks following myocardial I/R injury. Compared to sham controls, myofiber necrosis and inflammatory infiltrate were reduced in NP-SOD-treated animals relative to those treated with free SOD and PBS while myocyte density and size was greater in NP-SOD treated rats.

Treatment effects were additionally analyzed in the chronic setting. Sham (n=9), NP-SOD (n=13), PBS (n=12) or free SOD (n=10) treated rats were assessed 28 days post I/R injury via terminal hemodynamic measurements with subsequent heart explant. Comparing extent of adverse LV remodeling via fibrosis, there was a stepwise decrement in LV scar area from PBS (10.4+/−1.7%, n=7) to free SOD (6.9+/−1.1%, n=5), while NP-SOD demonstrated the least scar burden (4.6+/−0.6%, n=8; NP-SOD to PBS p=0.007), FIG. 5A/5B. Assessing myocardial remodeling at a microscopic level revealed even greater NP-SOD therapeutic efficacy, as fibrotic scar replacement encompassed 1.4+/−0.2% of LV myocardium in NP-SOD animals (n=5) compared to 9.2+/−1.7% in PBS (n=5, p<0.001) and 6.9+/−0.6% in free SOD animals (n=4, p=0.006), FIG. 5C/5D. These results were further corroborated by Hematoxylin & Eosin (H&E) staining of hearts subjected to I/R injury which demonstrated greater myocyte density and decreased fibrosis in NP-SOD treated hearts compared to free SOD and PBS, FIG. 8.

Figure 6A:
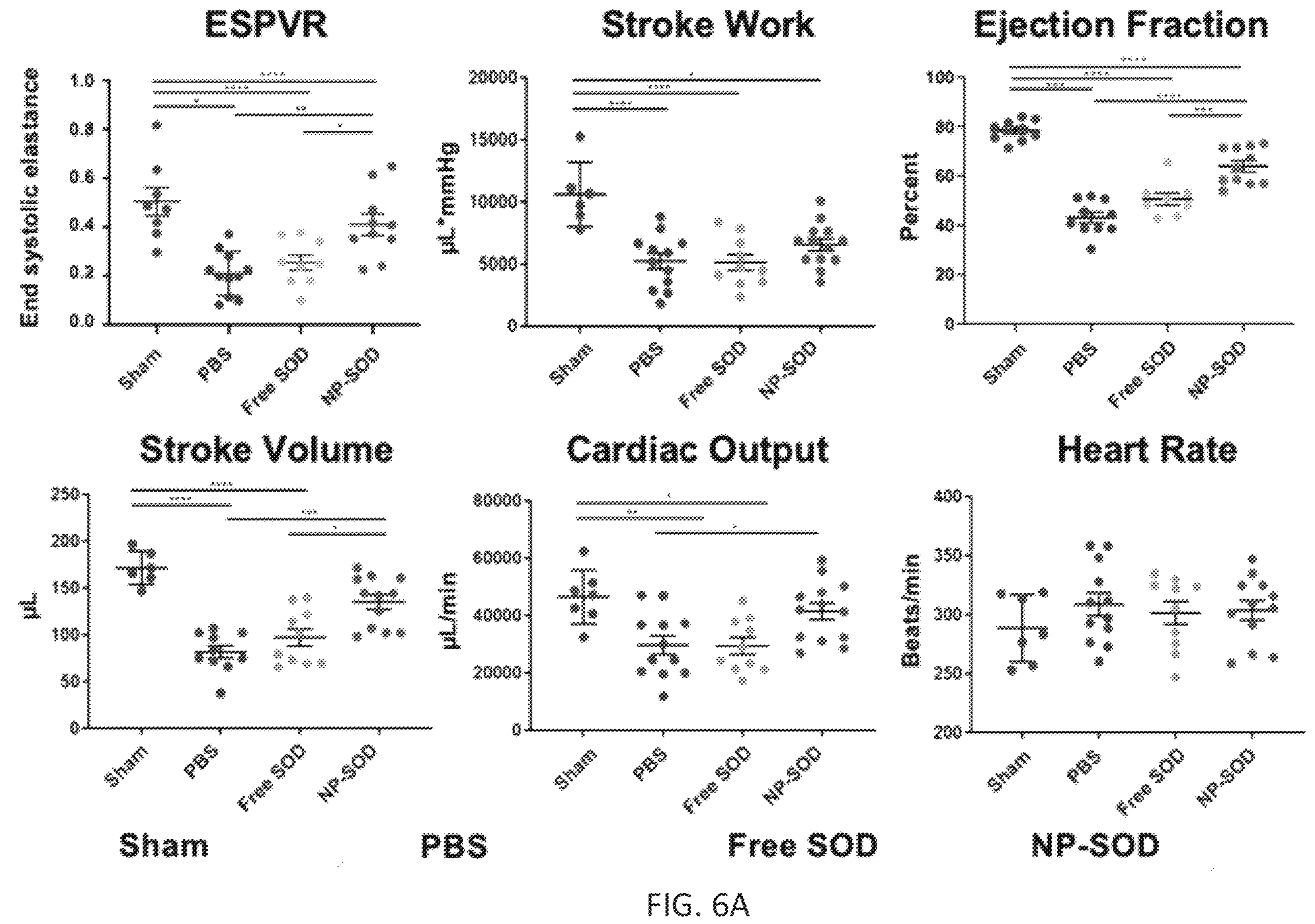
FIGS. 6A-6B. Cardiac function is preserved in animals treated with NP-SOD at 28 days following I/R injury.
Figure 6B:
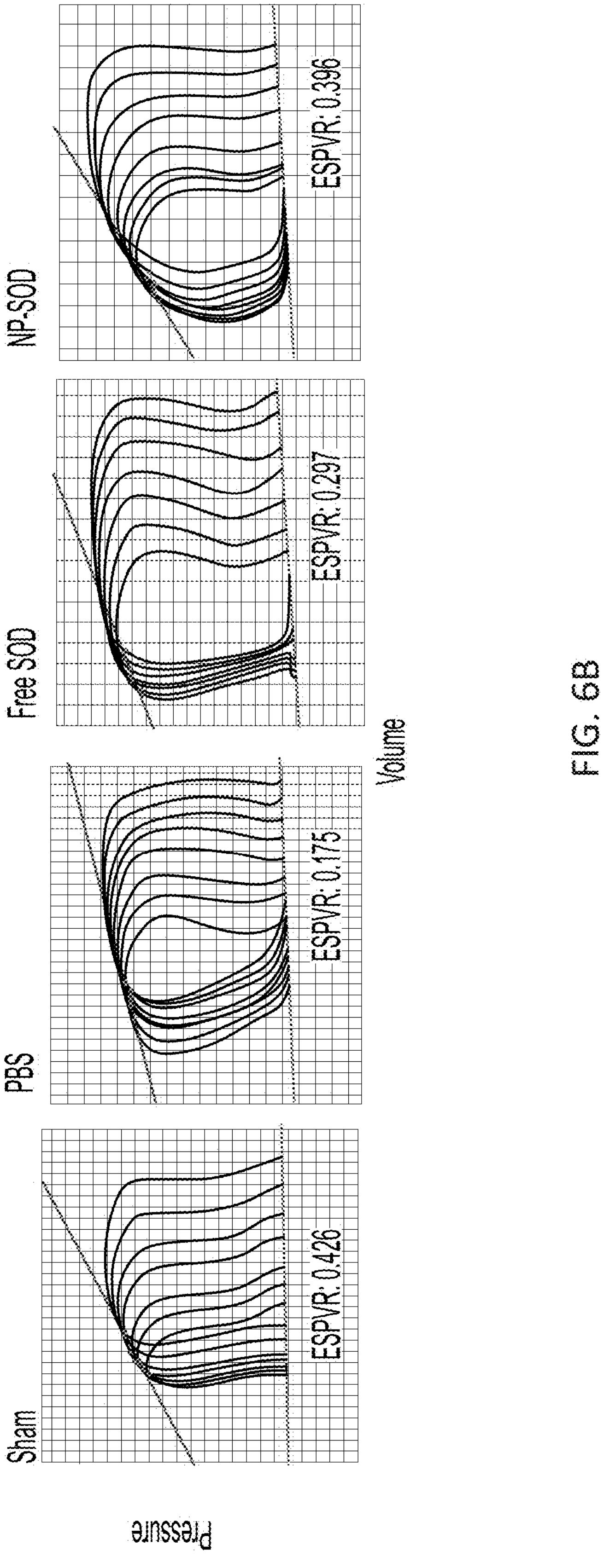

Hemodynamic function at 28 days was assessed through echocardiography and invasive intra-ventricular pressure-volume loop recordings. The primary hemodynamic outcome, end systolic pressure-volume relation (ESPVR), assesses for preload-independent contractility; this was significantly higher in the NP-SOD group, FIG. 6. ESPVR of sham animals was 0.50+/−0.05 (n=8) and 0.41+/−0.043 in NP-SOD animals (n=10, p=0.376). ESPVR in the NP-SOD group was 49.1% greater than PBS (n=11, p=0.003) and 38.1% greater than free SOD (n=9, p=0.042). Other preload-dependent markers of LV function similarly showed NP-SOD superiority. Mean EF, measured by echocardiography, was 64.8% in NP-SOD animals compared to 45.1% in the PBS group (p<0.001) and 50.2% in those receiving free SOD (p<0.001). Other pressure-volume catheter measured parameters were heart rate, cardiac output, stroke volume and stroke work. Heart rate was similar across treatment groups, while stroke volume demonstrated superiority in NP-SOD compared to both PBS and free SOD groups.

2.5. Discussion

This manuscript has described the creation and use of a novel nanoparticle construct to encapsulate SOD and allow for more efficient, sustained antioxidant function in the setting of myocardial I/R injury. This was done by first characterizing the unique permeable, biocompatible nature of the nanoparticle itself. The NP-SOD construct was further shown to maintain therapeutic efficacy in an in vitro I/R setting, in which NP-SOD and free SOD were both able to efficiently scavenge ROS and maintain mitochondrial integrity without causing additional cytotoxicity or cell death. Translating to an in vivo myocardial I/R setting, SOD retention within the myocardium was improved with NP-encapsulated; this correlated with NP-SOD protecting against acute injury as well as chronic ventricular remodeling. SOD has long been considered an attractive therapy in reducing oxidative damage but has failed to translate into pre-clinical success, and this construct provides promise into restoring its translational potential.

To date, treatment failure of SOD has been attributed to its intrinsic characteristics such as short half-life (4-8 minutes),[21] tissue washout,[32] and rapid proteolysis.[33] Attempts to address these shortcomings to-date have successfully enlisted the use of delivery vehicles by harboring SOD within liposoma[34] or polymersome[24] constructs or enmeshing it within hydrogels.[35-37] Despite these advances, prior studies have observed limitations in delivery vehicles' ability to balance the need for stability and preservation of SOD with the accessibility and permeability required to treat affected tissue. For example, in order for SOD-loaded liposomes or polymersomes to be used as an efficient antioxidant, they should allow ROS (e.g. $O_2^{\cdot-}$) to pass into the aqueous interior and interact with encapsulated SOD. Unfortunately, most liposomes or polymersomes have a low membrane permeability. The novelty of this study's therapy is in the utilization of nanoparticles that enable stable, yet efficient delivery of SOD. By doping diblock copolymer PEG-PPO into PEG-PBD polymersomes, the construct is able maintain the to harbor and retain the antioxidant enzyme within the nanoparticle while small molecules, such as free superoxide radicals, are able to pass through the permeable membrane of polymersomes.

As oxidative injury leads to both acute myocardial dysfunction as well as chronic LV dysfunction and adverse remodeling, the therapeutic efficacy of NP-SOD was assessed in both the acute and chronic stages using a I/R model. Acute injury three hours after I/R was measured via quantifying oxidative damage by ROS induced lipid peroxidation. NP-SOD-treated animals were able to scavenge free radical species more efficiently than those treated with PBS as measured by levels of the reactive aldehyde MDA. When comparing free SOD to PBS, however, no statistically significant treatment effect was observed. These subtleties became more evident as injury was analyzed from a macroscopic view. Histologic quantification of myocardial AAR not only demonstrated significantly greater myocardial preservation following administration of NP-SOD compared to PBS, it also showed that free SOD administration alone was, at best, equivalent to placebo injection. Ultimately, when assessing clinical utility, organ function is the most critical assessment of treatment effect; this study demonstrated a 17% improvement in EF in NP-SOD treated rats compared to the PBS group, while free SOD alone did not improve LV function over PBS.

In addition to attenuation of acute injury, NP-SOD also improved enzyme retention and bioavailability, likely owing to the protective quality of the polymersome construct against enzymatic degradation. Similar benefits have been observed in previous studies assessing carrier-based delivery systems.[22,38,39] As up to 50% of total permanent infarct in myocardial I/R is due to reperfusion itself, prolonged antioxidant availability and function using NP-SOD treatment are significant. This study demonstrated a reduction in collagen deposition, less fibrosis and preservation of functional myocardium in NP-SOD compared to saline alone at both cellular and whole-organ levels, while free SOD failed to replicate these treatment benefits. Importantly, these findings translated to significant improvement in chronic LV function in NP-SOD treated animals over those treated with saline or unencapsulated SOD.

Several studies have shown that ischemic preconditioning may be a reliable and effective method to reduce I/R injury;[40-42] however, its clinical utility is limited as the vast majority of PCI therapy for myocardial infarction occurs in the emergent, unplanned setting. Similarly, while direct intramyocardial administration is more invasive than catheter-based or peripherally delivered therapy, its use mitigates potential treatment variability related to targeting and absorption and raises the potential for undesired systemic consequences. Future studies in enhancing peripheral delivery may follow recent promising advancements using nanocarriers in cancer models,[43-45] or may rely upon alternative modalities such as bispecific antibody binding.[46] Until these modalities show the potential for clinical translatability, however, this study's treatment construct and delivery model provides the most direct and straightforward assessment of antioxidant-nanoparticle based therapy in an in vivo model of cardiac I/R injury.

This study has several limitations. One stems from the rapidity in which superoxide and other ROS are degraded, making direct in vivo quantification of ROS injury a challenge. In vitro data was relied upon to ensure that the enzyme of interest was functioning in an antioxidative capacity; this mirrored, although could not replicate, an in vivo model. Additionally, significant morbidity and mortality in I/R injury is caused by fatal arrhythmias,[47] as ROS generation itself impairs local electrophysiology by modifying proteins central to excitation-contraction coupling and altering myofilament sensitivity.[48] While this study assessed acute injury from mechanistic, histologic, and functional perspectives, it did not quantify injury at an electrophysiologic level. Procedural mortality was low, however, at 10% with two mortalities in the 28-day cohort (4.4%) occurring post-operatively. One death occurred after PBS injection and one after NP-SOD and may have been due to a number of different factors including fatal arrhythmia. Injection itself may further cause injury via disruption of already compromised microvasculature, which may represent a potential area requiring alternative therapy delivery modalities moving forward with preclinical translation.

3. Conclusion

This study provides a promising foundation for further development and assessment of a nanoparticle construct which delivers stabilized, bioavailable, exogeneous SOD. Described in this study is a therapeutic model which demonstrates the ability to utilize the potent antioxidative properties of SOD while preserving enzyme integrity within a semipermeable, amphiphilic diblock nanoparticle. The transience of SOD has been a long-standing deterrent to its exogeneous administration as a potential cardio-protectant in myocardial I/R injury. With this NP-SOD construct, the intent was to stabilize SOD function within the myocardium for extended durations. The findings observed here, particularly NP-SOD's ability to preserve LV native structure and function in both acute and chronic settings, warrant further investigation into the molecular, metabolomic and immunologic responses of the myocardium to NP-SOD treatment. Ongoing analysis will inform future therapeutic strategy in achieving clinical translatability.

4. Experimental Section/Methods

4.1. Animal Use

All experiments conformed to the National Institute of Health Guide for Care and Use of Laboratory Animals and were approved by the Institutional Animal Care and Use Committee of the University of Pennsylvania. *Rattus norvegicus* (Wistar) rats were obtained from Charles River Laboratories, Inc (Boston, MA).

4.2. Nanoparticle Construct

4.2.1. Materials

PEG-PBD and PEG-PPO were purchased from Polymer Source (Dorval, Quebec, Canada). IRDye 800CW NHS Ester was obtained from LI-COR, Inc. Calbiochem (EMD Millipore, Billerica, MA) provided Cu,Zn-Superoxide dismutase (MW 32500) from bovine erythrocytes. All other chemicals were used as received. All buffer solutions were prepared with deionized water.

4.2.2. Synthesis of Fluorescent Labeled SOD

IRDye 800CW-labeled SOD was prepared for retention assay and was synthesized utilizing a molar ratio of 2:1 of IRDye 800CW NHS Ester: SOD. For preparation, 1 mL 9.5 mg $mL^{-1}$ SOD (in 1 M sterile PBS) was mixed with 58.5 μL 10 mM IRDye 800CW NHS Ester (in anhydrous DMSO). After shaking at room temperature for 2 hours, unconjugated IRDye 800CW NHS Ester was removed by centrifugal filter devices (Amicon Ultra-4, 3000 MWCO, Millipore Corp.). The purified IRDye 800CW-labeled SOD was stored in darkness at 4° C.

4.2.3. Preparation of SOD-Encapsulated Porous Nanoparticles

Nanometer-sized porous polymersomes were prepared using the film hydration technique.[22] A 75 mol % PEG-PBD/25 mol % PEG-PPO mixture was prepared in chloroform in a glass vial using a total of 20 mg of PEG-PBD. The chloroform solvent was removed using a direct stream of nitrogen prior to vacuum desiccation overnight. After the formation of a dried film, 1 mL of 9.5 mg/mL SOD or IRDye 800CW-SOD in 1 M PBS (pH 7.4) was added to the dried polymer film. Samples were subjected to 5 freeze-thaw-vortex cycles in liquid nitrogen and warm $H_2O$ (55° C.), followed by extrusion 21 times through a 200 nm Nuclepore polycarbonate filter using a stainless-steel extruder (Avanti Polar Lipids). Nonentrapped SOD was removed via size exclusion chromatography using Sepharose CL-4B (Sigma-Aldrich). The sample was further purified and concentrated by centrifugal filter devices (Amicon Ultra-4, 100,000 MWCO, Millipore Corp.).

4.2.4. SOD Activity Measurement

SOD activity was measured using the ferricytochrome c assay.[49] Hypoxanthine (HX) and xanthine oxidase (XO) were used as a source of superoxide anion, while cytochrome c indicated scavenging of superoxide radical competing with SOD. Working solutions contained 50 mM phosphate buffer (pH 7.8), 0.1 EDTA, 50 μM HX, 20 μM cytochrome c and nanoparticle samples (before and after polymersome dissolution with Triton X-100). The reaction was initiated by the addition of XO (0.2 U/ml final concentration) and the absorbance was monitored at 550 nm using Synergy H1 hybrid multi-mode microplate reader (BioTek). One unit of SOD activity was defined as the amount of the enzyme which inhibited the rate of cytochrome c reduction by 50%. Differences in SOD activity before and after Triton X-100 treatment were determined using separate Student's t-tests for each formulation. The SOD encapsulation efficiency was calculated utilizing the following equation:

$$\text{Encapsulation efficiency (\%)} = (\text{Activity of SOD in the SOD NPs} / \text{Activity of SOD in feeding}) \times 100$$

4.2.5. Assessing Nanoparticle Morphology

The morphology of the NPs was imaged on a Tecnai-12 electron microscope. A drop of the samples were placed on a carbon coated 200-mesh copper grids for 2-3 minutes, then washed with water. The grids were stained with 2% phosphotungstic acid and analyzed at an acceleration voltage of 120 kV.

4.2.6. Instrumentation

DLS measurements were performed on a Zetasizer Nano from Malvern Instruments. The scattering angle was held constant at 90°. Fluorescence spectra measurements were done on a SPEX FluoroMax-3 spectrofluorometer (Horiba Jobin Yvon).

4.3. Cell Culture and In Vitro Analysis

4.3.1. In Vitro I/R Model

Embryonic *Rattus norvegicus* cell line, H9C2 cardiomyoblasts (ATCC® CRL-1446™) were cultured in Dulbecco's Modified Eagle Medium (DMEM) supplemented with 10% Fetal Bovine Serum (FBS). Cells were maintained in a humidified incubator at 37° C. (21% $O_2$/5% $CO_2$) and utilized for experiments from passages 2-8. Ischemia-reperfusion injury was modeled by exposure to hypoxia (0.5% $O_2$/5% $CO_2$/95% $N_2$/37° C.) for 60 mins before treatment administration and return to normoxia (21% $O_2$/5% $CO_2$/74% $N_2$/37° C.). For in vitro experiments, 10 U of free SOD or NP-SOD dissolved in cell culture grade distilled water was administered for every 25,000 cells.

4.3.2. ROS Quantification In Vitro

H9C2 cells were seeded in black-wall, clear bottom 96-well plates at a density of 25,000 cells per well and allowed to adhere overnight. Ischemia was induced for one hour before administration of either PBS, empty NP, free SOD or NP-SOD and reperfusion in normoxic conditions. A 20 mM stock solution of $H_2$DCFDA was dissolved in anhydrous DMSO and stored at −20° C. for up to one week. A final concentration of 20 μM $H_2$DCFDA was dissolved immediately prior to use in sterile PBS and added to each well for a 20 min incubation at room temperature in the dark. The $H_2$DCFDA solution was aspirated and replaced with sterile PBS before reading the fluorescence intensity on the Nexcelom Celigo Cell Image Cytometer (Ex/Em: 485 nm/535 nm).

4.3.3. JC-1 Mitochondrial Membrane Staining

In multi-well chamber slides, H9C2 cells were seeded at a density of 50,000 cells per chamber and incubated in growth media overnight. Cells were then placed into either hypoxic or normoxic conditions for 1 hour before administration of PBS, empty NP, free SOD or NP-SOD. Slides were then returned to normoxia for 3 hours of reperfusion and stained with 10 μg/mL JC-1 working solution (Abcam) for 10 min in the dark at room temperature. Slides were then washed with PBS and mounted with Vectashield DAPI conjugated mounting medium and imaged on a Leica Fluorescence microscope. The intensity of JC-1 aggregate (Ex/Em: 535 nm/595 nm) and monomer (Ex/Em: 485 nm/535 nm) intensities were then quantified with ImageJ.

4.3.4. Cellular Cytotoxicity and Viability

H9C2 cells in cell culture medium were seeded at a density of 10,000 cells per well before incubation with 20 μL of the specified treatment at 21% $O_2$/5% $CO_2$. To assess cytotoxicity, samples of culture media from each treatment group were harvested in a time-dependent fashion and diluted 1:100 in LDH Storage Buffer. Samples and standards were incubated in equivolume LDH Detection Reagent and Reductase for 60 minutes according to supplier instructions before luminescence was recorded (Promega LDH-Glo). Viability was assessed after incubating treated cells with 10 μL of 12 mM Vybrant MTT (Invitrogen) for 4 hours at 37° C. Culture media was then removed after 24 hours and formazin crystals were dissolved using DMSO. Absorbance at 540 nm was measured.

4.4. In Vivo Analysis 4.4.1. In Vivo I/R Model

A rat model of myocardial I/R injury was used to study the efficacy of NP-SOD in vivo. General anesthesia was induced with 5% isoflurane, after which rats were endotracheally intubated with a 16-gauge angiocatheter and mechanically ventilated. Confirmation of anesthesia to a surgical plane was confirmed by absence of palpebral and pedal reflex. Isoflurane was maintained at 1-3% intraoperatively. Subcutaneous injections of 0.05 mg/kg buprenorphine were administered for analgesia. After positioning in right lateral decubitus position, a left sided thoracotomy was performed via the fourth interspace and the pericardium was opened. The left anterior descending artery was then exposed and suture ligated 1 mm below the left atrial appendage with a 7-0 polypropylene suture, creating an anterolateral infarction encompassing 30-40% of the LV. Ischemia was maintained for 60 minutes as described previously.[50] At 60 minutes, five separate 20 μL intramyocardial injections of selected treatment (100 μL total) were administered circumferentially along the 'border zone' of perfused and non-perfused tissue. The ligation was then relieved immediately after intramyocardial injection with treatment modalities, allowing for reperfusion. The chest was then closed in three layers, analgesia administered through 1 mg/kg intercostal bupivacaine and 2 mg/kg subcutaneous meloxicam injections and the animal recovered. When applicable, an additional group of sham surgery subjects underwent thoracotomy alone without ligation or injection.

4.4.2. Confirmation of I/R Injury by Plasma Troponin I Concentration

Whole blood was collected before ligation and 3 hours post reperfusion in heparinized tubes and centrifuged at 2500×g for 15 minutes at 4° C. Plasma was separated out and stored at −80° C. Troponin I ELISA (Abcam) was then conducted with samples prepared according to instructions for quantification of plasma troponin I. Samples with elevation of plasma troponin I above 20,000 pg/mL were confirmed to have myocardial I/R injury.

4.4.3. In Vivo SOD Retention

Using the in vivo I/R model described above, intramyocardial enzyme retention was assessed using fluorescent-labeled SOD. IRDye 800CW fluorophore (10 mM) was conjugated to SOD [500 U/mL] and injected into the myocardium as either free or nanoparticle-encapsulated enzyme. Hearts were explanted in a time-course fashion at 15-minutes, 24- and 72-hours post injection (n=4 per group per timepoint). Imaging was performed with near-IR IVIS microscopy (Spectrum, Ex/Em 760 nm/800 nm), and retention quantified by proportional radiant efficiency [p/s/cm$^2$/sr]/[μW/cm$^2$] of the region of interest (ROI) to that of baseline after subtracting background signal.

4.4.4. Assessing In Vivo Therapeutic Efficacy

Subjects were divided into four treatment groups to assess for therapeutic efficacy. Again using the in vivo I/R injury model, animals received intramyocardial injections of 1) free SOD [500 U/mL], 2) NP-SOD [500 U/mL], 3) PBS or 4) sham surgery alone. Analyses were performed at 3 hours to measure the extent of acute injury and 28 days to assess chronic ventricular remodeling.

4.4.5. Measuring LV Hemodynamic Function

LV function was measured 3 hours post reperfusion. They were re-induced with 5% isoflurane. After endotracheal intubation and mechanical ventilation, rats were placed in supine position and isoflurane decreased to 1-3% to maintain adequate sedation. EF was then measured by transthoracic echocardiography (Philips SONOS 5500). Ventricular function was assessed in the parasternal short-axis view at the ventricular base, mid-papillary region and apex, as well as in parasternal long-axis.

LV function was assessed 28 days after the initial operation in the same manner. These data are represented as the average of individual mid-papillary and apical EF measurements, taken in triplicate. Following echocardiography recordings, the right neck was dissected, and the right common carotid artery exposed. A 2-Fr pressure-conductance catheter (Millar, Inc., Houston, TX) was then passed in retrograde fashion into the LV through an arteriotomy in the right common carotid artery. Primary hemodynamic measurements assessed preload-independent contractility through ESPVR. This was obtained by measuring the slope of end-systole during occlusion of the IVC.[51] Additional hemodynamic parameters measured were EF, cardiac output, stroke volume, stroke work, and heart rate.

4.4.6. Histologic Quantification

Following terminal hemodynamic measures, hearts were explanted, washed with sterile PBS and prepared for further analysis. Hearts assessed 3 hours post-surgery were filled at −25° C. for 5 minutes and sectioned into 2 mm slices. Alternating 2 mm sections were stained with TTC for 20 minutes at 37° C. and fixed with 4% paraformaldehyde. Sections were photographed and the injured area at risk was assessed by quantifying the relative area of white (unstained, non-perfused) to red (stained, perfused) myocardium using ImageJ. Remaining sections were flash frozen for future analysis.

For animals assessed 28 days post-surgery, hearts were filled and frozen in OCT at −80° C. Utilizing a Leica CM3050S Cryostat, 10 mm sections were obtained and mounted for histological analysis. Hearts were stained with Masson's Trichrome Stain (Sigma Aldrich) and the area of gross left ventricular scar represented as Aniline Blue positive myocardial fibrosis was quantified using ImageJ. Picrosirius Red (Abcam) was administered to frozen sections for 1 hour and dehydrated as previously described[52] before quantification of LV area containing collagen deposits using ImageJ. Additional 10 μM cryosections were fixed in 4% paraformaldehyde and stained for one minute in both Mayer's Hematoxylin and Eosin (H&E) before dehydration with ethanol and xylene. Slides were mounted and imaged in bright field across the length of the left ventricle and septum.

4.4.7. Lipid Peroxidation Quantification

MDA is an end product of ROS induced lipid peroxidation.[53] Frozen myocardial tissue was lysed in MDA extraction buffer with butylated hydroxytoluene and precipitated with TBA according to instructions (Abcam). Samples and standards were heated at 95° C. for 1 hour. Samples were then transferred to a 96 well plate and absorbance was recorded at OD 532 nm in the BioTek Gen5 Synergy 2 plate reader.

4.5. Statistical Analysis

Treatment across groups was randomly generated and subjects identified with random identifiers. Investigators were blinded to treatment during both data acquisition and analysis. Unless otherwise specified, all analyses are represented as mean+/−standard error of the mean (SEM). Comparisons across groups utilized one-way analysis of variance (ANOVA), while individual comparisons between groups were performed using Tukey's honestly significant difference test. P-values of <0.05 were considered significant. Data analysis was performed using GraphPad Prism 9.0 (GraphPad Software, Inc., San Diego, CA). Error bars on all plots represent mean+/−SEM.

REFERENCES

1. G. A. Roth, C. Johnson, A. Abajobir, F. Abd-Allah, S. F. Abera, A. Gebre, M. Ahmed, B. Aksut, T. Alam, K. Alam, F. Alla, N. Alvis-Guzman, S. Amrock, H. Ansari, J. Amlov, et al. Global, Regional, and National Burden of Cardiovascular Diseases for 10 Causes, 1990 to 2015. *J Am Coll Cardiol.* 2017; 70(1):1-25.
2. M. A. Khan, M. J. Hashim, H. Mustafa, M. Y. Baniyas, S. K. B. M. A. Suwaidi, R. AlKatheeri, F. M. K. Alblooshi, M. E. A. H. Almatrooshi, M. E. H. Alzaabi, R. S. A. Darmaki, S. N. A. H. Lootah. Global Epidemiology of Ischemic Heart Disease: Results from the Global Burden of Disease Study. *Cureus.* 2020; 12(7):e9349.
3. M. R. Law, H. C. Watt, N. J. Wald. The underlying risk of death after myocardial infarction in the absence of treatment. *Arch Intern Med.* 2002; 162(21):2405-2410.
4. V. Braunersreuther, V. Jaquet. Reactive Oxygen Species in Myocardial Reperfusion Injury: From Physiopathology to Therapeutic Approaches. *Curr Pharm Biotechnol.* 2011; 13(1):97-114.
5. Q. Yang, G. W. He, M. J. Underwood, C. M. Yu. Cellular and molecular mechanisms of endothelial ischemia/reperfusion injury: Perspectives and implications for postischemic myocardial protection. *Am J Transl Res.* 2016; 8(2):765-777.
6. S. Cadenas. ROS and redox signaling in myocardial ischemia-reperfusion injury and cardioprotection. *Free Radic Biol Med.* 2018; 117:76-89.
7. A. Görlach, K. Bertram, S. Hudecova, O. Krizanova. Calcium and ROS: A mutual interplay. Redox Biol. 2015; 6:260-271.
8. N. M. Scherer, D. W. Deamer. Oxidative stress impairs the function of sarcoplasmic reticulum by oxidation of sulfhydryl groups in the Ca2+-ATPase. *Arch Biochem Biophys.* 1986; 246(2):589-601.
9. C. Batandier, X. Leverve, E. Fontaine. Opening of the mitochondrial permeability transition pore induces reactive oxygen species production at the level of the respiratory chain complex I. *J Biol Chem,* 2004; 279(17), 17197-17204.
10. J. Jacobson, M. R. Duchen. Mitochondrial oxidative stress and cell death in astrocytes-requirement for stored Ca2+ and sustained opening of the permeability transition pore. *J Cell Sci.* 2002; 115(6), 1175-1188.
11. K. Odagiri, H. Katoh, H. Kawashima, T. Tanaka, H. Ohtani, M. Saotome, T. Urushida, H. Satoh, H. Hayashi. Local control of mitochondrial membrane potential, permeability transition pore and reactive oxygen species by calcium and calmodulin in rat ventricular myocytes. *J Mol Cell Cardiol.* 2009; 46(6), 989-997.
12. M. J. Perez, R. A. Quintanilla. Development or disease: duality of the mitochondrial permeability transition pore. *Dev Biol.* 2017; 426(1), 1-7.
13. H. M. Piper. Energy deficiency, calcium overload or oxidative stress: possible causes of irreversible ischemic myocardial injury. *Klin Wochenschr.* 1989; 67(9), 465-476.
14. F. Arslan, R. C. Lai, M. B. Smeets, L. Akeroyd, C. Andre, E. N. E. Aguor, L. Timmers, H. V. van Rijen, P. A. Doevendans, G. Pasterkamp, S. K. Lim, D. P. de Kleijn. Mesenchymal stem cell-derived exosomes increase ATP levels, decrease oxidative stress and activate PI3K/Akt pathway to enhance myocardial viability and prevent adverse remodeling after myocardial ischemia/reperfusion injury. *Stem Cell Res.* 2013; 10(3), 301-312.
15. H. P. Grill, J. L. Zweier, P. Kuppusamy, M. L. Weisfeldt, J. T. Flaherty. Direct Measurement of Myocardial Free Radical Generation in an In Vivo Model: effects of Postischemic Reperfusion and Treatment With Human Recombinant Superoxide Dismutase. *J Am Coll Cardiol.* 1992; 20:1604-11.
16. B. A. Omar, J. M. McCord. Interstitial equilibration of superoxide dismutase correlates with its protective effect in the isolated rabbit heart. *J Mol Cell Cardiol.* 1991; 23(2):149-159.
17. J. Liu, J. Hou, Z. Y. Xia, W. Zeng, X. Wang, R. Li, C. Ke, J. Xu, S. Lei, Z. Xia. Recombinant PTD-Cu/Zn SOD attenuates hypoxia-reoxygenation injury in cardiomyocytes. *Free Radic Res.* 2013; 47(5):386-93.
18. P. Wang, H. Chen, H. Qin, S. Sankarapandi, M. W. Becher, P. C. Wong, J. L. Zweier. Overexpression of human copper,zinc-superoxide dismutase (SOD1) prevents postischemic injury. *Proc Natl Acad Sci USA.* 1998; 95(8):4556-4560.
19. M. Tanaka, R. C. Stoler, G. P. FitzHarris, R. B. Jennings, K. A. Reimer. Evidence against the "early protection-delayed death" hypothesis of superoxide dismutase therapy in experimental myocardial infarction. Polyethylene glycol-superoxide dismutase plus catalase does not limit myocardial infarct size in dogs. *Circ Res.* 1990; 67(3):636-644.

20. J. T. Flaherty, B. Pitt, J. W. Gruber, R. R. Heuser, D. A. Rothbaum, L. R. Burwell, B. S. George, D. J. Kereiakes, D. Deitchman, N. Gustafson. Recombinant human superoxide dismutase (h-SOD) fails to improve recovery of ventricular function in patients undergoing coronary angioplasty for acute myocardial infarction. *Circulation.* 1994; 89(5):1982-1991.
21. S. Kabu, Y. Gao, B. K. Kwon, V. Labhasetwar. Drug delivery, cell-based therapies, and tissue engineering approaches for spinal cord injury. *J Control Release.* 2015; 219:141-154.
22. E. Hood, E. Simone, P. Wattamwar, T. Dziubla, V. Muzykantov. Nanocarriers for vascular delivery of antioxidants. *Nanomedicine.* 2011; 6(7):1257-1272.
23. A. Salvador, J. Sousa, R. E. Pinto. Hydroperoxyl, superoxide and pH gradients in the mitochondrial matrix: A theoretical assessment. *Free Radic Biol Med.* 2001; 31(10):1208-1215.
24. S. Kartha, L. Yan, C. L. Weisshaar, M. E. Ita, V. V. Shuvaev, V. R. Muzykantov, A. Tsourkas, B. A. Winkelstein, Z. Cheng. Superoxide Dismutase-Loaded Porous Polymersomes as Highly Efficient Antioxidants for Treating Neuropathic Pain. *Adv Healthc Mater.* 2017; 6(17): 1-6.
25. M. K. Reddy, L. Wu, W. Kou, A. Ghorpade, V. Labhasetwar. Superoxide dismutase-loaded PLGA nanoparticles protect cultured human neurons under oxidative stress. *Appl Biochem Biotechnol.* 2008; 151(2-3):565-577
26. O. Rajkovic, C. Gourmel, R. d'Arcy, R. Wong, I. Rajkovic, N. Tirelli, E. Pinteaux. Reactive Oxygen Species-Responsive Nanoparticles for the Treatment of Ischemic Stroke. *Adv Ther* (*Weinh*). 2019; 2(7):1900038
27. X. Zhou, J. Lv, G. Li, T. Qian, H. Jiang, J. Xu, Y. Cheng, J. Hong. Rescue the retina after the ischemic injury by polymer-mediated intracellular superoxide dismutase delivery. *Biomaterials.* 2021; 268:120600.
28. D. Ni, H. Wei, W. Chen, Q. Bao, Z. T. Rosenkrans, T. E. Barnhart, C. A. Ferreira, Y. Wang, H. Yao, T. Sun, D. Jiang, S. Li, T. Cao, Z. Liu, J. W. Engle, et al. Ceria Nanoparticles Meet Hepatic Ischemia-Reperfusion Injury: The Perfect Imperfection. *Adv Mater.* 2019; 31(40):e1902956.
29. S. J. Han, R. M. Williams, V. D'Agati, E. A. Jaimes, D. A. Heller, H. T. Lee. Selective nanoparticle-mediated targeting of renal tubular Toll-like receptor 9 attenuates ischemic acute kidney injury. *Kidney Int.* 2020; 98(1):76-87.
30. L. G. Chi, Y. Tamura, P. T. Hoff, M. *Macha*, K. P. Gallagher, M. A. Schork, B. R. Lucchesi. Effect of superoxide dismutase on myocardial infarct size in the canine heart after 6 hours of regional ischemia and reperfusion: a demonstration of myocardial salvage. *Circ Res.* 1989; 64(4):665-675.
31. G. Seshadri, J. C. Sy, M. Brown, S. Dikalov, S. C. Yang, N. Murthy, M. E. Davis. The delivery of superoxide dismutase encapsulated in polyketal microparticles to rat myocardium and protection from myocardial ischemia-reperfusion injury. *Biomaterials.* 2010; 31(6):1372-1379.
32. A. Uraizee, K. A. Reimer, C. E. Murry, R. B. Jennings. Failure of superoxide dismutase to limit size of myocardial infarction after 40 minutes of ischemia and 4 days of reperfusion in dogs. *Circulation.* 1987; 75(6):1237-1248.
33. D. C. Salo, R. E. Pacifici, S. W. Lin, C. Giulivi, K. J. Davies. Superoxide dismutase undergoes proteolysis and fragmentation following oxidative modification and inactivation. *J Biol Chem.* 1990; 265(20):11919-11927.
34. M. Luisa Corvo, J. C. Jorge, R. van't Hof, M. E. Cruz, D. J. Crommelin, G. Storm. Superoxide dismutase entrapped in long-circulating liposomes: formulation design and therapeutic activity in rat adjuvant arthritis. *Biochim Biophys Acta.* 2002; 1564(1):227-236.
35. Z. Li, F. Wang, S. Roy, C. K. Sen, J. Guan. Injectable, highly flexible, and thermosensitive hydrogels capable of delivering superoxide dismutase. *Biomacromolecules.* 2009; 10(12):3306-3316.
36. S. Bae, M. Park, C. Kang, S. Dilmen, T. H. Kang, D. G. Kang, Q. Ke, S. U. Lee, D. Lee, P. M. Kang. Hydrogen Peroxide-Responsive Nanoparticle Reduces Myocardial Ischemia/Reperfusion Injury. *J Am Heart Assoc.* 2016; 5(11):e003697.
37. K. Nagaoka, T. Matoba T, Y. Mao, Y. Nakano, G. Ikeda, S. Egusa, M. Tokutome, R. Nagahama, K. Nakano, K. Sunagawa, K. Egashira. A New Therapeutic Modality for Acute Myocardial Infarction: Nanoparticle-Mediated Delivery of Pitavastatin Induces Cardioprotection from Ischemia-Reperfusion Injury via Activation of PI3K/Akt Pathway and Anti-Inflammation in a Rat Model. *PLoS One.* 2015; 10(7):e0132451.
38. B. B. Youan. Microencapsulation of superoxide dismutase into biodegradable microparticles by spray-drying. *Drug Deliv.* 2004; 11(3):209-214.
39. S. Su, P. M. Kang. Systemic Review of Biodegradable Nanomaterials in Nanomedicine. *Nanomaterials* (*Basel*). 2020; 10(4):656.
40. S. Dong, Y. Cao, H. Li, J. Tian, C. Yi, W. Sang. Impact of ischemic preconditioning on ischemia-reperfusion injury of the rat sciatic nerve. *Int J Clin Exp* Med. 2015; 8(9):16245-16251.
41. M. Donato, P. Evelson, R. J. Gelpi. Protecting the heart from ischemia/reperfusion injury: an update on remote ischemic preconditioning and postconditioning. *Curr Opin Cardiol.* 2017; 32(6):784-790.
42. S. P. Loukogeorgakis, A. T. Panagiotidou, M. W. Broadhead, A. Donald, J. E. Deanfield, R. J. MacAllister. Remote ischemic preconditioning provides early and late protection against endothelial ischemia-reperfusion injury in humans: role of the autonomic nervous system. *J Am Coll Cardiol.* 2005; 46(3):450-456.
43. D. A. Bölükbas, S. Datz, C. Meyer-Schwickerath, C. Morrone, A. Doryab, D. Gößl, M. Vreka, L. Yang, C. Arygo, S. H. van Rijt, M. Lindner, O. Eickelberg, T. Stoeger, O. Schmid, S. Lindstedt, et al. Organ-Restricted Vascular Delivery of Nanoparticles for Lung Cancer Therapy. *Adv Ther* (*Weinh*). 2020; 3(7):2000017.
44. S. Hossen, M. K. Hossain, M. K. Basher, M. N. H. Mia, M. T. Rahman, M. J. Uddin. Smart nanocarrier-based drug delivery systems for cancer therapy and toxicity studies: A review. *J Adv Res.* 2019; 15:1-18.
45. D. Rosenblum, N. Joshi, W. Tao, J. M. Karp, D. Peer. Progress and challenges towards targeted delivery of cancer therapeutics. *Nat Commun.* 2018; 12; 9(1):1410.
46. K. Huang, Z. Li, T. Su, D. Shen, S. Hu, K. Cheng. Bispecific Antibody Therapy for Effective Cardiac Repair through Redirection of Endogenous Stem Cells. *Adv Ther* (*Weinh*). 2019; 2(10):1900009.
47. D. M. Yellon, D. J. Hausenloy. Myocardial reperfusion injury. *N Engl J Med.* 2007; 357(11):1121-1135.

48. E. Takimoto, D. A. Kass. Role of oxidative stress in cardiac hypertrophy and remodeling. *Hypertension.* 2007; 49:241-248.
49. J. M. McCord, I. Fridovich. Superoxide dismutase an enzymic function for erythrocuprein (hemocuprein). *J Biol Chem.* 1969; 244(22): 6049-6055.
50. B. He, J. Xiao, A. J. Ren, Y. F. Zhang, H. Zhang, M. Chen, B. Xie, X. G. Gao, Y. W. Wang. Role of miR-1 and miR-133a in myocardial ischemic postconditioning. *J Biomed Sci.* 2011; 18(1):22.
51. P. Pacher, T. Nagayama, P. Mukhopadhyay, S. Bátkai, D. A. Kass. Measurement of cardiac function using pressure-volume conductance catheter technique in mice and rats. *Nat Protoc.* 2008; 3(9):1422-1434.
52. R. Lattouf, R. Younes, D. Lutomski, N. Naaman, G. Godeau, K. Senni, S. Changotade. Picrosirius Red Staining: A Useful Tool to Appraise Collagen Networks in Normal and Pathological Tissues. *J Histochem Cytochem.* 2014; 62(10):751-758.
53. D. Tsikas. Assessment of lipid peroxidation by measuring malondialdehyde (MDA) and relatives in biological samples: Analytical and biological challenges. *Anal Biochem.* 2017; 524:13-30.

Exemplary Disclosure—Osteoarthritis

Oxidative stress and the reactive oxygen species (ROS) have important roles in osteoarthritis (OA) development and progression. Scavenging ROS by exogenous antioxidant enzymes could be a promising approach for OA treatment. However, the direct use of antioxidant enzymes, such as superoxide dismutase (SOD), is challenging due to a lack of effective drug delivery system to knee joints. This study utilized a highly efficient antioxidative nanoparticle based on SOD-loaded porous polymersome nanoparticles (SOD-NPs) for delivery of SOD to mouse knee joints. Intra-articularly injected SOD-NPs had prolonged joint retention time with predominant accumulation in synovium but not in articular cartilage. Examining human tissue explants revealed that SOD-NPs minimize oxidative damages on synovium from OA-like insults. Intra-articular injections of SOD-NPs in mice receiving OA surgery were effective in attenuating OA initiation and preventing its further progression. Mechanistically, SOD-NPs reduced ROS production and the synthesis of catabolic proteases in both articular cartilage and synovium tissues. Hence, our work demonstrates the therapeutic potential of SOD-NPs and indicate that targeting synovium holds a great promise for OA therapy.

1. Introduction

Knee osteoarthritis (OA) is a painful and debilitating musculoskeletal disease that can result in chronic joint pain, loss of joint function, and deleterious effects on the quality of daily life.[1] Current treatments for OA include non-pharmacological management, pharmacological treatments, and surgical approaches.[2, 3] Although many pharmacologic treatments have been explored, there are no disease-modifying therapies available to delay OA progression or reverse the disease.[4] In most cases, pharmacological treatments are only palliative and accompanied by adverse side effects. Due to a lack of effective treatment approaches, over 600,000 knee replacements are performed each year in the US.[5] Currently, most drug studies aim to directly target articular cartilage for restoration of its integrity. Since OA is a whole joint disease, it is important to explore whether targeting other joint tissues, such as synovium, could be an effective OA treatment.

Previous studies demonstrated the critical role of oxidative stress and reactive oxygen species (ROS) in OA via regulating matrix metalloproteinase (MMP) production, chondrocyte apoptosis and senescence, extracellular matrix synthesis and degradation.[6-10] Under healthy conditions, ROS are produced at low levels in joint tissues. The adverse effects of ROS are normally blocked by the body's natural antioxidant defense system, including enzymatic and non-enzymatic antioxidants.[11] However, under OA pathological conditions, the balance between antioxidants and ROS is disrupted due to depletion of antioxidants, excess accumulation of ROS, or both, in cartilage and synovium.[6] This imbalance of cellular redox results in oxidative stress and damage in chondrocytes, leading to cartilage degradation.

Among multiple types of endogenous and exogenous antioxidants, such as phytochemicals, vitamins, and enzymes,[12] superoxide dismutase (SOD), is the major catalytic antioxidant in joint tissues.[13, 14] SOD catalyzes the conversion of superoxide radical ($O_2^{\cdot-}$) to hydrogen peroxide ($H_2O_2$). Previous studies showed that SOD activity is significantly decreased in OA joint tissues.[15-17] Several pilot trials have been performed by intraarticular injection of SOD into knee joint of patients suffering from active OA.[18, 19] Thus, scavenging ROS by exogenous SOD could be a potential therapeutic strategy for OA treatment. However, the results of animal and clinical studies indicate that the direct use of free SOD only afford modest protective effect against oxidative damage due to intrinsic properties of SOD, namely, inadequate retention at the disease site and rapid inactivation of native SOD.[20] Therefore, developing an effective delivery system that improves SOD joint retention and protects against degradation could represent a new direction for OA therapy.

Nanomedicine is increasingly being used to improve therapeutic delivery for OA treatment due to the favorable pharmacokinetics, biodistribution, and solubility of nanoparticles (NPs) compared with free drugs.[21-24] Many NPs have recently been explored as carriers for SOD, including liposomes,[25] poly(lactide-co-glycolide) (PLGA),[26] hollow silica nanospheres,[27] and polymersomes.[28] However, most of these NPs possess notable limitations in terms of SOD delivery. For example, encapsulated SOD within liposomes exhibit improved protection against degradation, but suffers from loss of enzyme function and accessibility to ROS due to the absence of particle permeability.[29] PLGA-based NP systems are often associated with a poor drug loading for hydrophilic drugs, high burst release, and difficulties for surface functionalization.[30, 31]

Polymersomes are a class of vesicles made from amphiphilic synthetic block copolymers that exhibit improved stability and a long in vivo retention time compared with phospholipid liposomes.[32, 33] In order for antioxidant enzyme-loaded polymersomes to be used as an efficient NP-based antioxidant, they should allow ROS, e.g. $O_2^{\cdot-}$ to pass into the aqueous interior and interact with encapsulated enzyme. Unfortunately, most polymersomes have a low intrinsic membrane permeability.[32] To overcome this challenge, we developed porous polymersomes with improved membrane permeability for small molecules.[34, 35] By loading SOD into porous polymersomes, these SOD-NPs have showed beneficial effects in treating neurologic injury and myocardial ischemic reperfusion injury.[34, 35] In this study, these constructs were characterized for their behavior in joint tissues and investigated for their treatment effects in preventing and rescuing OA using a small animal model. To our surprise, we found that SOD- NPs mainly target synovium, but not articular cartilage, to achieve their therapeutic actions.

2. Materials and Methods

2.1. Materials

Poly(ethylene glycol) (900)-polybutadiene (1800) copolymer (denoted PEG-PBD, MW 2700 Da) and Poly(ethylene glycol) (450)-poly(propylene oxide) (1400) (denoted PEG-PPO, MW 1850 Da) were purchased from Polymer Source (Dorval, Quebec, Canada). 1,2-dioleoyl-sn-glycero-3-phosphoethanolamine-N-(Lissamine rhodamine B sulfonyl) (Rhod-PE) was purchased from Avanti Polar Lipids, Inc. Cu/Zn Superoxide dismutase (SOD; MW 32500) from bovine erythrocytes was from Calbiochem (EMD Millipore, Billerica, MA). Fluorescein isothiocyanate (FITC) was purchased from Thermo Fisher Scientific. IRDye 800CW NHS Ester was purchased from LI-COR, Inc. All other chemicals were used as received. All of the buffer solutions were prepared with deionized water.

2.2. Synthesis of Fluorescent Labeled SOD

FITC-labeled SOD (FITC-SOD) was synthesized utilizing a molar ratio of 1/20 of SOD/FITC. Specifically, 1 mL 9.5 mg/mL SOD (in 10 mM PBS, pH 7.4)) was mixed with 455.31 μL 12.84 mM FITC (in anhydrous DMSO). After shaking at room temperature for 2 h, unconjugated FITC was removed by PD-10 column.

IRDye 800CW-labeled SOD (IRDye 800CW-SOD) was synthesized using a molar ratio of 1/10 of SOD/IRDye 800CW NHS Ester. Specifically, 1 mL 9.5 mg/mL SOD (in 10 mM PBS) was mixed with 58.5 μL 10 mM IRDye 800CW NHS Ester (in anhydrous DMSO). After shaking at room temperature for 2 h, unconjugated IRDye 800CW was removed by PD-10 column.

2.3. Synthesis and Characterization of SOD-Loaded Nanoparticles

Briefly, stock solutions of PEG-PBD and PEG-PPO in chloroform were mixed in the following molar ratios: PEG-PBD/PEG-PPO (75:25). The total amount of PEG-PBD for each of the polymersome compositions was 20 mg. The solvent was removed using a direct stream of nitrogen prior to vacuum desiccation for at least 4 hours. 1 mL of 10 mg/mL SOD in 10 mM PBS (pH 7.4) was added to dried polymer films. Subsequently, the samples were incubated in a 55° C. water bath for 10 minutes and then sonicated for another 5 minutes. Samples were subjected to 5 freeze-thaw cycles in liquid nitrogen and warm $H_2O$ (55° C.), followed by extrusion for at least 11 times through two stacked 200 nm Nuclepore polycarbonate filters using a mini extruder (Avanti Polar Lipids). After that, the sample was purified to remove nonentrapped SOD by centrifugal filter devices (Amicon Ultra-4, 100,000 MWCO, Millipore Corp.).

To prepare dual fluorescent dyes-labeled nanoparticles, 1 mL of 9.5 mg/mL FITC-SOD or IRDye 800CW-SOD was added to the dried polymer doped with 5 mol % Rhod-PE and freeze-thaw and extrusion were performed as described above. The nonentrapped FITC-SOD or IRDye 800CW-SOD was removed via size exclusion chromatography using Sepharose CL-4B (Sigma-Aldrich) and rehydration buffer as the eluent.

The measurement of SOD activity using the cytochrome c assay has been detailed previously.[34, 36] The diameter and size distribution of nanoparticles were measured with dynamic light scattering (DLS, Malvern, Zetasizer, Nano-ZS). Ultraviolet-visible spectra (UV-Vis) and fluorescence spectra measurements were made on a Cary 100 spectrophotometer (Varian) and a SPEX FluoroMax-3 spectrofluorometer (Horiba Jobin Yvon).

For stability assay, SOD-NPs were stored in 10 mM PBS (pH 7.4) at 4° C. Measurement of nanoparticle structural integrity was acquired by monitoring the hydrodynamic diameter over the course of one week by dynamic light scattering (DLS). In addition, in vitro stability of SOD-NPs was also measured by DLS in 50% bovine synovial fluid (Vendors, Lampire biological laboratories, Inc.) at 37° C. for 24 hours. The stability of SOD-NPs was tested in triplicate.

2.4. Cell Culture

Primary mouse chondrocytes were isolated from the distal femoral of P3 (3 days after birth) C57Bl/6 mice as described previously with minor modification.[37] Briefly, cartilage tissues were incubated with 0.25% trypsin-EDTA (Invitrogen) for 30 min, followed by 600 U/mL type I collagenase (Worthington Biochemical) for 2 h. Primary mouse synovial fibroblasts (SFs) were isolated from joints of 2-month-old C57Bl/6 mice as described previously with minor modification. [38] Briefly, after euthanasia, mouse knee joints were harvested and washed with ice-cold PBS, then the joint capsule was opened by reversing the quadricep, after that, the synovium tissues were carefully dissected under the microscopy. Synovial tissues were then digested with 0.25% trypsin-EDTA for 30 min, followed by 300 U/mL type I collagenase digestion for 30 min. After filtered through a 70 μm strainer (Fisher Scientific), cells were cultured in growth medium (DMEM/F12 with 10% FBS, 100 μg/mL streptomycin, and 100 U/mL penicillin) to confluency.

For cell viability study, primary chondrocytes were seeded in 96-well plates at 5000 cells/well overnight, followed by SOD-NPs treatment (15.625 to 500 U/mL) for 24 h. 3-(4,5-dimethylthiazol-2-yl)-5-(3-carboxymethoxyphenyl)-2-(4-sulfophenyl)-2H-tetrazolium) (MTS) cell proliferation assay (Thermo Fisher Scientific) was then performed on these cells. The absorbance of formazan product was measured on a Tecan microplate reader (BioTek Instruments, Inc.) at 490 nm. Cell viability was calculated using the following equation:

$$\text{Cell viability (\%)}=\text{Absorbance sample}/(\text{Absorbance control})\times 100$$

For uptake assay, SFs were seeded in 24-well plate for 24 h at 5000 cells/well and then treated with SOD(FITC)-NP (Rhod) for another 24 h at 37° C. and 5% $CO_2$. The final FITC concentration in the culture medium was 10 μM. Cells were mounted with DAPI Fluoromount-G Mounting Medium (Southern Biotech) and observed under confocal microscope (Zeiss LSM 710). For intracellular ROS detection, SFs were treated with PBS (Untreated), TNFα (GenScript) in combination with PBS, empty NP, free SOD or SOD-NPs for 24 h, followed by 10 μM $H_2$DCFDA incubation (Medchem express HY-D0940) in the dark for 30 min at 37° C. Cells were detached from the dish by 0.05% trypsin-EDTA and immediately analyzed by flow cytometer (BD Biosciences, LSR II).

2.5. Animal Care and OA Surgery

All animal work performed in this study was approved by the Institutional Animal Care and Use Committee at the University of Pennsylvania. To induce mouse OA, 3-month-old C57BL/6 male mice were subjected to DMM surgery at right knees and sham surgery at left knees as described previously.[37] Briefly, in DMM surgery, the joint capsule was opened under anesthesia and the medial meniscotibial ligament was cut to destabilize the meniscus without damaging other tissues. In Sham surgery, the joint capsule was opened in the same fashion but without any further damage. To test the therapeutic effect of free SOD or SOD-NPs, 10 μl PBS, empty NPs, free SOD (500 U/mL) or SOD-NPs (500 U/mL) was injected intra-articularly with a 30-gauge needle into mouse right knees. The first injection was performed immediately after surgery or 4 weeks after the surgery. Injections were then repeated once every 2 weeks until 12 weeks after the DMM surgery.

2.6. In Vivo Joint Retention Assay

The mouse knee joint retention assay was assessed by intra-articular injection of 10 μl of 10 μM IRDye 800CW-labeled SOD or 10 μM IRDye 800CW-labeled SOD-NPs in healthy (5-month-old) and OA (5-month-old, 2 months post DMM surgery) mouse knee joints. An IVIS Spectrum (PerkinElmer) was used to serially acquire fluorescence images within each joint over a period of 4 weeks. Using Living Image software, radiant efficiency within a fixed anatomical region of interest (ROI) was measured.

2.7. Human Cartilage Explant Penetration Assay

Human cartilage tissues were prepared from the de-identified specimens obtained at the total arthroplasty of the knee joints. Cartilage explants (6 mm in diameter and 3 mm in thickness) were harvested from lateral femoral condyle and cultured in chemically defined medium (DMEM, 1% ITS+Premix, 50 μg/mL L-proline, 0.1 μM dexamethasone, 0.9 mM sodium pyruvate and 50 μg/mL ascorbate 2-phosphate). They were treated with SOD-NP(Rhod-PE) for 0 (i.e., preincubation), 2, 4, 6 and 8 days, respectively. Medium was replaced once every 2 days with SOD-NP (Rhod-PE). For SOD-NP (Rhod-PE) penetration assay, after incubation, cartilage explants were washed three times with PBS, fixed with 4% paraformaldehyde (PFA), dehydrated with 20% sucrose+2% PVP (polyvinylpyrrolidone), followed by embedding with 20% sucrose+2% PVP+8% gelatin. Sections were mounted with DAPI Fluoromount-G Mounting Medium (Southern Biotech) and observed under confocal microscope (Zeiss LSM 710).

2.8. SOD-NPs Joint Distribution Assay

SOD-NPs joint distribution assay was performed by intra-articular injection of 10 μl of 10 μM SOD(FITC) or SOD (FITC)-NP(Rhod) in healthy (3-month-old) and injured (3-month-old, 3 days post DMM surgery) mouse knee joints. The joints were harvested at 1, 3, 7 and 14 days later for in vivo joint distribution analysis. Joints harvested at day 0 without any injection were used as negative control.

2.9. Human Synovium Explant Experiments

Human synovium tissues were prepared from the de-identified specimens obtained at the total arthroplasty of the knee joints. To evaluate the synovium protection role of SOD-NP, synovium tissues were cut into 5 mm (length)×5 mm (width)×2 mm (depth) explants with scissor and cultured with DMEM supplemented with 10% FBS, 1% ITS+Premix, 50 μg/mL L-proline, 1% Insulin, 100 μg/mL streptomycin, and 100 U/mL penicillin. Synovium explants were treated with PBS (i.e., untreated), IL-1β in combination with PBS, empty NP, free SOD or SOD-NPs for 8 days. The final IL-1β and SOD activity in the culture medium was 10 ng/mL and 500 U/mL. respectively. Medium was replaced every two days. Explants were processed into 6 μm thick paraffin sections for immunohistochemistry staining.

2.10. Histology

After euthanasia, mouse knee joints and major organs (kidney, liver, lung, heart, brain and spleen) were harvested and fixed in 4% PFA overnight. Organ sections were stained with hematoxylin and eosin (H&E). The knee joints were decalcified in 0.5 M EDTA (pH 7.4) for 3 weeks. After paraffin embedding, a serial of 6 μm-thick sagittal sections were cut across the entire medial compartment of the joint. Uncalcified cartilage area was defined from articular surface to tide mark. OA severity was measured by Mankin score as described previously.[35] Briefly, two sections within every consecutive six sections were stained with Safranin O/Fast green and scored by two blinded observers. For synovitis score, the following basic morphological parameters of synovitis were included:[39] (i) hyperplasia/enlargement of synovial lining layer, (ii) degree of inflammatory infiltration and (iii) activation of resident cells/synovial stroma, including fibroblasts, endothelial cells, histiocytes, macrophages, and multinucleated giant cells. All parameters are graded from 0 (absent), 1 (slight), 2 (moderate) to 3 (strong positive).

For immunohistochemistry assay, paraffin sections were incubated with primary rabbit antibodies: against 8-OHdG (1:100, bs-1278, Bioss), type II Collagen (1:50, ab34712, Abcam), Mmp13 (1:100, ab219620, Abcam), and Adamts5 (1:100, ab41037, Abcam) at 4° C. overnight, followed by binding with biotinylated secondary antibodies and DAB color development. Images were captured under a light microscope (Eclipse 90i, Nikon) and analyzed by Image J.

For immunofluorescence, after washing with PBS, the knee joint cryosections were stained with primary antibody against mouse Pdgfra (1:100, Santa Cruz Bio) at 4° C. overnight, followed by incubation with secondary antibody donkey anti-mouse Alexa 647(1:100, ab150107, Abcam) for 2 h at room temperature. The sections were then mounted with DAPI Fluoromount-G Mounting Medium and observed under confocal microscope (Zeiss LSM 710).

2.11. Micro-Computed Tomography (microCT) Analysis 12 weeks after DMM surgery, mouse right knee joints were harvested and the distal femur was scanned at a 6-μm isotropic voxel size with a microCT 35 scanner (Scanco Medical AG, Brüttisellen, Switzerland). All images were smoothened by a Gaussian filter (sigma=1.2, support=2.0). To measure the subchondral bone plate (SBP) thickness as described previously,[40] sagittal images were contoured for the SBP followed by generating a 3D color map of thickness for the entire SBP along with a scale bar. This map was then converted to a grayscale thickness map. The region of interest (ROI) was circled and the average SBP thickness within ROI was calculated by average grey value/255*max scale bar value.

2.12. OA Pain Analysis

The mouse knee joint pain was evaluated via von Frey filaments as described previously.[37] An individual mouse was placed on a wire-mesh platform (Excellent Technology Co.) under a 4×3×7 cm cage to restrict their move. Mice were trained to be accustomed to this condition every day starting from 7 days before the test. During the test, a set of von Frey fibers (Stoelting Touch Test Sensory Evaluator Kit #2 to #9; ranging from 0.015 to 1.3 g force) were applied to the plantar surface of the hind paw until the fibers bowed, and then held for 3 seconds. The threshold force required to elicit withdrawal of the paw (median 50% withdrawal) was determined five times on each hind paw with sequential measurements separated by at least 5 minutes.

2.13. Statistical Analysis

Data are expressed as means±SEM and analyzed by t-tests, one-way analysis of variance (ANOVA) with Dunnett's or Turkey's post-test and or Turkey's post-test for multiple comparisons using Prism 8 software (GraphPad Software, San Diego, CA). Values of $p<0.05$ were considered statistically significant.

3. Results and Discussion 3.1. Characterization of SOD-NPs

Figures 9A, 9B, 9C, 9D:
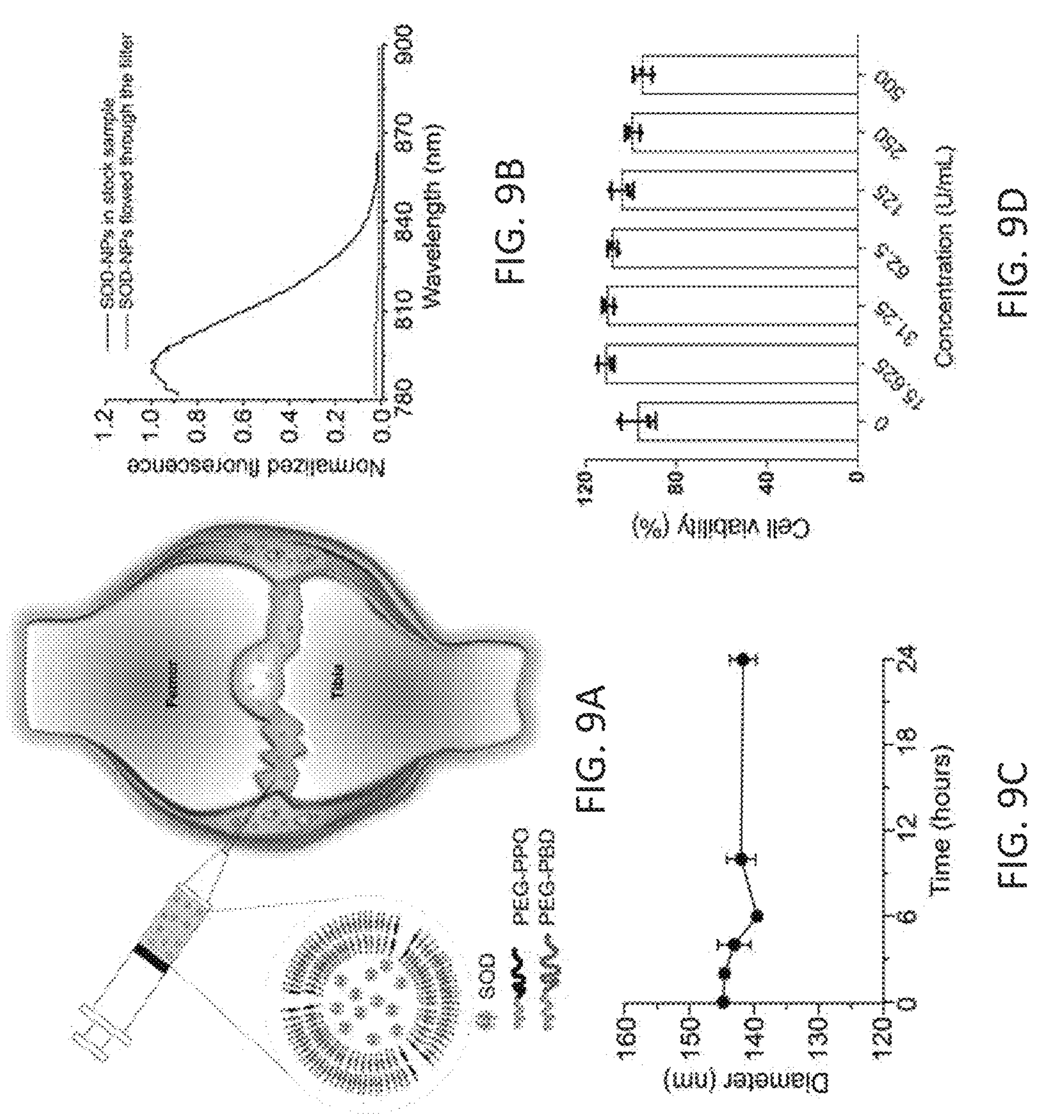
FIGS. 9A-9D. Preparation and characterization of SOD-NPs.

Porous polymersomes with encapsulated SOD were prepared as antioxidant nanoparticles. Briefly, SOD was encapsulated within the aqueous interior of polymersomes made from a mixture of two amphiphilic diblock copolymers, 75 mol % poly(ethylene glycol)-polybutadiene copolymer (PEG-PBD) and 25 mol % poly(ethylene glycol)-poly(propylene oxide) (PEG-PPO) (FIG. 9A). The average diameter of the SOD-loaded polymersomes following freeze-thaw and extrusion was approximately 120 nm. To confirm that SOD was retained within the PEG-PPO-doped polymersomes, IRDye 800CW-labeled SOD was encapsulated into the polymersomes and then incubated in phosphate buffered saline (PBS) buffer for 24 hours. Following centrifugation on a 100K MWCO centrifugal filtering device, no fluorescence was detected in the flow-through, suggesting that the SOD is retained within the PEG-PPO-doped polymersomes (FIG. 9B). In contrast, nearly all encapsulated sulforhodamine B (SRB, 559 Da), a small fluorescent dye, was released within 24 hours from the PEG-PPO-doped polymersomes (FIG. 16A). These findings clearly indicated that the PEG-PPO-doped polymersomes have high membrane permeability to small molecules, but not large molecules such as SOD. Accordingly, the activity of SOD within the PEG-PPO-doped polymersomes was significantly higher than that of the non-doped polymersomes. As shown in FIG. 16B, SOD activity in porous polymersomes was equally effective before and after dissolution of the polymersomes, suggesting that there is no loss in SOD activity in the porous polymersomes due to high accessibility to free superoxide radicals. The stability of the polymersomes was further evaluated in bovine synovial fluid. There was no observable change in the hydrodynamic diameter of polymersomes in bovine synovial fluid for 24 hours (FIG. 9C). In addition, no significant SOD release from the PEG-PPO-doped polymersomes was observed following 24 hours incubation in bovine synovial fluid (FIG. 16C). The cytotoxic effects of SOD-NPs were examined based on cell proliferation assay. In particular, various concentrations of SOD-NPs were incubated with primary mouse chondrocytes for 24 hours. The cell viability for each group was normalized to a control group that was not incubated with any SOD NPs. Generally, SOD NPs had little effect on the viability of cells up to a SOD concentration of 500 U/mL (FIG. 9D).

3.2. SOD-NPs Joint Retention and Biodistribution

Figure 10A:
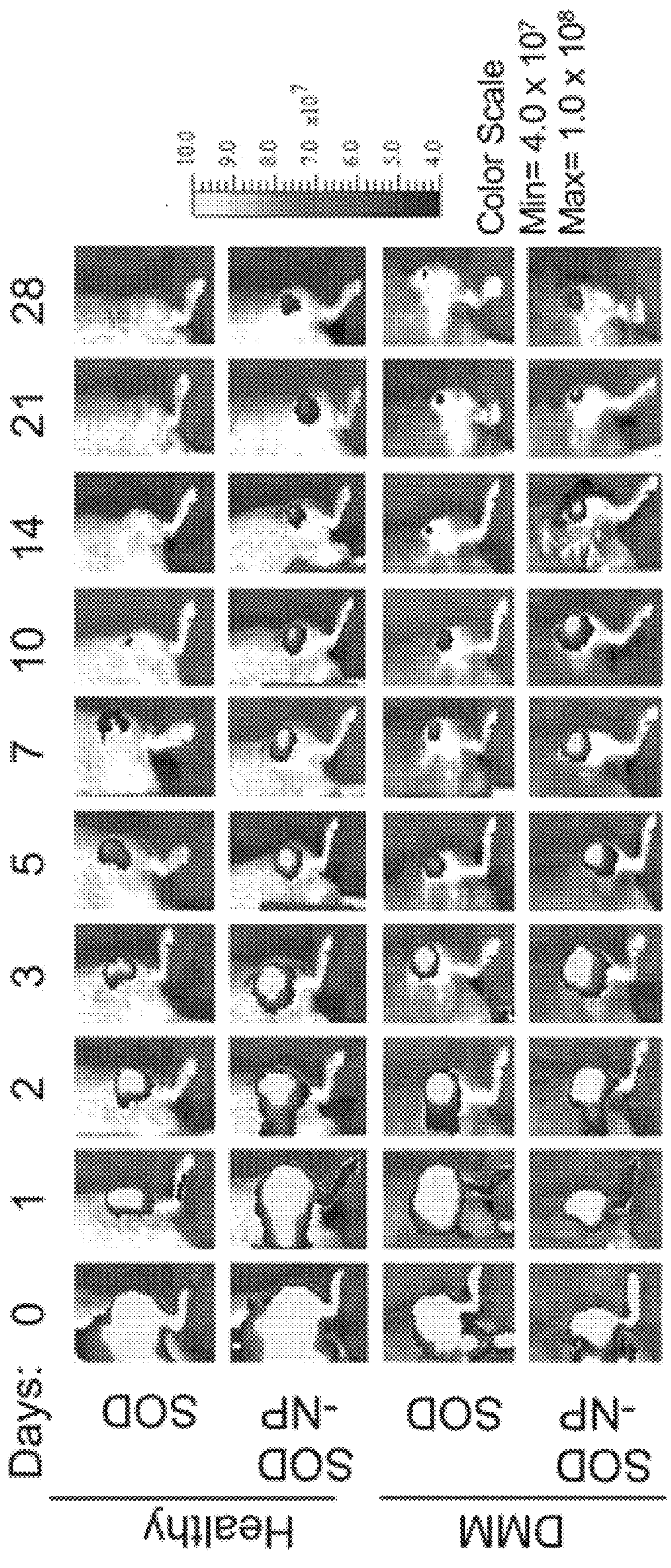
FIGS. 10A-10C. Joint retention of SOD-NPs.
Figure 10B:
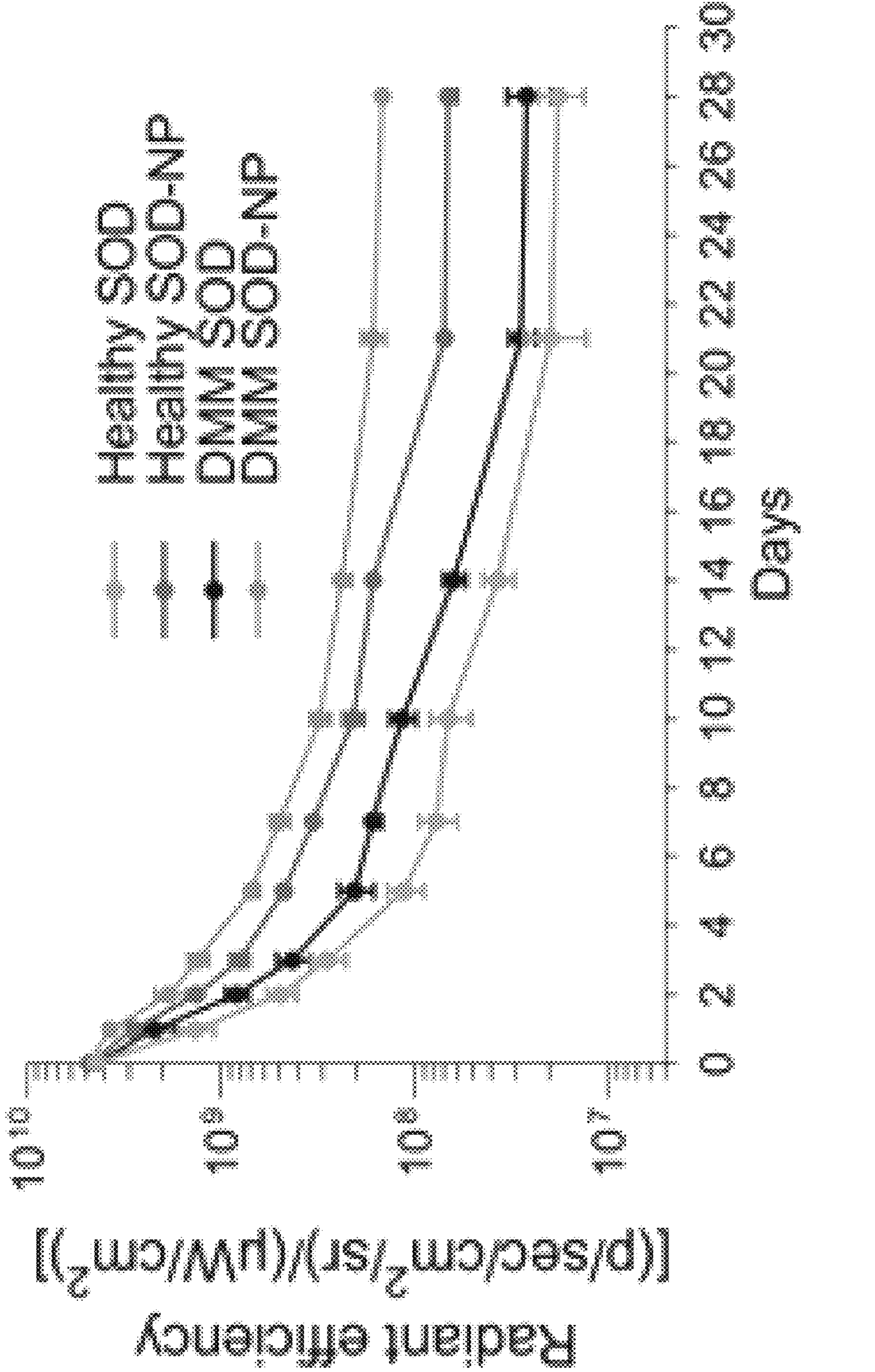
Figure 10C:
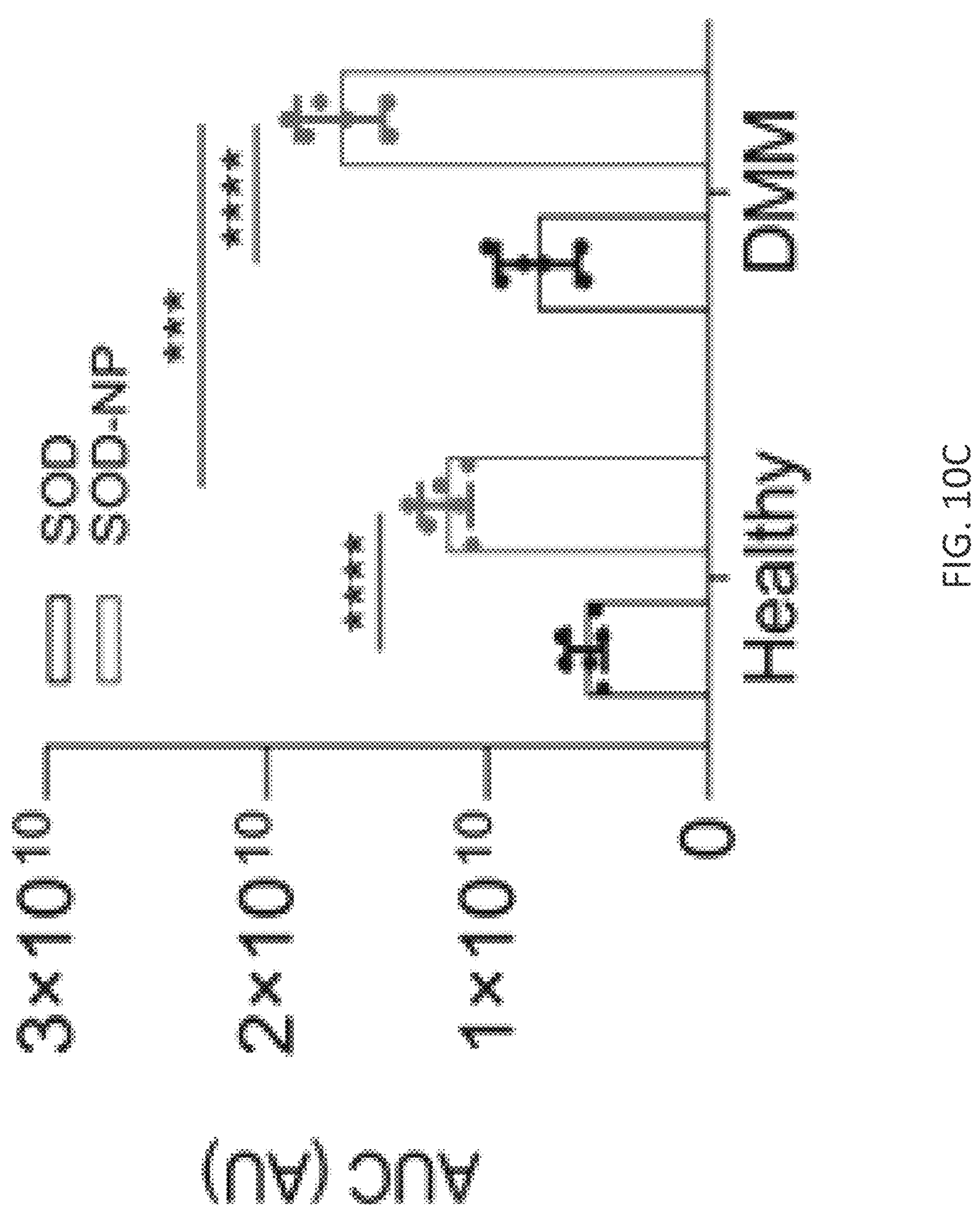

To study the retention of SOD-NPs in the knee joints, SOD was labeled with IRDye 800CW and then encapsulated into PEG-PPO-doped porous polymersomes to obtain IRDye 800CW-SOD-NPs. Destabilization of the medial meniscus (DMM) was performed on 3-month-old mice to induce knee OA. Two months later, noninjured or DMM-injured mice received a single injection of IRDye 800CW-SOD-NPs or IRDye 800CW-SOD to the knee joints. Fluorescence images of the knee joint region were acquired at various times after injection (FIG. 10A). Starting from day 5 under both normal and DMM conditions, SOD-NPs-injected joints had much higher fluorescence intensity than those with free SOD injection. At day 28, fluorescence signal was still detectable in SOD-NPs injected joints but not in joints injected with free SOD (FIG. 10B). Moreover, the retention of SOD-NPs in DMM joints was longer than that in healthy joints (FIG. 10C).

Figure 11A:
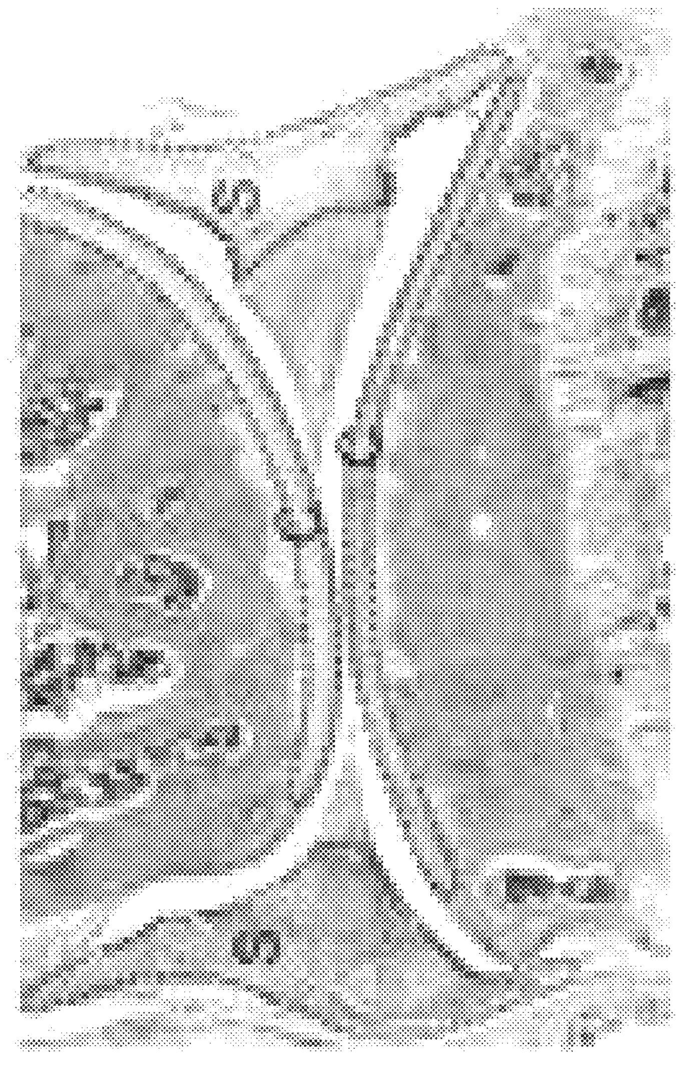
FIGS. 11A-11D. In vivo biodistribution of SOD-NPs in DMM-injured mouse knee joint.
Figures 11B, 11D:
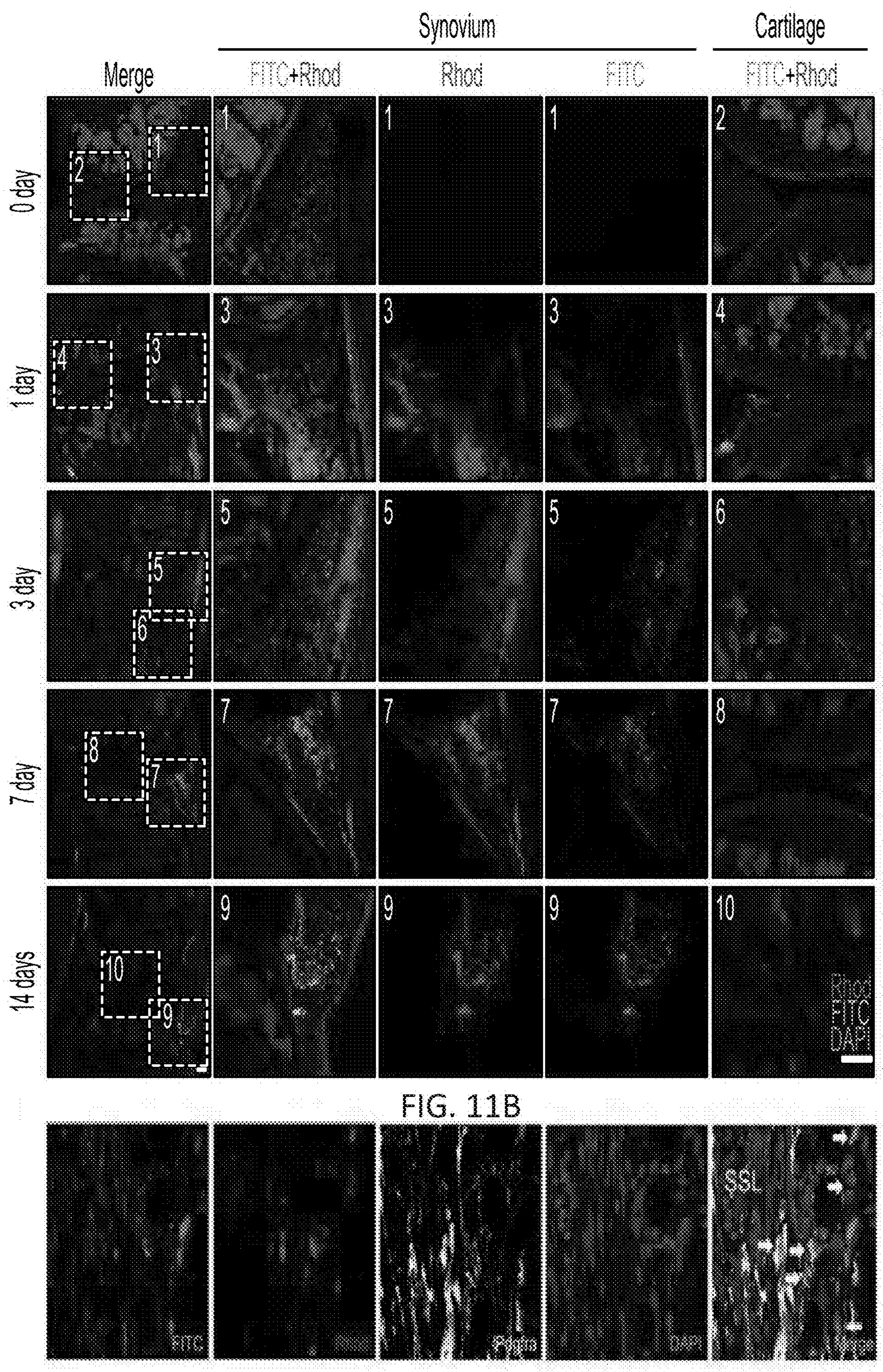
Figure 11C:
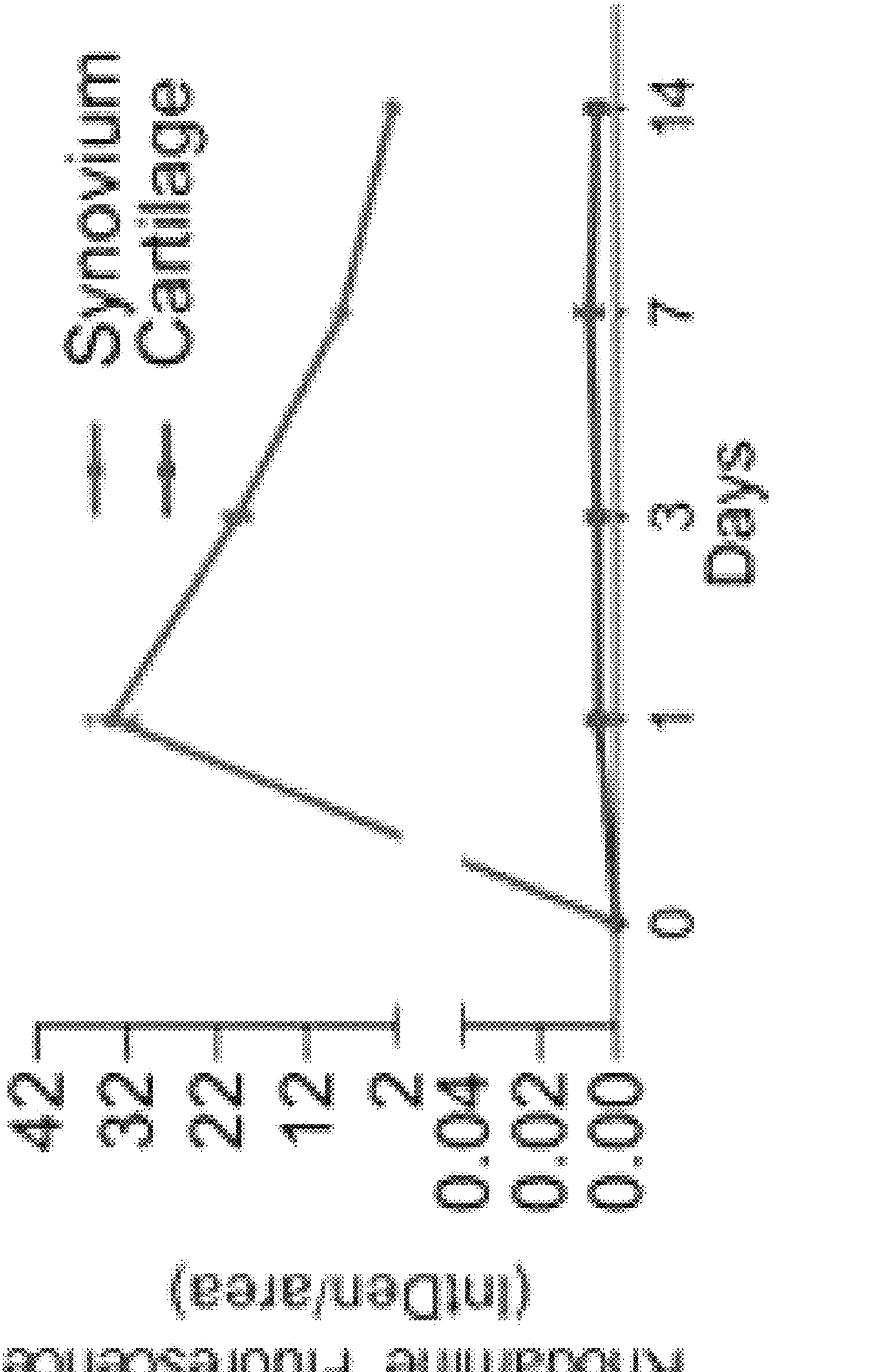
Figure 17A:
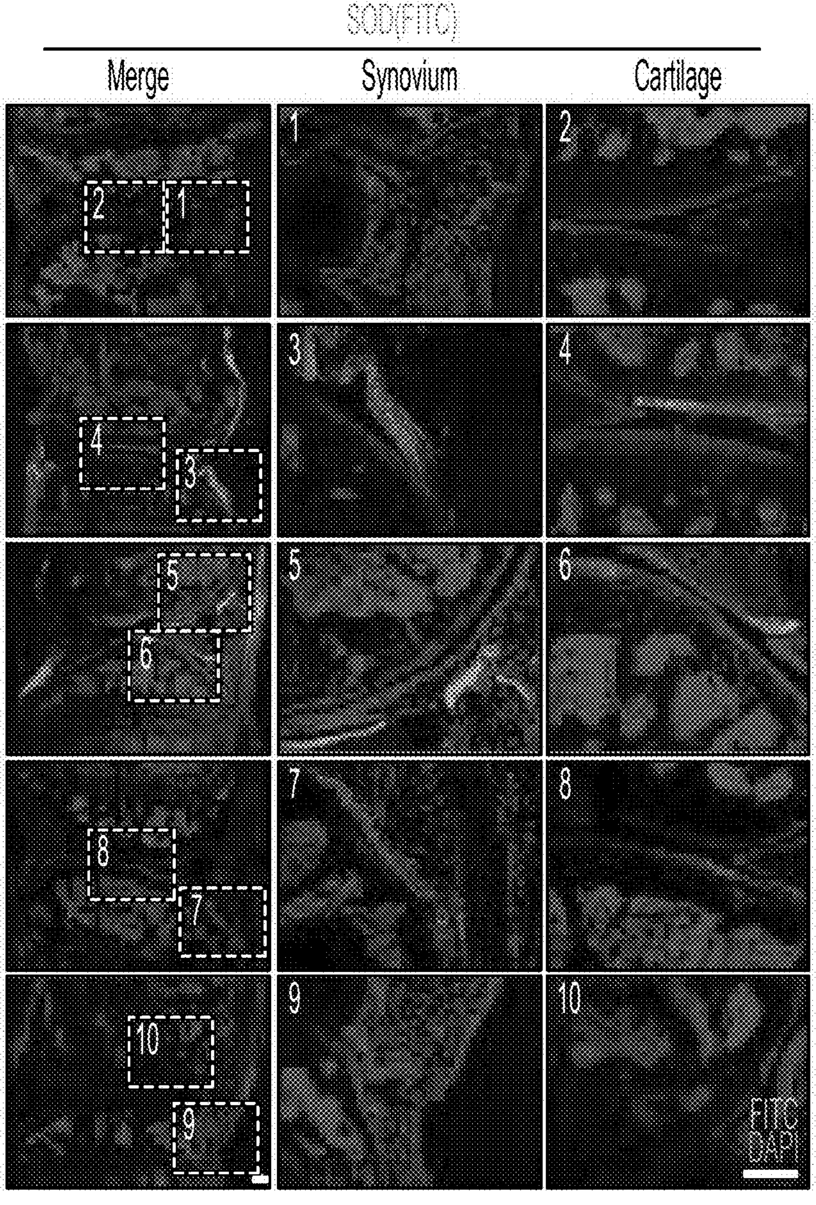
FIGS. 17A-17B. In vivo biodistribution of free SOD in injured mouse knee joint.
Figure 17B:
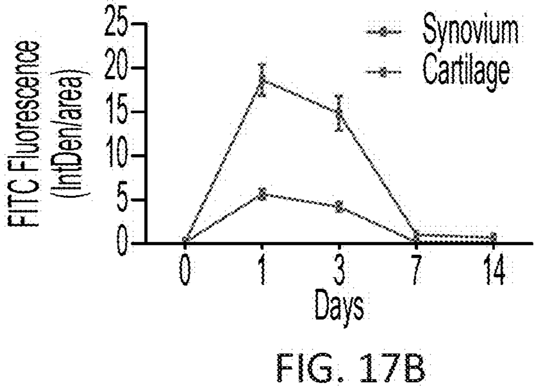
Figure 19A:
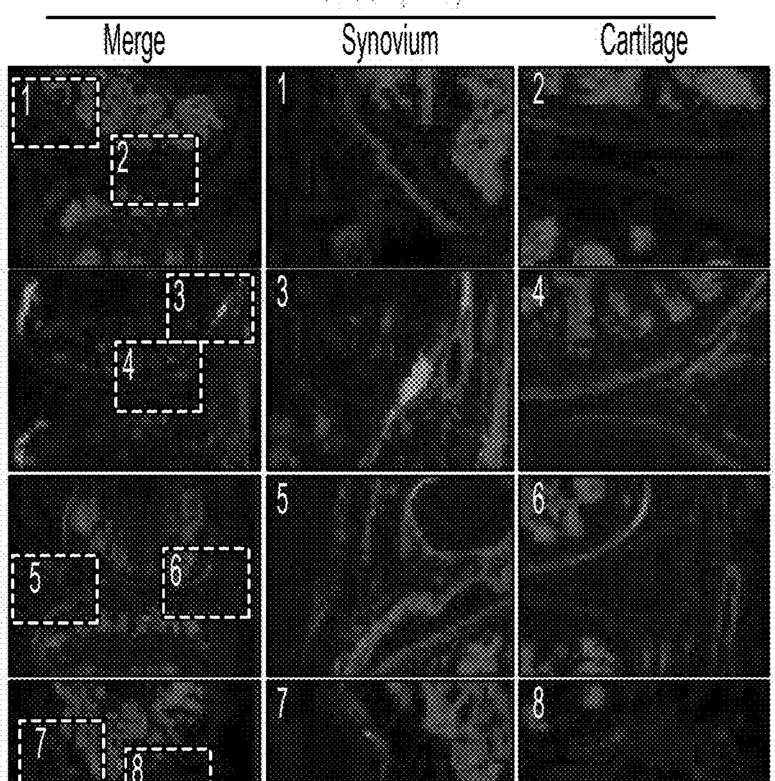
FIGS. 19A-19B. In vivo biodistribution of free SOD in healthy mouse knee joint.
Figure 19B:
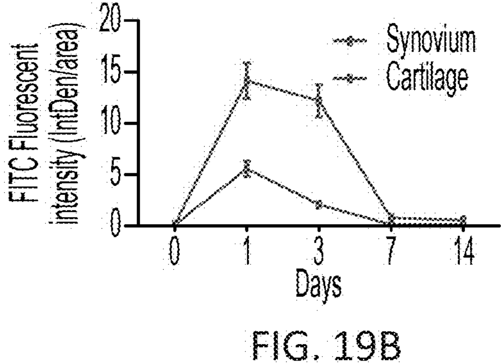

To further examine the in vivo biodistribution of SOD-NPs, we prepared dual fluorescent dyes-labeled nanoparticles (SOD(FITC)-NP(Rhod)) by encapsulating FITC-SOD into Rhod-PE-doped polymersomes. A single intra-articular injection of SOD(FITC)-NP(Rhod) into mouse knees was performed (FIG. 11A). We firstly studied the biodistribution of NPs in DMM knees. In the absence of SOD-NPs (i.e., day 0), no Rhod or FITC-based fluorescence signal was observed in any joint tissues including synovium and cartilage (FIG. 11B). However, injection of SOD(FITC)-NP (Rhod) led to a high, sustained fluorescence signal in the synovium over 14 days but almost no signal in the articular cartilage (FIG. 11B,C). As a control, a single injection of free SOD (FITC) into DMM-injured mouse knees resulted in a transient peak of FITC-based fluorescence signal in both synovium and articular cartilage at day 1-3 (FIG. 17A,B). Similar biodistribution results of SOD-NPs (FIG. 18) and free SOD (FIG. 19) were observed in healthy knee joints. Immunostaining of mouse joint at day 14 post SOD-NP injection revealed that most synovial cells with SOD-NP fluorescent signals are positive for platelet-derived growth factor receptor alpha (Pdgfra), a fibroblast marker (FIG. 11D), indicating that synovial fibroblasts (SFs) are able to uptake SOD-NPs. These data demonstrate that compared to free SOD, SOD-NPs are predominantly accumulated in synovium with prolonged retention time.

Figure 20:
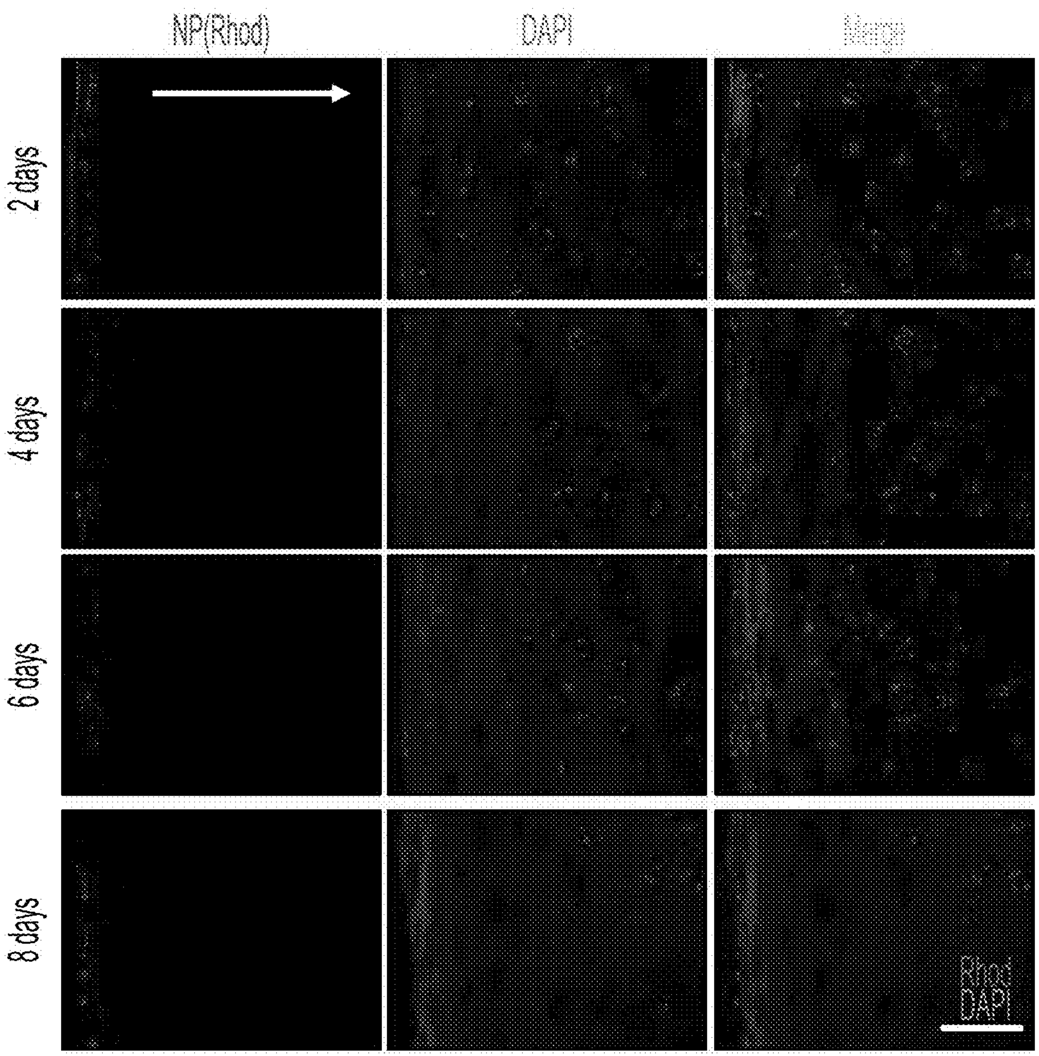
FIG. 20. Cartilage penetration of SOD-NPs. Representative fluorescence images of human cartilage explant sections incubated with SOD-NP(Rhod) for 2, 4, 6 and 8 days. Arrow indicates the diffusion direction. Scale bar: 200 μm.

To confirm that SOD-NPs cannot penetrate into cartilage, we incubated SOD-NPs(Rhod) with human cartilage explants for 2, 4, 6, and 8 days. Confocal fluorescence images of cartilage section were acquired preincubation and at various time points after incubation with NPs (FIG. 20). Only a very weak fluorescence signal was observed within the top region of the articular cartilage, even up to 8 days. These results validate that the SOD-NPs are not able to penetrate into the articular cartilage, likely due to their relatively large size.

Figures 21A, 21B, 21C, 21D:
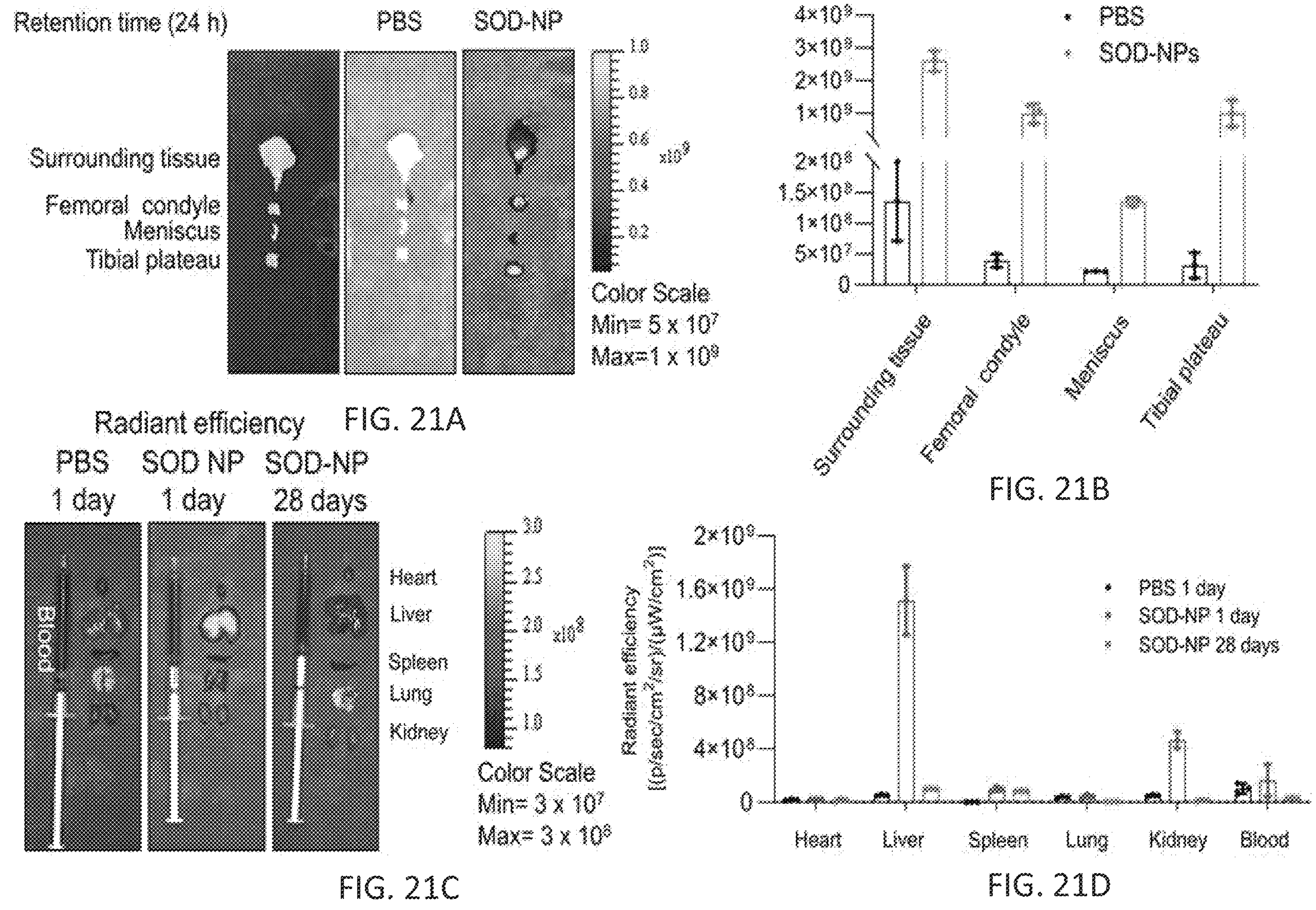
FIGS. 21A-21D. Biodistribution of NP-NPs within the knee joint components and major organs.

We also evaluated the biodistribution of SOD-NPs in other knee joint components, internal organs, and blood. At 24 hours after a single intra-articular injection, fluorescence signals were detected on the surrounding soft tissues, including femoral condyles, tibial plateau and meniscus (FIG. 21A,B). The accumulation of the SOD-NPs was mainly observed in the liver and kidney, but no fluorescence signal was detected in blood, indicating that SOD-NPs were almost cleared from circulation (FIG. 21C,D). One month later, no fluorescence signal was observed in the liver and kidney.

3.3. SOD-NPs Mitigate Oxidative Damages in OA Synovial Explants

Figure 12B:
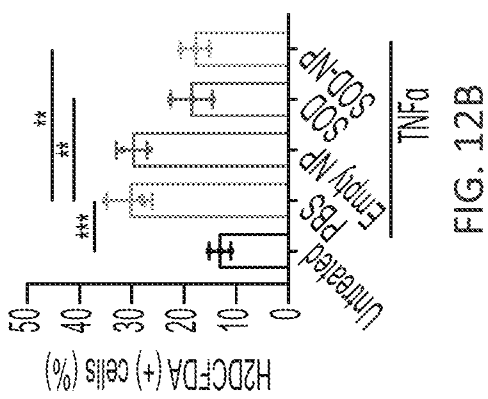
FIGS. 12A-12H. Attenuation of oxidative damage by SOD-NPs in mouse SFs and human OA synovial explants.
Figure 12A:
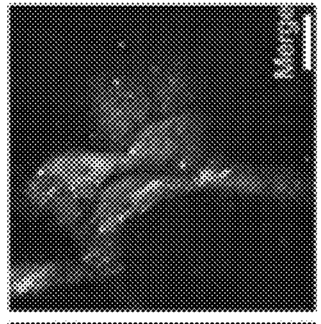
Figure 12A:
Figure 12A:
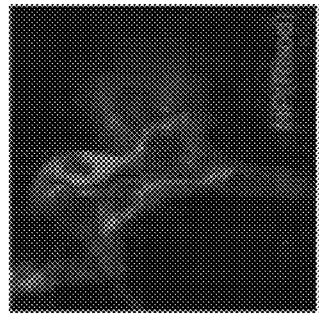
Figure 12A:
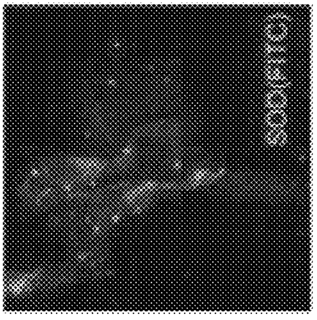
Figures 12C, 12D, 12E, 12F, 12G, 12H:
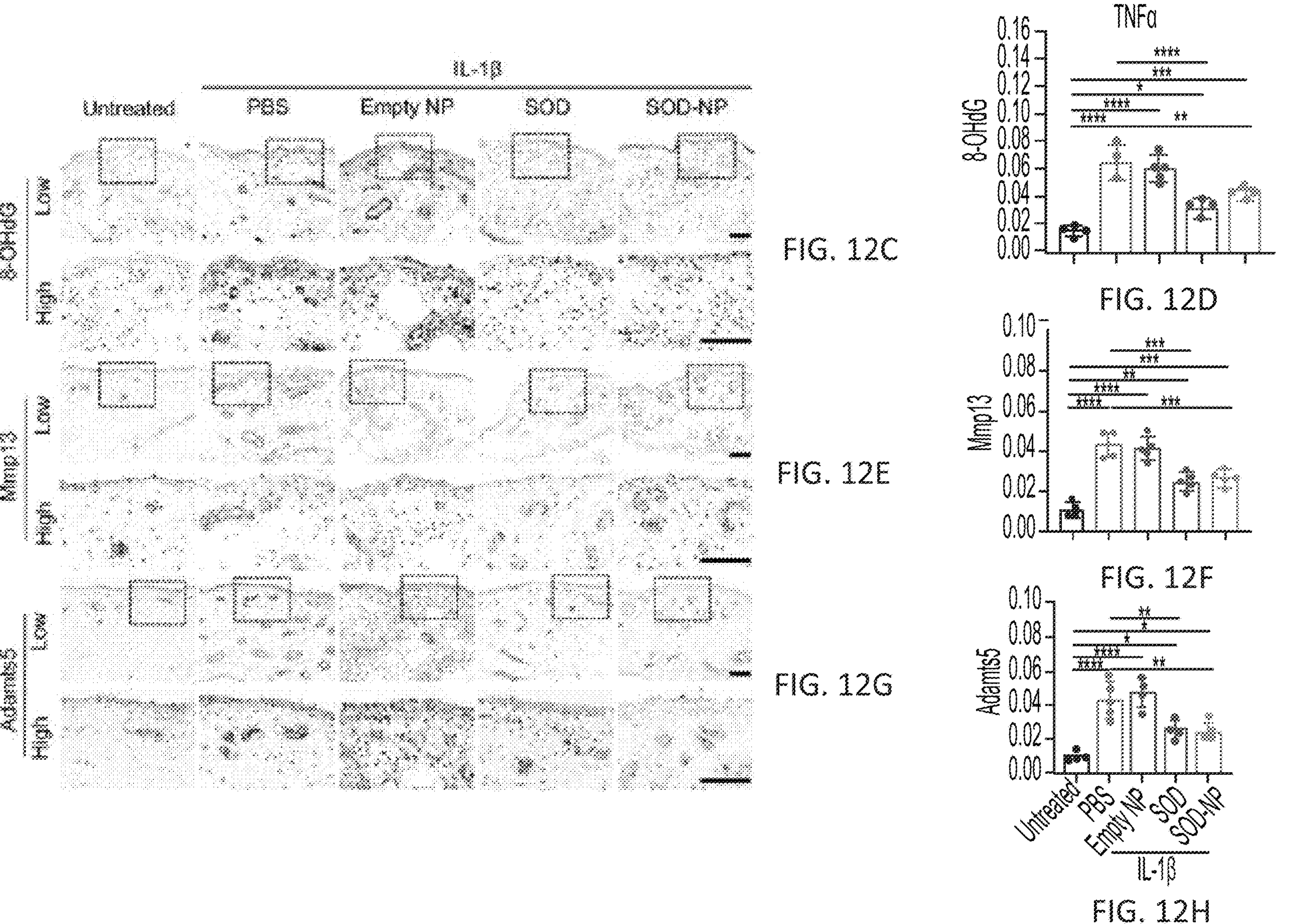
Figure 22:
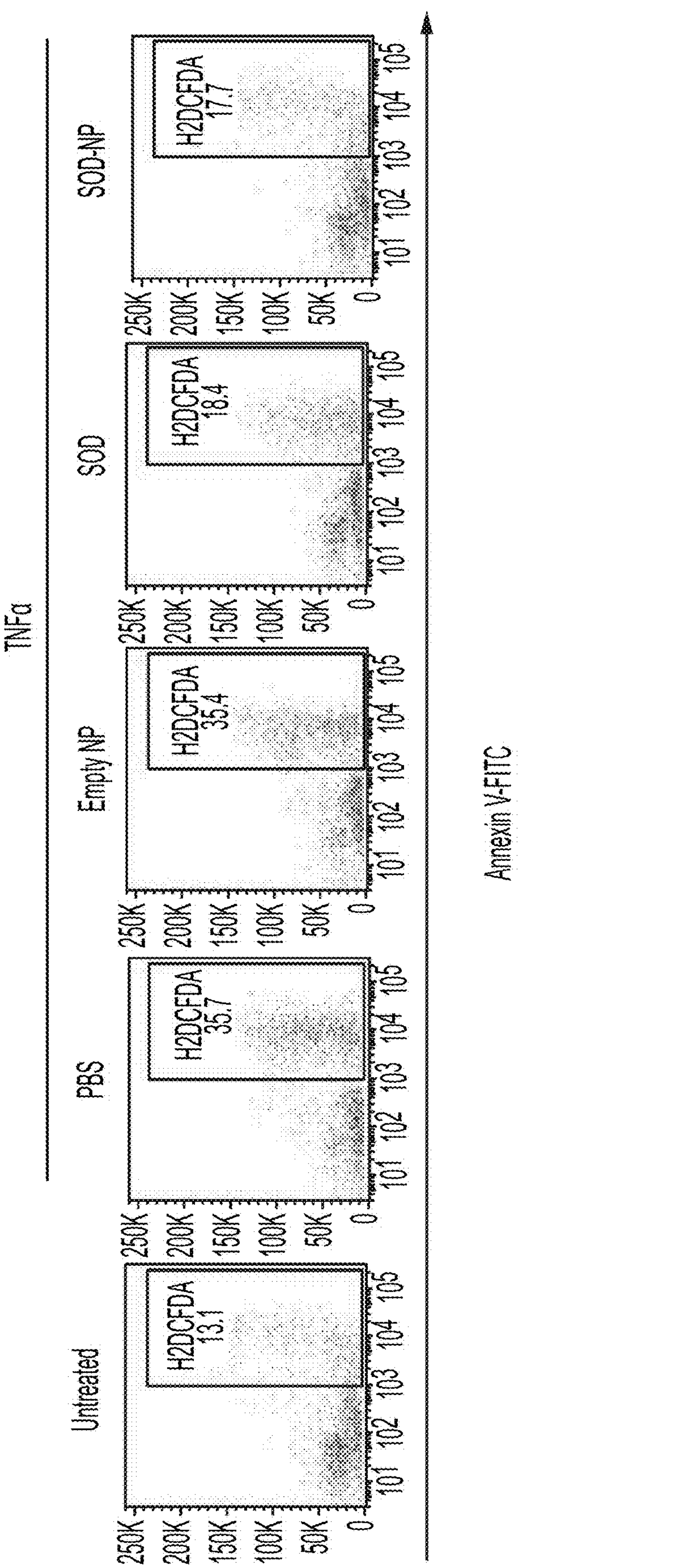
FIG. 22. SOD-NP reduces ROS production in mouse synovial fibroblasts induced by TNFα. Mouse SFs were treated with TNFα in the presence of PBS, empty NP, SOD, and SOD-NP for 24 h and harvested for flow analysis of ROS marker H2DCFDA.

Since in vivo biodistribution study suggested that SOP-NPs are mainly accumulated in synovium, we next investigated the effect of SOD-NPs on synovial cells. Adding SOD(FITC)-NP(Rhod) to cultured SFs clearly showed endocytosis of SOD-NPs (FIG. 12A). Flow cytometry revealed that tumor necrosis factor-alpha (TNFα) drastically increased ROS level, marked by 2',7'-Dichlorodihydrofluorescein diacetate (H2DCFDA), in SFs by 2.33-fold (FIG. 12B and FIG. 22). This increase was attenuated by SOD and SOD-NPs, but not empty NP (i.e., no SOD encapsulation), suggesting potent anti-ROS activity of SOD-NPs. Next, we cultured human synovial explants and treated them with interleukin-1β (IL-1β) to induce OA-like phenotypes. As expected, 8 days of IL-1β treatment drastically increased the amounts of oxidative stress marker 8-hydroxy-2'-deoxyguanosine (8-OHdG, 4.4-fold) and catabolic proteases, such as Mmp13 and Adamts5 (4.2- and 4.1-fold, respectively), in the synovial explant, both at synovial lining layer and sublining layer (FIG. 12C-H). Empty NP alone did not affect these OA-related changes. Meanwhile, the addition of SOD to the culture medium with explants significantly attenuated IL-1β-induced 8-OHdG, Mmp13, and Adamts5 amounts by 52.1%, 42.7%, and 40.5%, respectively. SOD-NPs had a similar effect, leading to 34.4%, 40.2%, and 43.8% reductions compared to IL-1β alone. We conclude that SOD-NPs are as potent as free SOD in blocking OA-induced oxidative damage in vitro.

3.4. SOD-NPs Attenuate Joint Destruction in a Surgery-Induced Mouse OA Model

Figures 13A, 13B, 13C, 13D, 13E, 13F, 13G, 13H:
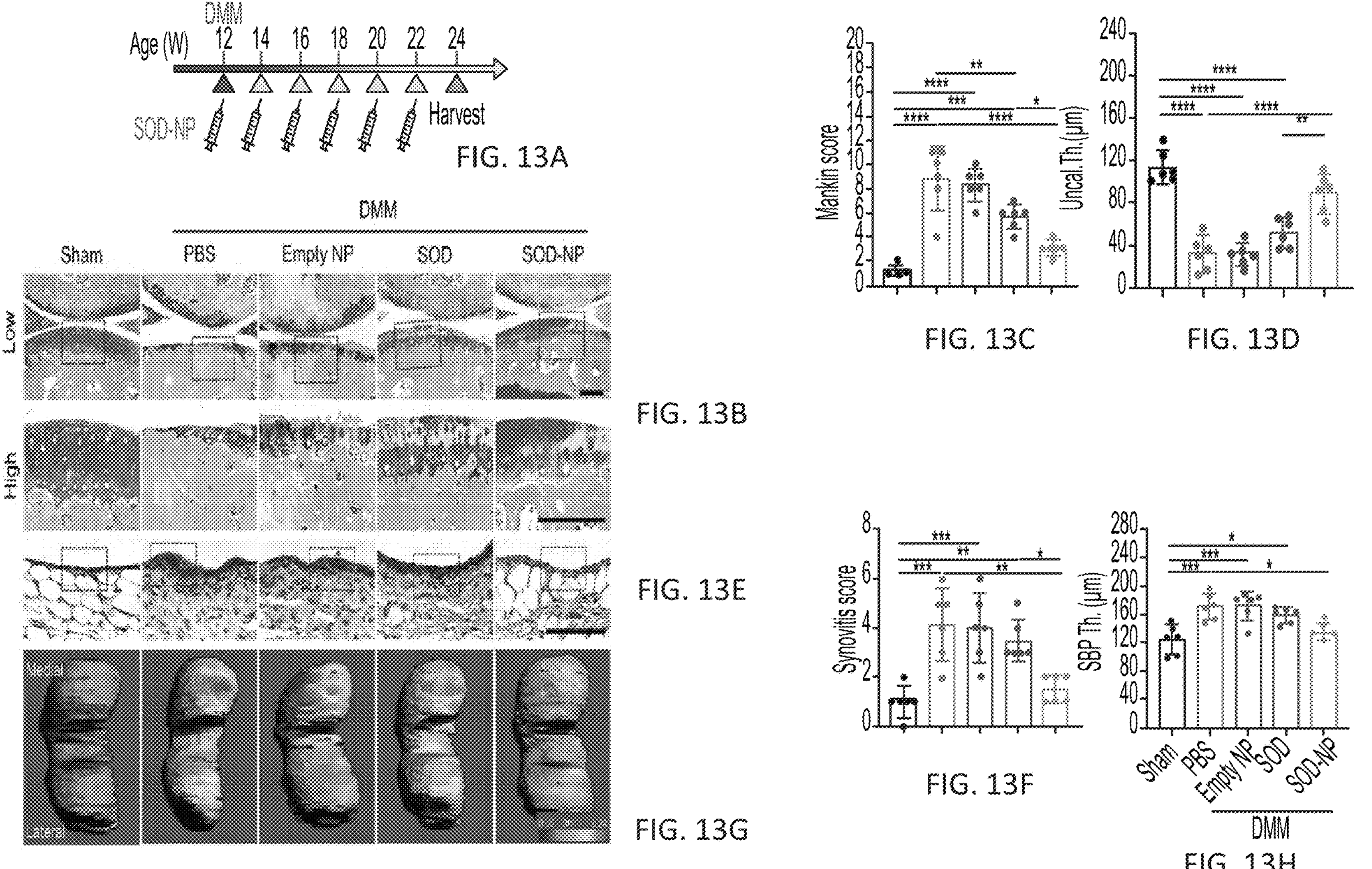
FIGS. 13A-13H. Evaluation of therapeutic efficacy of SOD-NP treatment starting immediately after the DMM surgery.
Figures 14A, 14B, 14C, 14D, 14E, 14F, 14G, 14H, 14I, 14J, 14K, 14L, 14M:
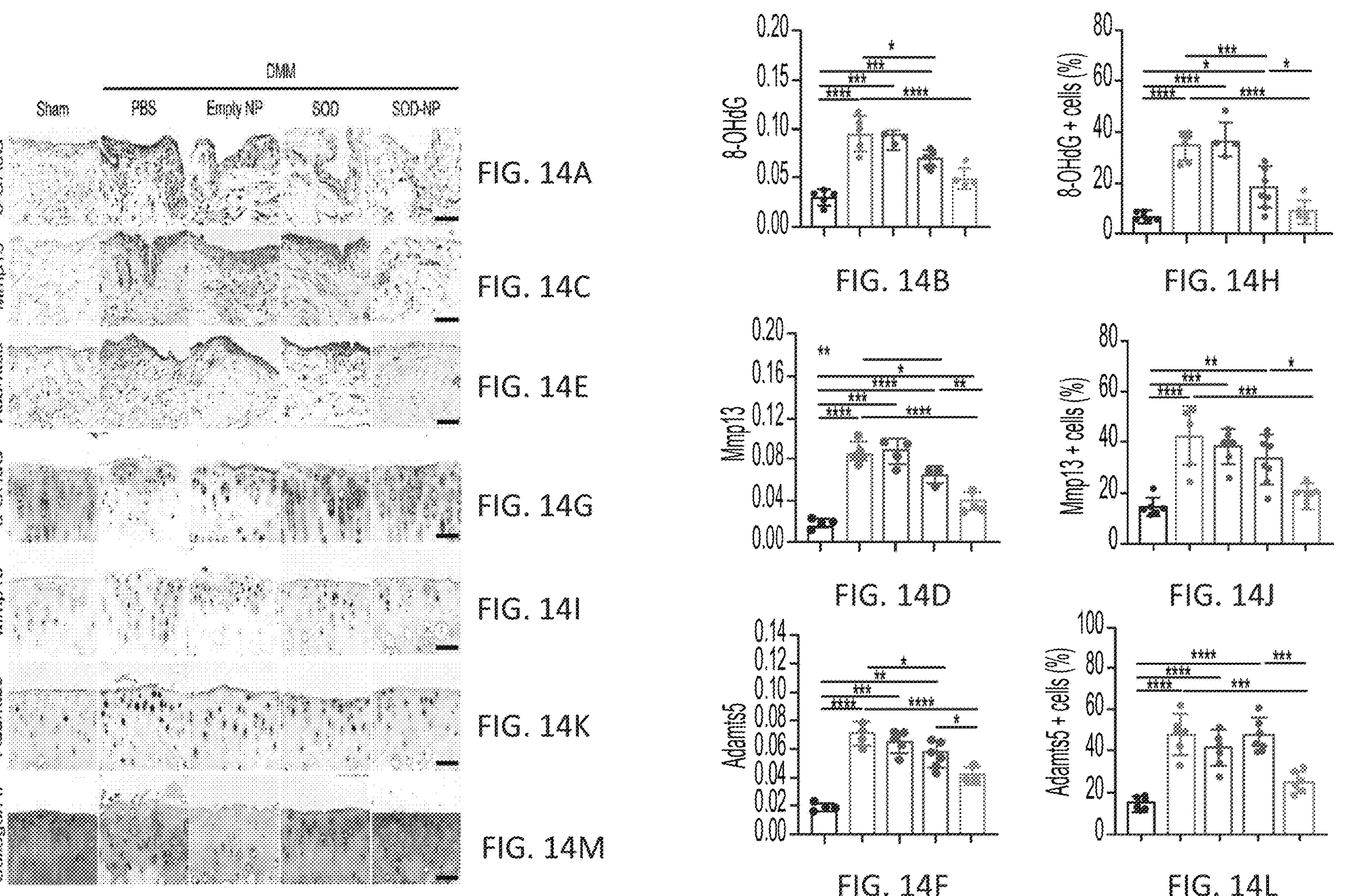
FIGS. 14A-14N. Effects of SOD-NPs on oxidative stress and matrix degradation in vivo. WT mice at 12 weeks of age received sham or DMM surgery and were treated by intra-articular injections of PBS, empty NP, SOD or SOD-NPs immediately and once every 2 weeks. Joints were harvested 12 weeks later for immunohistochemistry. Representative staining images of ROS marker 8-OHdG (FIGS. 14A, 14G), Mmp13 (FIGS. 14C, 14I), Adamts5 (FIGS. 14E, 14K) and collagen II (FIG. 14M) in synovium (FIGS. 14A, 14C, 14E) and articular cartilage (FIGS. 14G, 14I, 14K, 14M) are shown. Scale bar: 50 μm. The amounts of 8-OHdG, Mmp13, and Adamts5 in synovium were quantified in FIGS. 14B, 14D, and 14F, respectively. The percentages of chondrocytes positive for 8-OHdG, Mmp13, and Adamts5 in articular cartilage were quantified in FIGS. 14H, 14J and 14L respectively. Mean Optical Density of collagen II staining in articular cartilage was presented in N. (n=6/group). *P<0.05, P<0.01, *P<0.001, ****P<0.0001.
Figure 14N:
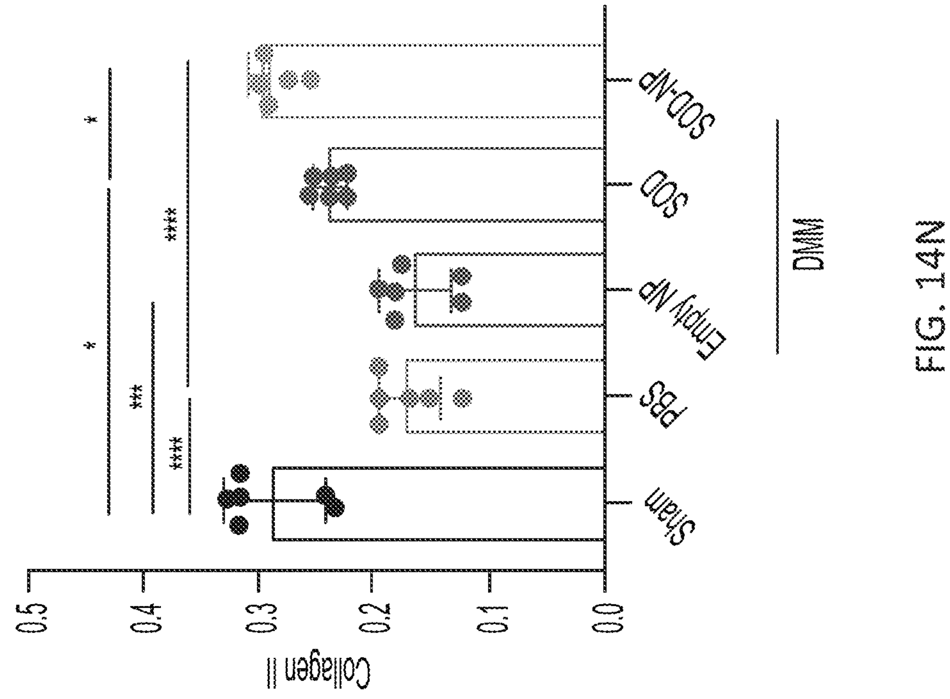

We next investigated the in vivo therapeutic effect of SOD-NPs. For this purpose, we performed DMM surgery on mouse knee joints to induce OA. SOD-NPs were then injected into knee joints once every two weeks for 12 weeks, starting immediately after the DMM surgery (FIG. 13A). Control groups included PBS, empty NP, and free SOD injections. At 12 weeks post DMM surgery, PBS- and empty NP-treated groups showed a similar level of cartilage degeneration (FIG. 13B). Specifically, a large portion of articular cartilage was eroded and cartilage surface fibrillation and cleft were obviously presented, leading to Mankin scores of 8.8 and 8.3 in PBS- and empty NP-treated groups, respectively (FIG. 13C). Interestingly, injections of free SOD alone partially attenuated this OA phenotype, with more cartilage remaining, compared to PBS and empty NP-treated groups. Meanwhile, injections of SOD-NPs maintained most cartilage integrity. The Mankin score of SOD-NP-treated group was significantly reduced compared to PBS-, empty NP-, and free SOD-treated groups. The uncalcified zones were also largely preserved in the SOD-NP-treated group (FIG. 13D), suggesting that SOD-NP treatment can efficiently attenuate OA development.

In addition to cartilage phenotypes, OA progression in DMM mice is also accompanied with synovitis and subchondral bone plate (SBP) sclerosis.[41, 42] At 12 weeks post DMM surgery, synovium thickening is apparent in DMM mice with PBS and empty NP treatment, resulting in synovitis scores of 4.1 and 4.0 respectively (FIG. 13E,F). Free SOD alone did not affect this change. However, SOD-NPs treatment significantly reduced the synovitis score to 1.5, comparable to 1.0 in sham joints. Since DMM is performed at the medial site, SBP thickness at the medial site, but not at the lateral site, increased by 38.0% at 12 weeks post-surgery in PBS treated group (FIG. 13G,H). While this bone plate sclerosis persists in empty NP- and free SOD-treated groups, SOD-NP treatment partially mitigated this change.

To understand the mechanism of the therapeutic effect of SOD-NPs, we performed staining for an oxidative stress biomarker (8-OHdG), the major component of the cartilage matrix (collagen II), and extracellular matrix proteases including Mmp13 and Adamts5 in the joints. DMM drastically increased 8-OHdG, Mmp13, and Adamts5 staining in synovium (FIGS. 14A-F) and articular cartilage (FIG. 14G-N). Both SOD and SOD-NPs treatment decreased the amounts of 8-OHdG, Mmp13 and Adamts5 in synovium, but the effect of SOD-NP (48.85%, 55.17%, 42.75% decreases in 8-OHdG, Mmp13 and Adamts5 amounts, respectively, compared to PBS) was much more drastic than with free SOD alone (26.77%, 26.19%, and 19.48% decreases). While free SOD alone reduced 8-OHdG in the articular cartilage, Mmp13 Adamts5 and collagen II amounts were not significantly changed by free SOD compared to PBS treatment. However, SOD-NPs restored the staining of 8-OHdG, Mmp13 Adamts5 and collagen II in the articular cartilage of DMM knees to similar levels as sham knees.

Figures 23A, 23B:
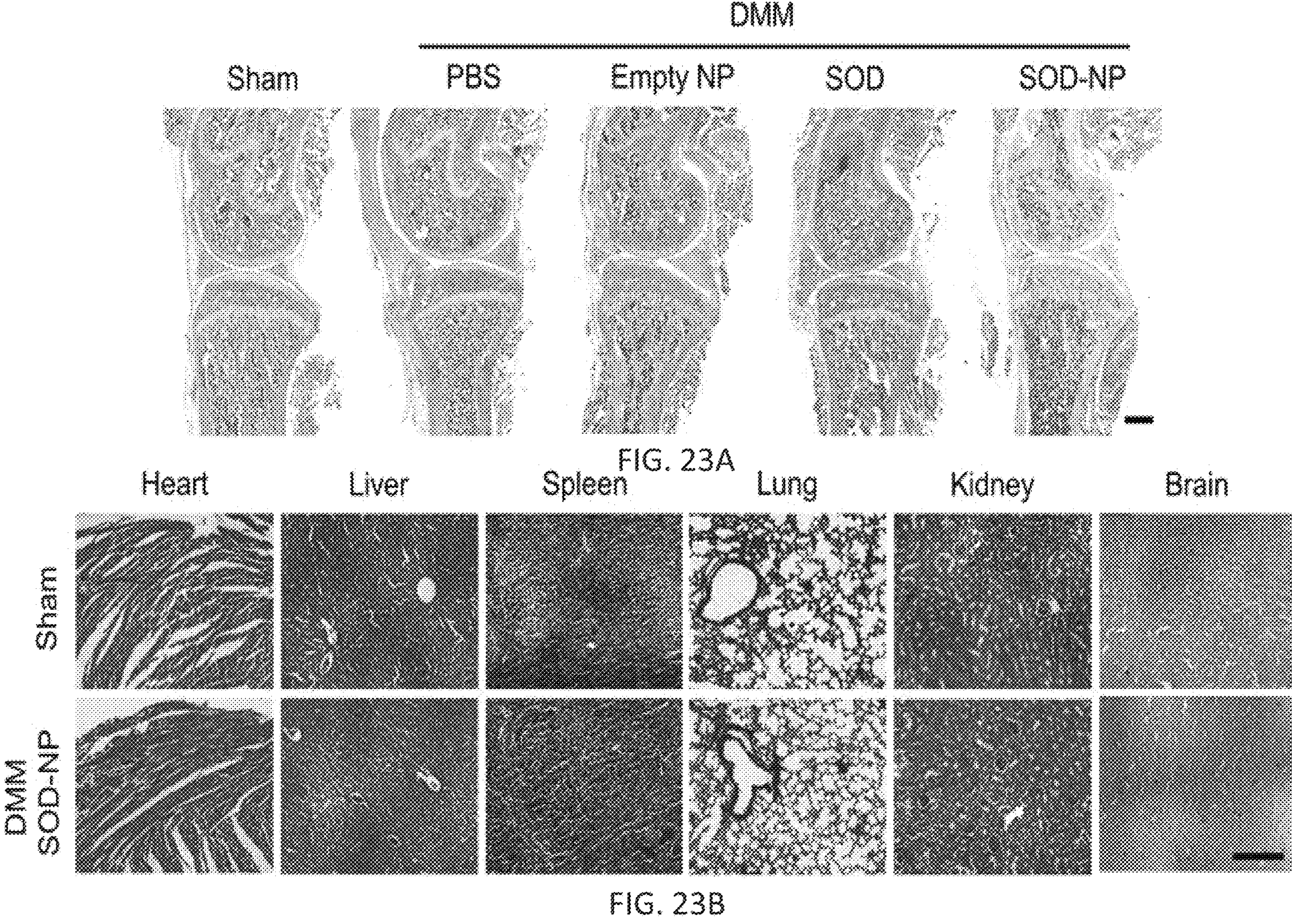
FIGS. 23A-23B. Evaluation of toxicity of SOD-NPs following treatment.

We also examined whether SOD-NPs caused any side effects to overall joint structure and major internal organs. The gross morphology of knee joints was not altered by 12 weeks of SOD-NP treatment (FIG. 23A). We also did not observe any obvious morphologic changes in the heart, liver, spleen, lung, kidney or brain between sham groups and SOD-NP-treated groups (FIG. 23B).

Figures 15A, 15B, 15C:
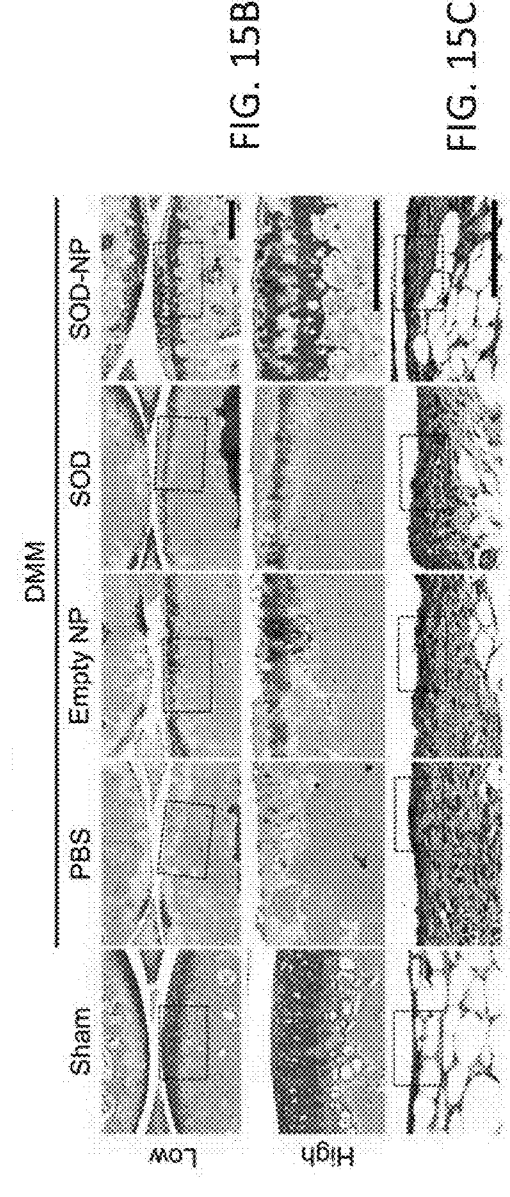
FIGS. 15A-15F. Evaluation of therapeutic efficacy of SOD-NP treatment starting 4 weeks after the DMM surgery.
Figures 15D, 15E, 15F:
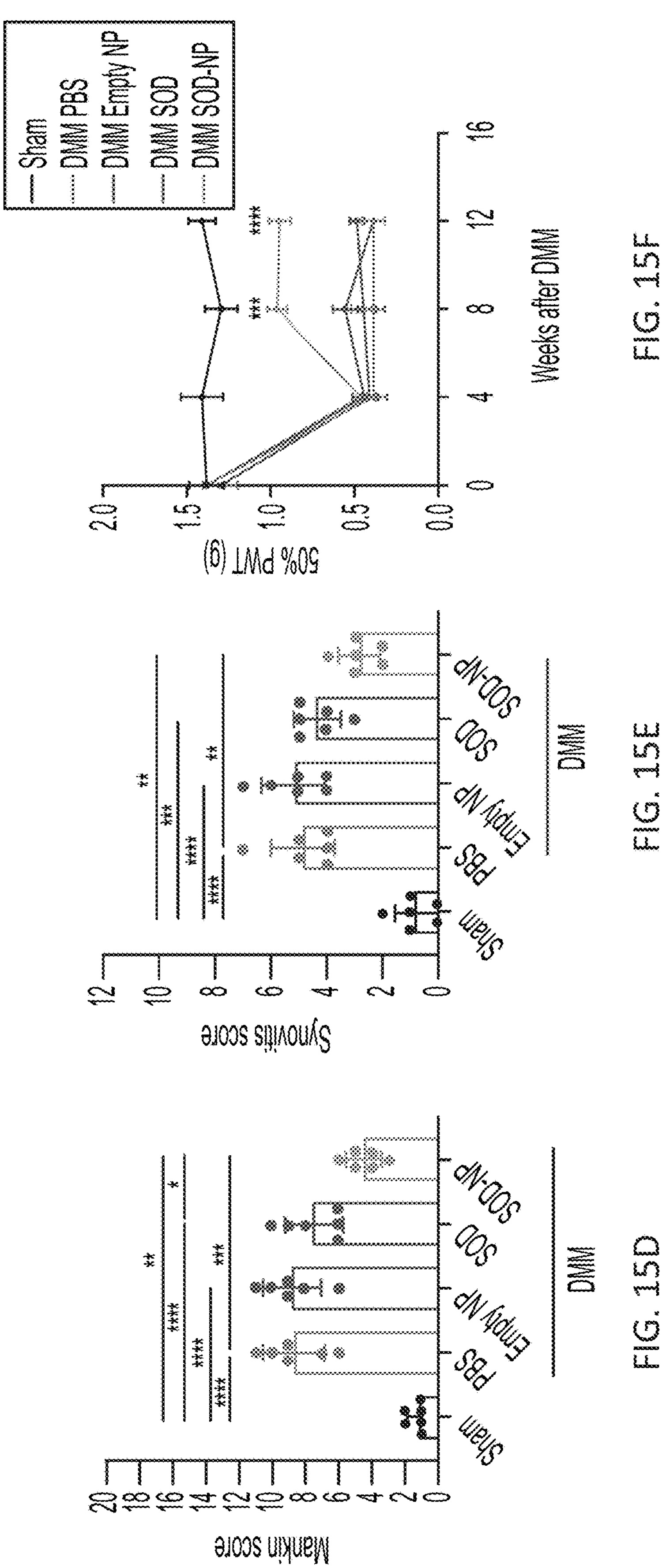

Last, to mimic a clinical scenario, we allowed OA to develop for 4 weeks after DMM surgery and then treated mice with SOD-NPs and controls (FIG. 15A). Another 8 weeks later, we observed moderate cartilage degeneration and severe synovitis in PBS-, empty NP- and free SOD-treated groups (FIG. 15B,C). Strikingly, SOD-NPs were capable of attenuating OA progression, as indicated by reduced Mankin score (FIG. 15D) and synovitis score (FIG. 15E) compared to control groups. Moreover, von Frey assay revealed that SOD-NP treatment attenuated OA-induced pain during the treatment period (FIG. 15F). Thus, our results demonstrate the therapeutic effects of SOD-NPs in preventing and rescuing OA development in a mouse model.

3.5. Discussion

Most current nanomedicine for OA therapy has focused on cartilage-targeting drug delivery. Generally, small nanoparticles penetrate cartilage more efficiently than large nanoparticles. Introducing an optimal positive charge onto small NPs could further increase their transport and enable full thickness cartilage penetration. For example, Geiger et al. conjugated insulin-like growth factor 1 (IGF-1) onto positively-charged polyamidoamine (PAMAM) dendrimers (<10 nm) and showed that the dendrimer-IGF-1 conjugates penetrated full thickness cartilage within 2 days.[21] Similarly, Bajpayee et al demonstrated that the highly positively charged Avidin (~7 nm, mimicking the small size NPs) penetrated into the full thickness of cartilage explants.[43] Our previous studies also revealed that positively charged phospholipid micelles (<15 nm) could penetrate into the full depth of cartilage. [44] To use these small-sized NPs as drug carriers for cartilage targeted OA treatment, small molecule drugs are often physically entrapped into NPs, and biological macromolecules like peptides and antibodies are often chemically conjugated onto NPs. However, the conjugation of SOD onto the surface of these NPs could not protect SOD from rapid degradation. To solve this challenge, an alternative approach is to entrap SOD within large, targeted NPs (>100 nm), so the NP layer provides a protective membrane for SOD against degradation. As described in the introduction, some large nanoparticles, such as liposomes, polymersomes and PLGA, have been used as nanocarriers for SOD loading. In this work, we used PEG-PPO-doped porous polymersomes for SOD encapsulation. The encapsulated SOD was surrounded by a highly permeable membrane, which prevents SOD degradation and allows full access of ROS, e.g., $O_2^{\cdot-}$, to the SOD. In addition, an unobstructed outer surface of SOD-encapsulated porous polymersomes can be used for the highly efficient attachment of any other functional agents, including targeting ligands or imaging contrast agents in the future.

In vivo biodistribution study in mice revealed that SOD-NPs were retained mostly in synovium tissue, but not in articular cartilage, after intra-articular injections. Since OA is recognized as a whole joint disease,[45] synovial inflammation is an important risk factor in OA initiation and progression. [42, 46, 47] Synovium is a specialized connective tissue that forms the lining of bursae and fat pads to seal the synovial cavity and fluid from surround tissues.[42] It predominantly consists of fibroblast like synoviocytes that provide lubricating molecules, such as Proteoglycan 4 (Prg4) and hyaluronic acid, and plasma-derived nutrients to the joint cavity and the adjacent cartilage.[48] During OA progression, synovium tissue undergoes characteristic changes, such as synovial lining hyperplasia, sublining fibrosis, and stromal vascularization.[49] These changes are not only associated with OA pain but also likely provides catabolic signals to the articular cartilage.[42] Previous studies suggest that synovial inflammation may occur even before cartilage degeneration, with infiltration of mononuclear cells, thickening of the synovial lining layer and production of inflammatory cytokines.[42] Our studies clearly showed that inflammatory cytokine (TNFα) and IL-1β increases ROS level in SFs and synovial explants. Moreover, IL-1β stimulates the production of destructive proteinases Mmp13 and Adamts5 in synovial explants. Those secreted catabolic factors could in turn act on cartilage chondrocytes and matrix to promote cartilage degradation. SOD-NPs can be endocytosed into SFs, leading to attenuated ROS reaction and proteinase production, as well as reduced synovitis symptoms and OA pain relief. Therefore, different from other studies that mainly targets cartilage for OA treatment, our SOD-NPs could offer another approach that targets synovium for OA therapy.

Due to technical challenges of collecting the synovial fluid from mouse knee joints, we did not analyze the ROS level in synovial fluid following SOD-NP treatment. However, it is reasonable to expect that SOD-NPs can also act as scavengers for ROS in the synovial fluid. In future large animal studies, synovial fluid can be collected at different times during the treatment.

Considering the future clinical translation of SOD-NPs, we have tested the therapeutic effects of SOD-NPs in human synovial explants. In addition, we also evaluated the ability of SOD-NPs to block OA progression 4 weeks after DMM injury. This is important since in most cases patients already have certain OA symptoms when they show up in the doctor's office. However, the current study has several limitations. For example, in this work, only SOD was encapsulated into the porous polymersomes. Co-loading other antioxidants, such as catalase, within the NPs could further minimize damage caused by other ROS, such as hydrogen peroxide (H2O2). We have used fluorescence imaging to study the penetration, retention and biodistribution of SOD-NPs within the tissues and joints. However, SOD labeled with fluorescent dyes could have different behaviors than native SOD. In future studies, a radiolabeling technique will be considered. While our current engineered SOD-NPs showed the therapeutic effects in a mouse OA model induced by DMM surgery, further studies are needed to validate the efficacy of these NPs in different OA models, such as spontaneous OA. Large animal models are also needed because the joint anatomy and physiology of small animals (i.e., mice) are significantly different from large animals and humans.

4. Conclusions

The therapeutic utility of the antioxidant enzyme SOD is largely hindered by inadequate delivery, stability, and retention at its intended site of action, due to rapid degradation and/or clearance. This can be a critical problem for the efficient removal of ROS in OA joints. This study demonstrates that SOD-loaded porous polymersomes are more efficacious than free SOD in treating OA by targeting synovium followed by cartilage protection.

REFERENCES

[1] T. Neogi, The epidemiology and impact of pain in osteoarthritis, Osteoarthr Cartilage 21(9) (2013) 1145-1153.

[2] L. F. Kou, S. Y. Xiao, R. Sun, S. H. Bao, Q. Yao, R. J. Chen, Biomaterial-engineered intra-articular drug delivery systems for osteoarthritis therapy, Drug Deliv 26(1) (2019) 870-885.

[3] K. Sinusas, Osteoarthritis: diagnosis and treatment, Am Fain Physician 85(1) (2012) 49-56.

[4] M. A. Karsdal, M. Michaelis, C. Ladel, A. S. Siebuhr, A. R. Bihlet, J. R. Andersen, H. Guehring, C. Christiansen, A. C. Bay-Jensen, V. B. Kraus, Disease-modifying treatments for osteoarthritis (DMOADs) of the knee and hip: lessons learned from failures and opportunities for the future, Osteoarthr Cartilage 24(12) (2016) 2013-2021.

[5] L. A. MacFarlane, E. Kim, N. R. Cook, I. M. Lee, M. D. Iversen, J. N. Katz, K. H. Costenbader, Racial Variation in Total Knee Replacement in a Diverse Nationwide Clinical Trial, Jcr-J Clin Rheumatol 24(1) (2018) 1-5.

[6] P. Lepetsos, A. G. Papavassiliou, ROS/oxidative stress signaling in osteoarthritis, Biochim Biophys Acta 1862(4) (2016) 576-591.

[7] F. J. Blanco, R. L. Ochs, H. Schwarz, M. Lotz, Chondrocyte Apoptosis Induced by Nitric-Oxide, Am J Pathol 146(1) (1995) 75-85.

[8] A. Klamfeldt, S. Marklund, Enhanced breakdown in vitro of bovine articular cartilage proteoglycans by conditional synovial medium. The effect of superoxide dismutase and catalase, Scand J Rheumatol 16(1) (1987) 41-45.

[9] J. C. Monboisse, J. P. Borel, Oxidative damage to collagen, EXS 62 (1992) 323-327.

[10] H. Burkhardt, M. Schwingel, H. Menninger, H. W. Macartney, H. Tschesche, Oxygen Radicals as Effectors of Cartilage Destruction—Direct Degradative Effect on Matrix Components and Indirect Action Via Activation of Latent Collagenase from Polymorphonuclear Leukocytes, Arthritis Rheum 29(3) (1986) 379-387.

[11] S. B. Nimse, D. Pal, Free radicals, natural antioxidants, and their reaction mechanisms, Rsc Adv 5(35) (2015) 27986-28006.

[12] K. Rahman, Studies on free radicals, antioxidants, and co-factors, Clin Interv Aging 2(2) (2007) 219-236.

[13] M. Koike, H. Nojiri, H. Kanazawa, H. Yamaguchi, K. Miyagawa, N. Nagura, S. Banno, Y. Iwase, H. Kurosawa, K. Kaneko, Superoxide dismutase activity is significantly lower in end-stage osteoarthritic cartilage than non-osteoarthritic cartilage, Plos One 13(9) (2018) e0203944.

[14] E. A. Regan, R. P. Bowler, J. D. Crapo, Joint fluid antioxidants are decreased in osteoarthritic joints compared to joints with macroscopically intact cartilage and subacute injury, Osteoarthr Cartilage 16(4) (2008) 515-521.

[15] J. L. Scott, C. Gabrielides, R. K. Davidson, T. E. Swingler, I. M. Clark, G. A. Wallis, R. P. Boot-Handford, T. B. Kirkwood, R. W. Taylor, D. A. Young, Superoxide dismutase downregulation in osteoarthritis progression and end-stage disease, Ann Rheum Dis 69(8) (2010) 1502-1510.

[16] E. Regan, J. Flannelly, R. Bowler, K. Tran, M. Nicks, B. D. Carbone, D. Glueck, H. Heijnen, R. Mason, J. Crapo, Extracellular superoxide dismutase and oxidant damage in osteoarthritis, Arthritis Rheum 52(11) (2005) 3479-3491.

[17] C. Ruiz-Romero, V. Calamia, J. Mateos, V. Carreira, M. Martinez-Gomariz, M. Fernandez, F. J. Blanco, Mitochondrial dysregulation of osteoarthritic human articular chondrocytes analyzed by proteomics: a decrease in mitochondrial superoxide dismutase points to a redox imbalance, Mol Cell Proteomics 8(1) (2009) 172-189.

[18] K. Lund-Olesen, K. B. Menander, Orgotein: a new anti-inflammatory metalloprotein drug: preliminary evaluation of clinical efficacy and safety in degenerative joint disease, Curr Ther Res Clin Exp 16(7) (1974) 706-17.

[19] L. Flohé, Superoxide dismutase for therapeutic use: clinical experience, dead ends and hopes, Mol Cell Biochem 84(2) (1988) 123-31.

[20] X. Gao, Y. Q. Ma, G. J. Zhang, F. Y. Tang, J. J. Zhang, J. C. Cao, C. H. Liu, Targeted elimination of intracellular reactive oxygen species using nanoparticle-like chitosan-superoxide dismutase conjugate for treatment of monoiodoacetate-induced osteoarthritis, Int J Pharmaceut 590 (2020) 119947.

[21] B. C. Geiger, S. Wang, R. F. Padera, A. J. Grodzinsky, P. T. Hammond, Cartilage-penetrating nanocarriers improve delivery and efficacy of growth factor treatment of osteoarthritis, Sci Transl Med 10(469) (2018) eaat8800.

[22] S. Brown, S. Kumar, B. Sharma, Intra-articular targeting of nanomaterials for the treatment of osteoarthritis, Acta Biomater 93 (2019) 239-257.

[23] S. Brown, J. Pistiner, I. M. Adjei, B. Sharma, Nanoparticle Properties for Delivery to Cartilage: The Implications of Disease State, Synovial Fluid, and Off-Target Uptake, Mol Pharm 16(2) (2019) 469-479.

[24] T. E. Kavanaugh, T. A. Werfel, H. Cho, K. A. Hasty, C. L. Duvall, Particle-based technologies for osteoarthritis detection and therapy, Drug Deliv Transl Res 6(2) (2016) 132-47.

[25] M. Eugenia, M. Cruz, M. M. Gaspar, M. B. F. Martins, M. L. Corvo, Liposomal superoxide dismutases and their use in the treatment of experimental arthritis, Method Enzymol 391 (2005) 395-413.

[26] X. Yun, V. D. Maximov, J. Yu, H. Zhu, A. A. Vertegel, M. S. Kindy, Nanoparticles for targeted delivery of antioxidant enzymes to the brain after cerebral ischemia and reperfusion injury, J Cerebr Blood F Met 33(4) (2013) 583-592.

[27] F. P. Chang, Y. P. Chen, C. Y. Mou, Intracellular Implantation of Enzymes in Hollow Silica Nanospheres for Protein Therapy: Cascade System of Superoxide Dismutase and Catalase, Small 10(22) (2014) 4785-4795.

[28] O. Onaca, D. W. Hughes, V. Balasubramanian, M. Grzelakowski, W. Meier, C. G. Palivan, SOD Antioxidant Nanoreactors: Influence of Block Copolymer Composition on the Nanoreactor Efficiency, Macromol Biosci 10(5) (2010) 531-538.

[29] G. D. Mao, M. J. Poznansky, Electron spin resonance study on the permeability of superoxide radicals in lipid bilayers and biological membranes, FEBS Lett 305(3) (1992) 233-236.

[30] J. Ghitman, E. I. Biru, R. Stan, H. Iovu, Review of hybrid PLGA nanoparticles: Future of smart drug delivery and theranostics medicine, Mater Design 193 (2020) 108805.

[31] E. Sah, H. Sah, Recent Trends in Preparation of Poly(lactide-co-glycolide) Nanoparticles by Mixing Polymeric Organic Solution with Antisolvent, J Nanomater 2015 (2015) 794601.

[32] E. Rideau, R. Dimova, P. Schwille, F. R. Wurm, K. Landfester, Liposomes and polymersomes: a comparative review towards cell mimicking, Chem Soc Rev 47(23) (2018) 8572-8610.

[33] D. E. Discher, A. Eisenberg, Polymer vesicles, Science 297(5583) (2002) 967-973.

[34] P. J. Altshuler, A. R. Schiazza, L. J. Luo, M. R. Helmers, B. Chhay, J. S. J. Han, R. Hu, D. A. Herbst, A. Tsourkas, Z. L. Cheng, P. Atluri, Superoxide Dismutase-Loaded Nanoparticles Attenuate Myocardial Ischemia-Reperfusion Injury and Protect against Chronic Adverse Ventricular Remodeling, Adv Ther-Germany 4 (2021) 2100036.

[35] S. Kartha, L. S. Yan, C. L. Weisshaar, M. E. Ita, V. V. Shuvaev, V. R. Muzykantov, A. Tsourkas, B. A. Winkelstein, Z. L. Cheng, Superoxide Dismutase-Loaded Porous Polymersomes as Highly Efficient Antioxidants for Treating Neuropathic Pain, Adv Healthc Mater 6(17) (2017) 1700500.

[36] J. M. McCord, I. Fridovich, Superoxide dismutase. An enzymic function for erythrocuprein (hemocuprein), J Biol Chem 244(22) (1969) 6049-55.

[37] H. Jia, X. Ma, W. Tong, B. Doyran, Z. Sun, L. Wang, X. Zhang, Y. Zhou, F. Badar, A. Chandra, X. L. Lu, Y. Xia, L. Han, M. Enomoto-Iwamoto, L. Qin, EGFR signaling is critical for maintaining the superficial layer of articular cartilage and preventing osteoarthritis initiation, Proc Natl Acad Sci USA 113(50) (2016) 14360-14365.

[38] I. Futami, M. Ishijima, H. Kaneko, K. Tsuji, N. Ichikawa-Tomikawa, R. Sadatsuki, T. Muneta, E. Arikawa-Hirasawa, I. Sekiya, K. Kaneko, Isolation and characterization of multipotential mesenchymal cells from the mouse synovium, Plos One 7(9) (2012) e45517.

[39] B. Carames, M. Olmer, W. B. Kiosses, M. K. Lotz, The relationship of autophagy defects to cartilage damage during joint aging in a mouse model, Arthritis Rheumatol 67(6) (2015) 1568-1576.

[40] H. Jia, X. Ma, Y. Wei, W. Tong, R. J. Tower, A. Chandra, L. Wang, Z. Sun, Z. Yang, F. Badar, K. Zhang, W. J. Tseng, I. Kramer, M. Kneissel, Y. Xia, X. S. Liu, J. H. C. Wang, L. Han, M. Enomoto-Iwamoto, L. Qin, Loading-Induced Reduction in Sclerostin as a Mechanism of Subchondral Bone Plate Sclerosis in Mouse Knee Joints During Late-Stage Osteoarthritis, Arthritis Rheumatol 70(2) (2018) 230-241.

[41] Y. Wei, L. Luo, T. Gui, F. Yu, L. Yan, L. Yao, L. Zhong, W. Yu, B. Han, J. M. Patel, J. F. Liu, F. Beier, L. S. Levin, C. Nelson, Z. Shao, L. Han, R. L. Mauck, A. Tsourkas, J. Ahn, Z. Cheng, L. Qin, Targeting cartilage EGFR pathway for osteoarthritis treatment, Sci Transl Med 13(576) (2021) eabb3946.

[42] A. Mathiessen, P. G. Conaghan, Synovitis in osteoarthritis: current understanding with therapeutic implications, Arthritis Res Ther 19(1) (2017) 18.

[43] A. G. Bajpayee, C. R. Wong, M. G. Bawendi, E. H. Frank, A. J. Grodzinsky, Avidin as a model for charge driven transport into cartilage and drug delivery for treating early stage post-traumatic osteoarthritis, Biomaterials 35(1) (2014) 538-549.

[44] Y. L. Wei, L. S. Yan, L. J. Luo, T. Gui, B. Jang, A. Amirshaghaghi, T. Y. You, A. Tsourkas, L. Qin, Z. L. Cheng, Phospholipase A(2) inhibitor-loaded micellar nanoparticles attenuate inflammation and mitigate osteoarthritis progression, Sci Adv 7(15) (2021) eabe6374.

[45] R. F. Loeser, S. R. Goldring, C. R. Scanzello, M. B. Goldring, Osteoarthritis: A disease of the joint as an organ, Arthritis Rheum 64(6) (2012) 1697-1707.

[46] C. Y. Wenham, P. G. Conaghan, The role of synovitis in osteoarthritis, Ther Adv Musculoskelet Dis 2(6) (2010) 349-359.

[47] X. Wang, D. J. Hunter, X. Jin, C. Ding, The importance of synovial inflammation in osteoarthritis: current evidence from imaging assessments and clinical trials, Osteoarthr Cartilage 26(2) (2018) 165-174.

[48] B. Bartok, G. S. Firestein, Fibroblast-like synoviocytes: key effector cells in rheumatoid arthritis, Immunol Rev 233(1) (2010) 233-255.

[49] B. J. E. de Lange-Brokaar, A. Ioan-Facsinay, G. J. V. M. van Osch, A. M. Zuurmond, J. Schoones, R. E. M. Toes, T. W. J. Huizinga, M. Kloppenburg, Synovial inflammation, immune cells and their cytokines in osteoarthritis: a review, Osteoarthr Cartilage 20(12) (2012) 1484-1499.

ASPECTS

The following Aspects are illustrative only and do not limit the scope of the present disclosure or the appended claims. Any part or parts of any one or more Aspects can be combined with any part or parts of any one or more other Aspects.

Aspect 1. A therapeutic composition, comprising: an anti-reactive oxygen species agent and a pervious polymersome, the pervious polymersome encapsulating the anti-reactive oxygen species agent, and the pervious polymersome having therein channels defined by a channel diblock copolymer, the channels being arranged so as to retain at least some of the anti-reactive oxygen species agent within the pervious polymersome while allowing reactive oxygen species to pass into the pervious polymersome.

Aspect 2. The therapeutic composition of Aspect 1, wherein the pervious polymersome comprises an amphiphilic diblock copolymer, the amphiphilic diblock copolymer being present as a bilayer.

Aspect 3. The therapeutic composition of Aspect 2, wherein the amphiphilic diblock copolymer comprises one or more of PEG-PBD, PEG-PCL, PEG-PLA, PEG-PLGA.

Aspect 4. The therapeutic composition of Aspect 3, wherein the amphiphilic diblock copolymer comprises PEG-PBD.

Aspect 5. The therapeutic composition of any one of Aspects 1-4, wherein the channel diblock copolymer comprises a PEG-PPO diblock copolymer.

Figure 24:
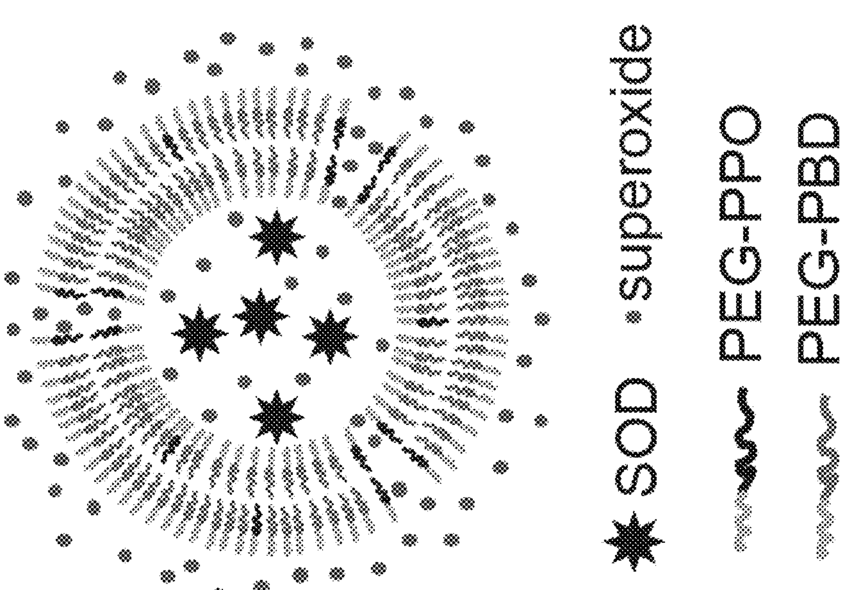
FIG. 24. Exemplary polymersome comprising PEG-PBD bilayer and PEG-PPO channel chains; as shown, the polymersome retains SOD within, while allowing superoxide to enter the polymersome and interact with the SOD retained within the polymersome. As shown, the polymersome can comprise a bilayer of PEG-PBD polymer, with PEG-PPO channel chains dispersed about the polymersome, the PEG-PPO chains (in some instances) defining channels through which the superoxide can enter the polymersome.

An exemplary polymersome comprising PEG-PBD bilayer and PEG-PPO channel chains is shown in FIG. 24. As shown, the polymersome retains SOD within, while allowing superoxide to enter the polymersome and interact with the SOD retained within the polymersome. As shown, the polymersome can comprise a bilayer of PEG-PBD polymer, with PEG-PPO channel chains dispersed about the polymersome, the PEG-PPO chains defining channels through which the superoxide can enter the polymersome.

Aspect 6. The therapeutic composition of any one of Aspects 1-5, wherein the anti-reactive oxygen species agent is an enzyme or an enzyme mimic.

Aspect 7. The therapeutic composition of Aspect 6, wherein the enzyme is at least one of superoxide dismutase or catalase.

Aspect 8. The therapeutic composition of Aspect 7, wherein the enzyme is superoxide dismutase.

Aspect 9. The therapeutic composition of any one of Aspects 1-8, wherein the pervious polymersome defines a diameter of from about 50 to about 500 nm. A diameter can be, e.g., from about 50 to about 500 nm, from about 75 to about 400 nm, from about 100 to about 350 nm, from about 125 to about 300 nm, from about 150 to about 250 nm, or even from about 175 to about 225 nm, Aspect 10. The therapeutic composition of any one of Aspects 1-9, wherein, the therapeutic composition is characterized by a retention after 24 hours of the anti-reactive oxygen species agent in a murine myocardium having an ischemia-reperfusion injury that is at least 50% of an initial amount of the anti-reactive oxygen species agent in the murine myocardium having the ischemia-reperfusion injury.

Aspect 11. The therapeutic composition of any one of Aspects 1-10, wherein the pervious polymersome has a diameter that changes by less than about 5% after 7 days in phosphate buffered saline.

Aspect 12. A method, comprising exogenous administration of a therapeutic composition according to any one of Aspects 1-11 to the myocardium of a subject having an ischemic condition.

Aspect 13. A method, comprising exogenous administration of a therapeutic composition according to any one of Aspects 1-11 to a joint of a subject, the subject optionally having an osteoarthritic condition.

Aspect 14. A method, comprising exogenous administration of a therapeutic composition according to any one of Aspects 1-11 to a subject having a septic condition, a respiratory condition (e.g., acute respiratory distress syndrome), or a dermatologic condition.

Aspect 15. A method of treating a pathology of a patient in need of treatment thereof, comprising: administering an effective amount of a therapeutic composition, the therapeutic composition comprising an anti-reactive oxygen species agent disposed within a pervious polymersome, the pervious polymersome encapsulating the anti-reactive oxygen species agent, and the pervious polymersome having therein channels defined by a channel diblock copolymer, the channels being arranged so as to retain at least some of the anti-reactive oxygen species agent within the pervious polymersome while allowing reactive oxygen species to pass into the pervious polymersome.

Aspect 16. The method of Aspect 15, further comprising, before administering, identifying a treatment site in the patient, and locally injecting the therapeutic composition at the treatment site.

Aspect 17. The method of Aspect 16, wherein the treatment site is a joint. The joint can be, e.g., a knee joint, an ankle joint, a hip joint, a shoulder joint, a neck joint, a spinal joint, an elbow joint, a wrist joint, a finger joint, a toe joint, or a foot joint.

Aspect 18. The method of Aspect 17, wherein the joint is a knee joint.

Aspect 19. The method of Aspect 16, wherein the treatment site is the myocardium.

Aspect 20. The method of Aspect 15, wherein the administrating comprises injecting.

Aspect 21. The method of Aspect 15, wherein the pervious polymersome comprises a layer (and/or a bilayer) of PEG-PBD diblock copolymer, the pervious polymersome optionally comprising a bilayer of PEG-PBD copolymer.

Aspect 22. The method of any one of Aspects 15-21, wherein the channel diblock copolymer comprises a PEG-PPO diblock copolymer.

Aspect 23. The method of any one of Aspects 15-22, wherein the anti-reactive oxygen species agent is an enzyme or an enzyme mimic.

Aspect 24. The method of Aspect 23, wherein the enzyme is at least one of superoxide dismutase or catalase.

Aspect 25. The method of Aspect 24, wherein the enzyme is superoxide dismutase.

Aspect 26. The method of any one of Aspects 15-25, wherein the pervious polymersome defines a diameter of from about 50 to about 500 nm. A diameter can be, e.g., from about 50 to about 500 nm, from about 75 to about 400 nm, from about 100 to about 350 nm, from about 125 to about 300 nm, from about 150 to about 250 nm, or even from about 175 to about 225 nm, Aspect 27. A method, comprising forming a therapeutic composition according to any one of Aspects 1-11.

Aspect 28. A kit, the kit comprising a therapeutic composition according to any one of Aspects 1-11 and an injector configured to inject the therapeutic composition into a subject. An injector can be, e.g., a syringe or a cannula.

What is claimed:

1. A therapeutic composition, comprising:
- an anti-reactive oxygen species agent and a pervious polymersome,
- the pervious polymersome encapsulating the anti-reactive oxygen species agent, and
- the pervious polymersome having therein channels defined by a channel diblock copolymer,
- the channels being arranged so as to retain at least some of the anti-reactive oxygen species agent within the pervious polymersome while allowing reactive oxygen species to pass into the pervious polymersome.

2. The therapeutic composition of claim 1, wherein the pervious polymersome comprises an amphiphilic diblock copolymer, the amphiphilic diblock copolymer being present as a bilayer.

3. The therapeutic composition of claim 2, wherein the amphiphilic diblock copolymer comprises one or more of PEG-PBD, PEG-PCL, PEG-PLA, PEG-PLGA.

4. The therapeutic composition of claim 3, wherein the amphiphilic diblock copolymer comprises PEG-PBD.

5. The therapeutic composition of claim 1, wherein the channel diblock copolymer comprises a PEG-PPO diblock copolymer.

6. The therapeutic composition of claim 1, wherein the anti-reactive oxygen species agent is an enzyme or an enzyme mimic.

7. The therapeutic composition of claim 6, wherein the enzyme is at least one of superoxide dismutase or catalase.

8. The therapeutic composition of claim 7, wherein the enzyme is superoxide dismutase.

9. The therapeutic composition of claim 1, wherein the pervious polymersome defines a diameter of from about 50 to about 500 nm.

10. The therapeutic composition of claim 1, wherein, the therapeutic composition is characterized by a retention after 24 hours of the anti-reactive oxygen species agent in a murine myocardium having an ischemia-reperfusion injury that is at least 50% of an initial amount of the anti-reactive oxygen species agent in the murine myocardium having the ischemia-reperfusion injury.

11. The therapeutic composition of claim 1, wherein the pervious polymersome has a diameter that changes by less than about 5% after 7 days in phosphate buffered saline.

12. A method, comprising exogenous administration of a therapeutic composition according to claim 1 to the myocardium of a subject having an ischemic condition.

13. A method, comprising exogenous administration of a therapeutic composition according to claim 1 to a joint of a subject, the subject optionally having an osteoarthritic condition.

14. A method, comprising exogenous administration of a therapeutic composition according to claim 1 to a subject having a septic condition, a respiratory condition, or a dermatologic condition.

15. A method of treating a pathology of a patient in need of treatment thereof, comprising:
- administering an effective amount of a therapeutic composition,
- the therapeutic composition comprising an anti-reactive oxygen species agent disposed within a pervious polymersome,
- the pervious polymersome encapsulating the anti-reactive oxygen species agent, and
- the pervious polymersome having therein channels defined by a channel diblock copolymer,
- the channels being arranged so as to retain at least some of the anti-reactive oxygen species agent within the pervious polymersome while allowing reactive oxygen species to pass into the pervious polymersome.

16. The method of claim 15, further comprising, before administering, identifying a treatment site in the patient, and locally injecting the therapeutic composition at the treatment site.

17. The method of claim 16, wherein the treatment site is a joint.

18. The method of claim 17, wherein the joint is a knee joint.

19. The method of claim 16, wherein the treatment site is the myocardium.

20. The method of claim 15, wherein the administrating comprises injecting.

21. The method of claim 15, wherein the pervious polymersome comprises a layer of PEG-PBD diblock copolymer, the pervious polymersome optionally comprising a bilayer of PEG-PBD copolymer.

22. The method of claim 15, wherein the channel diblock copolymer comprises a PEG-PPO diblock copolymer.

23. The method of claim 15, wherein the anti-reactive oxygen species agent is an enzyme or an enzyme mimic.

24. The method of claim 23, wherein the enzyme is at least one of superoxide dismutase or catalase.

25. The method of claim 24, wherein the enzyme is superoxide dismutase.

26. The method of claim 15, wherein the pervious polymersome defines a diameter of from about 50 to about 500 nm.

27. A kit, the kit comprising a therapeutic composition according to claim 1 and an injector configured to inject the therapeutic composition into a subject.

* * * * *